US009173862B2

(12) United States Patent
McKay et al.

(10) Patent No.: US 9,173,862 B2
(45) Date of Patent: Nov. 3, 2015

(54) METHODS AND COMPOSITIONS FOR TREATING AND IDENTIFYING COMPOUNDS TO TREAT AGE-RELATED MACULAR DEGENERATION

(75) Inventors: Brian McKay, Marana, AZ (US); John A. Martens, Tucson, AZ (US)

(73) Assignee: Arizona Board of Regents, a Body Corporate of the State of Arizona, Acting for and on Behalf of the University of Arizona, Tucson, AZ (US)

( * ) Notice: Subject to any disclaimer, the term of this patent is extended or adjusted under 35 U.S.C. 154(b) by 547 days.

(21) Appl. No.: 12/937,669

(22) PCT Filed: Apr. 17, 2009

(86) PCT No.: PCT/US2009/041021
§ 371 (c)(1),
(2), (4) Date: Nov. 5, 2010

(87) PCT Pub. No.: WO2009/129497
PCT Pub. Date: Oct. 22, 2009

(65) Prior Publication Data
US 2011/0044908 A1    Feb. 24, 2011

Related U.S. Application Data

(60) Provisional application No. 61/124,624, filed on Apr. 18, 2008.

(51) Int. Cl.
| *A61K 31/195* | (2006.01) |
| *A61K 31/00* | (2006.01) |
| *A61K 31/07* | (2006.01) |
| *A61K 31/355* | (2006.01) |
| *A61K 31/375* | (2006.01) |
| *A61K 33/30* | (2006.01) |
| *A61K 33/34* | (2006.01) |

(52) U.S. Cl.
CPC ............. *A61K 31/195* (2013.01); *A61K 31/00* (2013.01); *A61K 31/07* (2013.01); *A61K 31/355* (2013.01); *A61K 31/375* (2013.01); *A61K 33/30* (2013.01); *A61K 33/34* (2013.01)

(58) Field of Classification Search
None
See application file for complete search history.

(56) References Cited

U.S. PATENT DOCUMENTS

| 3,891,696 | A | | 6/1975 | Bodor et al. | |
|---|---|---|---|---|---|
| 4,035,507 | A | | 7/1977 | Bodor et al. | |
| 4,663,349 | A | | 5/1987 | Repta | |
| 4,771,073 | A | | 9/1988 | Repta | |
| 4,873,263 | A | | 10/1989 | Repta | |
| 5,345,885 | A | | 9/1994 | Yoshino | |
| 5,686,423 | A | * | 11/1997 | Wang et al. | 514/17.7 |
| 6,660,297 | B2 | | 12/2003 | Bartels et al. | |
| 2002/0102581 | A1 | * | 8/2002 | Hageman et al. | 435/6 |
| 2002/0151526 | A1 | | 10/2002 | Gallop et al. | |
| 2004/0220270 | A1 | * | 11/2004 | John et al. | 514/567 |
| 2005/0142128 | A1 | * | 6/2005 | Schraermeyer | 424/94.63 |
| 2006/0025385 | A1 | | 2/2006 | Atlas | |

FOREIGN PATENT DOCUMENTS

| WO | 9716181 | 5/1997 |
|---|---|---|
| WO | 9943286 | 9/1999 |
| WO | 0000197 | 1/2000 |
| WO | 0228882 | 4/2002 |
| WO | 03070269 | 8/2003 |
| WO | 2004069146 | 8/2004 |

OTHER PUBLICATIONS

Nowak JZ. Age-related macular degeneration (AMD): pathogenesis and therapy. 2006 Pharmacol. Rep. 58: 353-363.*
Entry for "Caucasian". Dictionary.com Unabridged. Dictionary.com website: dictionary.reference.com/browse/caucasian. Accessed Jan. 6, 2015.*
Lopez, et al., (2008) PLOS Biology 6(9): 1861-1869.
Decatur, et al., (2009) ARVO Meeting Abstracts, 50: 1866.
Decatur, et al., (2008) ARVO Meeting Abstracts, 49: 5554.
Teeple, et al., (2007) ARVO Meeting Abstracts, 48: 2537.
ISR for WO 2009/129497, mailed Oct. 13, 2009.
Lai, et al. (1973) Journal of Pharmaceutical Sciences, 62:510.
Kao, et al., (2000) Pharmaceutical Research, 17)8):978-984.
Akeo K, Shirai S, Okisaka S, Shimizu H, Miyata H, et al. (1996) Arch Ophthalmol 114: 613-616.
Gregor Z (1978) Br J Ophthalmol 62: 554-557.
Schraermeyer U, Heimann K (1999) Pigment Cell Res 12: 219-236.
Rachel, et al. (2002) Pigment Cell Res 15 : 273-281.
Okulicz JF, et al. (2003) J Eur Acad Dermatol Venereol 17: 251-256.
Donatien P, et al. (2002) Invest Ophthalmol Vis Sci 43: 1198-1203.
Russell-Eggitt I (2001) Ophthalmol Clin North Am 14: 533-546.
Oetting WS (1999) Curr Opin Pediatr 11 : 565-571.
Oetting WS, et al. (1999) Hum Mutat 13: 99-115.
Shen B, et al. (2001) Pigment Cell Res 14: 243-248.
Incerti B, et al. (2000) Hum Mol Genet 9: 2781-2788.
Bassi MT, et al. (1995) Nat Genet 10: 13-19.
Schiaffino MV, et al. (1995) Hum Mol Genet 4: 2319-2325.
Schiaffino MV, et al. (1999) Nat Genet 23: 108-112.
Schiaffino MV and Tacchetti C (2005) Pigment Cell Res 18: 227-233.
Innamorati G, et al. (2006) Pigment Cell Research 19: 125-135.
Staleva L, and Orlow SJ (2006) Exp Eye Res 82: 311-318.
Shen B, and Orlow SJ (2001) Pigment Cell Res 14: 485-490.

(Continued)

*Primary Examiner* — Michael G Hartley
*Assistant Examiner* — Jennifer Lamberski
(74) *Attorney, Agent, or Firm* — McDonnell Boehnen Hulbert & Berghoff LLP

(57) ABSTRACT

The present invention provides methods for treating or limiting development of age-related macular degeneration, as well as methods for identifying compound suitable for such use.

16 Claims, 9 Drawing Sheets

(56) References Cited

OTHER PUBLICATIONS d'Addio M, et al. (2000) Hum Mol Genet 9: 3011-3018.
Shen B, et al. (2001) Traffic 2: 202-211.
Samaraweera P, et al. (2001) Exp Eye Res 72: 3 19-329.
Schiaffino MV, et al. (1996) Proc Natl Acad Sci USA 93: 9055-9060.
Ilia M, Jeffery G (2000) J Comp Neurol 420: 437-444.
Ilia M, Jeffery G (1999) J Comp Neurol 405: 394-405.
Ito S (2003) Pigment Cell Res 16: 230-236.
Martinez-Zaguilan R, et al. (2006) Methods Mol Biol 312: 269-287.
Ferguson SS, Caron MG (2004) Methods in Molecular Biology 237: 121-126.
Barak LS, et al. (1999) J Biol Chem 274: 7565-7569.
Zhang J, et al. (1999) J Biol Chem 274: 10999-11006.
Tohgo A, et al. (2003) J Biol Chem 278: 6258-6267.
Ferguson SS, et al. (1998) Life Sci 62: 1561-1565.
Barak LS, et al. (1997) J Biol Chem 272: 27497-27500.
Barak LS, et al. (1997) Mol Pharmacol 51 : 177-184.
McKay BS, et al. (2006) Exp Neurol 201: 234-243.
Tombran-Tink J, et al. (1995) J Neurosci 15: 4992-5003.
Malchiodi-Albedi F, et al. (1998) Int J Dev Neurosci 16: 423-432.
Behling KC, et al. (2002) Mol Vis 8: 449-454.
Aymerich MS, et al. (2001) Invest Ophthalmol Vis Sci 42: 3287-3293.
Tombran-Tink J, et al. (1991) Exp Eye Res 53: 411-414.
Jablonski MM, et al. (2001) Glia 35: 14-25.
Jablonski MM, et al. (2000) J Neurosci 20: 7149-7157.
Jeffery G (1998) Eye 12(Pt 3b): 499-503.
Piccirillo R, et al. (2003) Journal of Cell Science 119: 2003-2014.
Van Raamsdonk CD, et al. (2004) Nat Genet 36: 961-968.
Young A, et al. (2008) Invest Ophthalmol Vis Sci 49: 3245-3252.
Hu J, Bok D (2001) Mol Vis 7: 14-19.
Stamer WD, et al. (2001) Eur J Pharmacol 431: 277-286.
Whiting, et al., (2005) Annual Meeting of the Association for Research in vision and Ophthalmology, FT Lauderdale, FL 46(Supps) 2297.
Berendschot, et al., (2002) IOVS, "Macular Pigment and Melanin in Age-Related Maculopathy in a General Population", vol. 43(6) pp. 1929-1932.
Kanis, et al. (2007) Graefe's Arch Clin Exp Ophthalmol, "Influence of Macular Pigment and Melanin on INcident Early AMD in a White Population", vol. 245 pp. 767-773.
Vaziri, et al., Investigative Ophthalmology & Visual Science 56: Abstract No. 2818—C0046, publication date May 5, 2015).

* cited by examiner

METHODS AND COMPOSITIONS FOR TREATING AND IDENTIFYING COMPOUNDS TO TREAT AGE-RELATED MACULAR DEGENERATION

RELATED APPLICATIONS

This application claims priority to U.S. Provisional Patent Application Ser. No. 61/124,624, filed Apr. 18, 2008, which is incorporated by reference herein in its entirety.

STATEMENT OF GOVERNMENT RIGHTS

This invention was made with government support under National Institutes of Health, Grant Number R03 EY014403. The government has certain rights in the invention.

BACKGROUND

Age-related macular degeneration ("AMD") is an aging-associated disease resulting in the loss of vision in the macula (the center of the visual field) because of damage to the retina. AMD is a prevalent disorder of the aged, with approximately 10% of patients 66 to 74 years and 30% of patients 75 to 85 years of age having some level of macular degeneration. Currently there is no effective treatment available for most patients with AMD, and no early stage intervention.

SUMMARY OF THE INVENTION

In one aspect, the present invention provides methods for treating age-related macular degeneration (AMD), comprising administering to a subject with AMD an amount effective for treating AMD of an agonist of the OA1 receptor. In a second aspect, the present invention provides methods for limiting development of AMD, comprising administering to a subject at risk of developing AMD an amount effective for limiting development of AMD of an agonist of the OA1 receptor. In one preferred embodiment of either of these aspects of the invention, the agonist of the OA1 receptor is selected from the group consisting of L-DOPA and L-DOPA analogues.

In another aspect, the present invention provides methods for identifying compounds to treat AMD, comprising contacting cells with a test compound, wherein the cells comprise:
  (a) a first cell population expressing OA1; and, optionally,
  (b) a second cell population not expressing OA1; and
  (c) identifying as positive test compounds those test compounds that increase one or both of
    (i) pigment epithelium-derived factor (PEDF) expression in the first cell population relative to one or both (A) PEDF expression in the first population of cells not contacted with the test compound, and (B) the second cell population, and
    (ii) intracellular calcium concentration in the first cell population relative to one or both (A) intracellular calcium concentration in the first population of cells not contacted with the test compound, and (B) the second cell population;
wherein the positive test compounds are candidate compounds for treating and/or limiting development of AMD.

In a further aspect, the present invention provides methods for identifying compounds to treat AMD, comprising
  (a) administering a test compound to a tyrosinase deficient pregnant female non-human mammal, wherein the test compound is administered during embryonic photoreceptor and/or retinal ganglion development; and
  (b) comparing an effect of the test compound on photoreceptor and/or retinal ganglion development in the embryo or post-natal non-human mammal, to photoreceptor and/or retinal ganglion development in an embryo or post-natal non-human mammal not administered the test compound, wherein those test compounds that increase photoreceptor and/or retinal ganglion development are candidate compounds for treating and/or limiting development of AMD.

In a still further aspect, the invention provides compositions comprising:
  (a) an amount effective of L-DOPA or an L-DOPA analogue for treating or limiting development of AMD; and
  (b) an amount effective for treating or limiting development of AMD of a composition comprising a source of vitamin C, a source of vitamin E, a source of vitamin A, a source of zinc, and a source of copper.

BRIEF DESCRIPTION OF THE FIGURES

FIG. 1(*d*) Quantification of western blot analysis by densitometry. OA1 densitometry is shown as the % of the control for paired cell cultures, transfected then split into 2 equal groups, one of which was the control, maintained in normal DMEM (control). The other group was maintained in 1 µM tyrosine DMEM (LT) until harvest. Paired t-test analysis was used to test whether the difference was significant, and * denotes p<0.001. Actin, analyzed the same way showed no differences, and p=0.724.

FIG. 1(*e-f*) Composite confocal microscopy of pigmenting RPE cells maintained in normal DMEM (e) or 1 µM tyrosine (f) then stained with anti-OA1 antibodies and imaged at 20×. Bar=25 µm.

FIG. 2(*b*) Summary data for $[Ca^{2+}]i$ in response to tyrosine, dopamine, and L-DOPA in transfected and untransfected CHO cells. Untransfected cells are shown with L-DOPA treatment. The experimental control of membrane depolarization with KCl is also shown. Each bar represents data collected from at least 10 experiments and is presented as the mean change from baseline $[Ca^{2+}]i$ after test agent addition. Error bars represent S.D., and t-test analyses were used to test for significant differences, * denotes p<0.01. Analysis of pertussis toxin sensitivity of $[Ca^{2+}]i$ increase in cells transfected to express OA1 or RPE that express the natural protein. Data represent mean of at least 6 experiments.

FIG. 2(*c*) Analysis of pertussis toxin sensitivity of $[Ca^{2+}]i$ increase in cells transfected to express OA1 or RPE that express the natural protein. Data represent mean of at least 6 experiments for each group of transfected cells and 20 individual experiments for each the treated and untreated RPE with endogenous OA1 expression. T-tests analyses were used to test for significant differences, and * denotes p<0.01.

FIG. 2(d) cAMP was measured in CHO transfected to express OA1. The control group represents transfected but untreated CHO cells and the basal level of cAMP in those cells. Cells were treated with 1.0 µM L-DOPA, 0.1 µM forskolin, L-DOPA+0.1 µM forskolin, and as a positive control 1 µM forskolin. Results represent the mean cAMP levels observed in at least 6 experiments in which all experimental groups were analyzed in a paired fashion using replicate monolayers in the same culture plate. Error bars represent the S.D. of each group, and the only significant difference observed was the increase in cAMP levels after forskolin treatment.

DETAILED DESCRIPTION OF THE INVENTION

Figure 1:
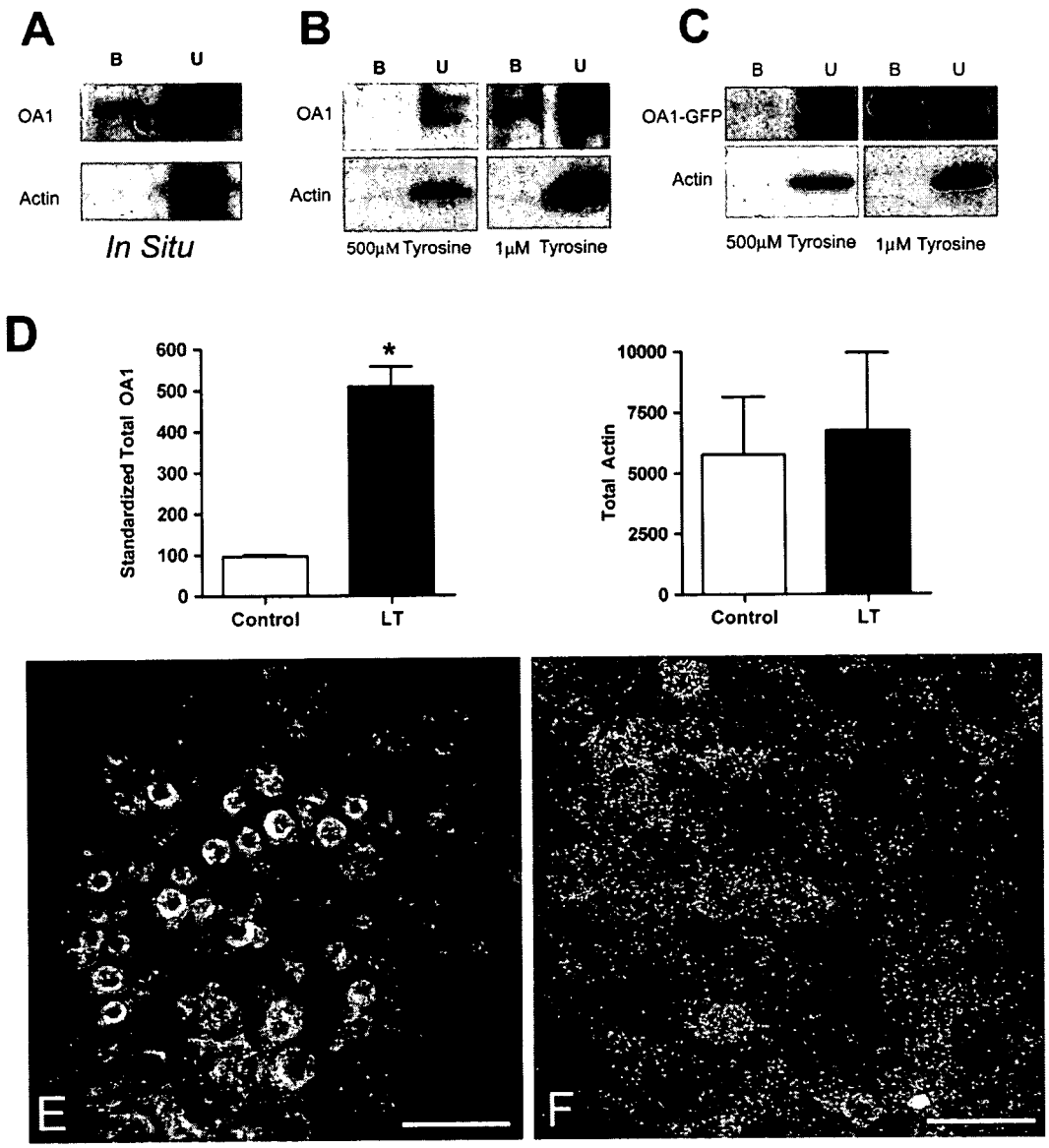
FIG. 1(*a-c*) Western blot analysis of proteins bound (B) or unbound (U) to strepavidin-conjugated beads after biotinylation of RPE in situ, cultured RPE (b), or COS cells transfected to express OA1-GFP (c). Blots were probed to visualize OA1 and actin after cell surface biotinylation and fractionation using streptavidin-conjugated beads. For cultured cells (b, c) cells were either maintained in 500 µM (normal DMEM) or 1 µM tyrosine for 3 days prior to analysis.

All references cited are herein incorporated by reference in their entirety.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise.

In a first aspect, the present invention provides methods for treating age-related macular degeneration (AMD), comprising administering to a subject with AMD an amount effective for treating AMD of an agonist of the OA1 receptor.

In a second aspect, the present invention provides methods for limiting development of AMD, comprising administering to a subject at risk of developing AMD an amount effective for limiting development of AMD of an agonist of the OA1 receptor.

The human Oa1 gene, is found on the X chromosome, and has been shown to encode a 404 amino acid protein OA1 (SEQ ID NO:2), likely to be a G-protein coupled receptor (GPCR) [12,13] based upon sequence analysis [14]. As disclosed in detail herein, the inventors have identified the OA1 signaling pathway as a critical determinant of neurosensory retina survival, such that stimulation of this pathway will provide treatment for AMD as well as a means to limit AMD development for those at potential risk. While not being bound by any mechanism, the inventors believe that OA1 and tyrosinase participate in an autocrine loop through L-DOPA that regulates the secretion of at least one potent neurotrophic factor, PEDF. Thus administration of L-DOPA can be used to stimulate OA1 activity and thus upregulate PEDF expression, making it a valuable therapeutic to treat and limit development of AMD.

As discussed in detail below, such OA1 agonists can be identified, for example, using the drug discovery methods of the third and fourth aspects of the invention. Exemplary OA1 agonists are discussed in detail below.

The subject preferably is a human.

As used herein for all aspects and embodiments of the invention, "AMD" means an aging-associated disease resulting in the loss of vision in the macula (the center of the visual field) because of damage to the retina know as Age-related Macular Degeneration. As used herein, AMD encompasses both wet and dry AMD, described in more detail below.

AMD begins with characteristic drusen (yellow deposits) in the macula between the retinal pigment epithelium and the underlying choroid. Most people with these early changes (referred to as age-related maculopathy) have good vision. People with drusen can go on to develop advanced AMD. The risk is considerably higher when the drusen are large and numerous and associated with disturbance in the pigmented cell layer under the macula.

Subjects with age-related maculopathy may progress to either of the two main forms of advanced AMD, each of which can be treated or be limited in its development using the methods of the invention. "Wet" AMD causes vision loss due to abnormal blood vessel growth in the choriocapillaries, through Bruch's membrane, ultimately leading to blood and protein leakage below the macula. Bleeding, leaking, and scarring from these blood vessels eventually causes irreversible damage to the photoreceptors and rapid vision loss if left untreated. "Dry" AMD occurs when light-sensitive cells in the macula slowly break down, gradually causing vision loss in the affected eye. Blurring in AMD is probably due to the accumulation of drusen under the retinal pigment epithelium (RPE) which alters to focal properties of the photoreceptorsby moving them out of the plane of focus.

Dry AMD may occur in one or both eyes, and can advance from age-related maculopathy into intermediate or advanced stages of dry AMD.

Intermediate Dry AMD: Either many medium-sized drusen or one or more large drusen. Some people see a blurred spot in the center of their vision. More light may be needed for reading and other tasks.

Advanced Dry AMD: In addition to drusen, a breakdown of light-sensitive cells and supporting tissue in the central retinal area. This breakdown can cause a blurred spot in the center of vision. Over time, the blurred spot may get bigger and darker, taking more of the central vision; may have difficulty reading or recognizing faces until they are very close to you.

AMD symptoms include, but are not limited to blurred/reduced central vision, central scotomas (shadows or missing areas of vision), trouble discerning one dark color from another dark color and/or one light color from another light color; slow recovery of visual function after exposure to bright light, a loss in contrast sensitivity, so that contours, shadows and color vision are less vivid, retinal pigment epithelial (RPE) disturbance (including pigment clumping and/or dropout), RPE detachment, geographic atrophy, subretinal neovascularization, and disciform scar, and distorted vision (metamorphopsia), such that a grid of straight lines appears wavy and parts of the grid may appear blank Symptoms of dry AMD and wet AMD are generally similar early during disease progression, and thus it may not be possible to determine which early-stage patients will develop dry vs. wet forms of AMD. Dry AMD develops as 'geographic atrophy', and early AMD become 'wet' AMD when new blood vessels sprout.

As used herein, "treat" or "treating" AMD means accomplishing one or more of the following: (a) reducing the severity of AMD; (b) limiting or preventing development of one or more symptoms characteristic of AMD, as described above; (c) inhibiting worsening of one or more symptoms characteristic of AMD, as described above; (d) limiting or preventing recurrence of AMD in patients that have previously had the disorder(s); and (e) limiting or preventing recurrence of one or more symptoms in patients that were previously symptomatic for AMD. Such treating includes treating of wet AMD and dry AMD.

As used herein, the term "limiting development of" AMD means to prevent or to minimize development of AMD in individuals at risk of developing AMD, as well as limiting progression of age-related maculopathy to AMD (wet or dry), or intermediate dry AMD to advanced dry or 'wet' AMD. In one preferred embodiment, the methods comprise treating a subject with drusen accumulation (ie: age-related maculopathy), to limit development of AMD. In another preferred embodiment, the methods comprise treating a subject with an amount effective of the OA1 agonist to decrease the rate of lines of loss of vision relative to a non-treated AMD subject, or subject at risk of AMD. In another preferred embodiment, the methods comprise treating a subject with wet AMD, or at risk of developing wet AMD, an amount effective of the OA1 agonist to decrease the rate and number of new blood vessel formation. As discussed in more detail below, OA1 stimulation causes the RPE to increase PEDF secretion, and PEDF is a potent anti-angiogenic factor. Thus, OA1 stimulation strategies may stop new blood vessel development in 'wet' AMD, in addition to its effects on retinal development discussed herein.

In another preferred embodiment, the methods comprise treating a subject that has blurred or reduced central vision with an amount of OA1 agonist effective to increase the lines of visual acuity in one or both eyes. In this embodiment, the lines of visual acuity are as measured by the standard Snellen test, where the increase or decrease in 'lines' of visual acuity are based on which smallest 'line' on a Snellen chart a patient can read clearly.

"Subjects at risk of developing AMD" mean anyone with any risk factor for development of AMD, including but not limited to being over 50 years old (in various preferred embodiments, over 60 years old, over 65 years old, over 70 years old, or over 75 years old), presence of drusen deposits, Caucasian race, having a blood relative that has or had AMD, a mutation in the complement factor H gene (CFH) of (Tyr402His), Arg80Gly variant of the complement protein C3 gene, hypertension, high cholesterol levels, obesity, smoking, a high fat intake, and mutations in the fibulin 5 gene. Thus, in a preferred embodiment, the subject to be treated has one or more of these risk factors, particularly in methods for limiting development of AMD.

The phrase "therapeutically effective amount," as used herein, refers to an amount that is sufficient or effective to limit development of or treat (prevent the progression of or reverse) AMD. The appropriate dosage range depends on the choice of the compound, the route of administration, the nature of the formulation, the nature of the subject's condition, and the judgment of the attending practitioner. For example, oral administration would be expected to require higher dosages than administration by intravenous injection. Variations in these dosage levels can be adjusted using standard empirical routines for optimization, as is well understood in the art.

In a preferred embodiment, the OA1 receptor agonist comprises a compound selected from the group consisting of L-DOPA and L-DOPA analogues.

L-DOPA is [2-amino-3-(3,4-dihydroxyphenyl)propanoic acid] known for use in treating Parkinson's, and has the following structure.

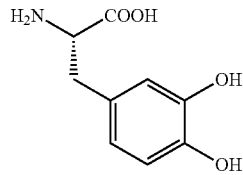

L-DOPA is commercially available and methods for its synthesis are known to those of skill in the art.

As used herein, "L-DOPA analogues" are those L-DOPA variants that retain OA1-stimulatory activity, including L-DOPA prodrugs, of which many are known in the art; exemplary such analogues are disclosed below. While not being bound by a specific mechanism of action, the inventor believes that L-DOPA binding to OA1 involves two sites of binding, one involving one or both hydroxyl groups, and one involving the carboxylic acid group. In one embodiment, the L-DOPA analogues are L-DOPA prodrugs that are metabolized to L-DOPA after administration (and generally prior to binding to OA1 on the cell surface), and thus are expected to retain OA1-stimulatory activity. In another embodiment, one or both hydroxyl group and/or the carboxyl group can be substituted to produce various analogues (prodrug or otherwise) for use in the methods of the invention.

In another embodiment, the L-DOPA analogues comprise L-DOPA esters Exemplary L-DOPA esters, and methods for preparing them, are disclosed in WO/1997/016181; U.S. Pat. No. 4,663,349; U.S. Pat. No. 4,873,263; U.S. Pat. No. 4,873,263; U.S. Pat. No. 5,345,885, and U.S. Pat. No. 4,771,073. In various preferred embodiments, the L-DOPA ester is selected from the group consisting of L-DOPA methyl ester, L-DOPA butyl ester, L-DOPA pentyl ester, L-DOPA cyclohexyl ester, L-DOPA benzyl ester, and L-DOPA ethyl ester. In various further preferred embodiments, the L-DOPA esters are selected from the alkyl, aryl and substituted and unsubstituted aralkyl esters of L-DOPA. In a further preferred embodiment, the L-DOPA esters are represented by the following formula:

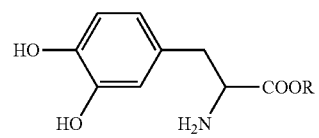

wherein R is a straight or branched chain alkyl ($C_1$-$C_{20}$) such as methyl, ethyl, propyl, butyl, myristyl, palmityl, pentyl, tetradecyl, hexadecyl and the like; aryl($C_6$-$C_9$) such as phenyl, tolyl and the like; substituted and unsubstituted mono, di or polyhydroxyalkyl($C_1$-$C_{20}$) such as benzyl, alkoxybenzyl, 4-hydroxybutyl, 2-hydroxypropyl, 2,3-dihydroxypropyl, 1,3-dihydroxypropyl, 6-hydroxyhexyl and 5-hydroxypentyl and the like optionally having a substituent such as alkoxy ($C_{1-5}$) [methoxy, ethoxy, butoxy and the like]; carbalkoxy ($C_{1-5}$) [methoxycarbonyl, ethoxycarbonyl, propoxycarbonyl butoxycarbonyl and the like]; amino; mono or dialkylamino ($C_{1-10}$) [methylamino, methylethylamino, diethylamino and the like]; acylamino($C_{1-5}$) [acetamido, butyramido and the like]; ketoalkyl ($C_{1-5}$) [methylketo, ethylketo, butylketo and the like]; halo [chloro, bromo and the like] or carboxamide; substituted and unsubstituted aralkyl($C_{7-20}$) such as benzyl, alkoxybenzyl $C_{8-14}$) [methoxy, ethoxy, isobutoxy and the like]; phenylethyl; phenylpropyl; phenylbutyl; phenylhexyl; phenyloctyl and the like; and pharmaceutically acceptable organic or inorganic counterion salts.

Synthetic processes for preparing the esters of L-DOPA and the salts thereof are known in the art, for example, in U.S. Pat. Nos. 3,891,696; 4,035,507; and 5,354,885; and Journal of Pharmaceutical Sciences, 62, p. 510 (1973), each incorporated by reference herein in their entirety.

In another embodiment, the L-DOPA analogues comprise bile acid conjugates as are known in the art. Exemplary L-DOPA bile acid conjugates, and methods for preparing them, are disclosed in WO/2002/028882 and US20020151526. Upon oral administration, these prodrugs are cleaved within the enterohepatic system to release the parent drug and/or an active metabolite from the bile acid into the systemic circulation. Significantly, only a fraction (typically <50%) <50%) of the prodrug is cleaved during each pass through the enterohepatic cycle. Thus, the enterohepatic circulation serves as a reservoir of the drug enabling sustained systemic drug levels to be achieved. Naturally occurring bile acids such as cholic acid, chenodeoxycholic acid, ursodeoxycholic acid, deoxycholic acid, ursocholic acid and lithocholic acid are particularly preferred. The site of conjugation of these bile acids to L-DOPA or other L-DOPA analogue is preferably via the 3-hydroxy group or the C-24 carboxyl moiety. Optionally, cleavable linker functionality may be introduced between the drug and the bile acid and this linker may be selected. In a preferred embodiment, such L-DOPA bile acid conjugates are represented by the following formula

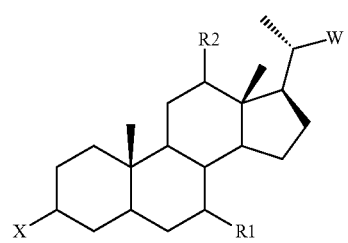

wherein R1 is selected from the group consisting of hydrogen and OH;
R2 is selected from the group consisting of hydrogen and OH;
X is selected from the group consisting of OH and D-Y—,
where Y is selected from the group consisting of a covalent bond and a cleavable linker group covalently connecting D to the steroid;
D is a member selected from the group consisting of L-DOPA and other L-DOPA analogues;
W is selected from the group consisting of (a) a substituted alkyl group containing a moiety which is negatively charged at physiological pH, which moiety is selected from the group consisting of —COOH, —SO$_3$H, —SO$_2$H, —P(O)(OR6)(OH), —OP(O)(OR6)(OH), —OSO$_3$H and the like and pharmaceutically acceptable salts thereof,
where R6 is selected from the group consisting of alkyl, substituted alkyl, aryl and substituted aryl; and (b) a group of the formula -M-Y'-D'
where M is selected from the group consisting of —CH$_2$OC(O)— and —CH$_2$CH$_2$C(O)—;
Y' is a covalent bond or a cleavable linker group covalently connecting D' to M;
D' is a member selected from the group consisting of L-DOPA and other L-DOPA analogues;
with the proviso that either X is —Y-D and/or W is -M-Y'-D' wherein the compound of formula (I) above is a substrate for an intestinal bile acid transporter;
or a pharmaceutically acceptable salt thereof.

In another embodiment, the L-DOPA analogues comprise di or tri-peptide derivatives. Exemplary L-DOPA di- or tri-peptide analogues, and methods for preparing them, are disclosed in U.S. Pat. No. 3,803,120 and U.S. Pat. No. 5,686,423. Oral absorption of the di- and tri-peptide L-DOPA prodrugs show high oral bioavailability with some compounds having the plasma concentration 60-100 fold higher than that of L-dopa. In a preferred embodiment, such L-DOPA prodrugs are represented by the following formula

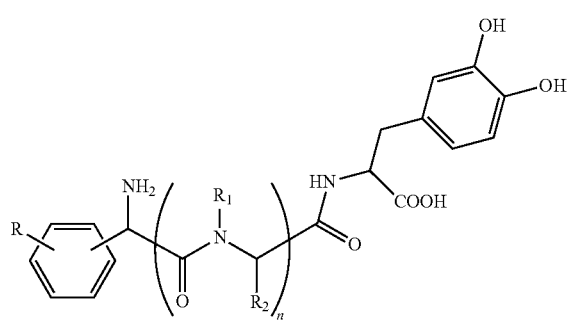

wherein n is 0 or 1; R is hydrogen or hydroxyl, preferably R is hydroxyl;
R1 is hydrogen; and
R2 is hydrogen, alkyl of from one to four carbon atoms, alkyl of from one to four carbon atoms substituted with one —OH, —SH, —SCH$_3$, —NH$_2$, —NHC(=NH)NH$_2$, —COOH, phenyl, hydroxyphenyl, indolyl or imidazolyl group, alkyl from one to four carbon atoms substituted with one carboalkoxyl group of from one to six carbon atoms, preferably R2 is hydrogen, methyl or hydroxymethyl; or
R1 and R2 together are trimethylene.
Preferably, R1 and R2 of the di- or tri-peptide derivative of L-DOPA (2-amino-3-(3,4-dihydroxyphenyl-)propanoic acid) of the formula (I) together is trimethylene.

In another embodiment, di-peptide derivatives of L-DOPA [2-amino-3-(3,4-dihydroxyphenyl)propanoic acid] are represented by the following formula

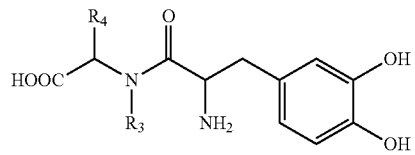

wherein R3 is hydrogen; and R4 is phenyl or hydroxyphenyl; or R3 and R4 together is trimethylene.

In another embodiment, the L-DOPA analogues comprise amine prodrugs as are known in the art. Exemplary L-DOPA amine analogues, and methods for preparing them, are disclosed in US20060025385 and WO/2004/069146. In one preferred embodiment, such L-DOPA amine analogues are represented by

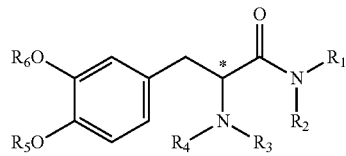

wherein *C denotes a chiral carbon;
R1, R2, R3 and R4 are each independently selected from the group consisting of hydrogen, alkyl having 1-30 carbon atoms, alkenyl having 1-30 carbon atoms, alkynyl having 1-30 carbon atoms, cycloalkyl, aryl, O-carboxy, C-carboxy, carbonyl, thiocarbonyl, O-carbamyl, O-thiocarbamyl and a fatty acid acyl, or, alternatively, R1 and R2 and/or R3 and R4 form a five- or six-membered ring; and R5 and R6 are each independently selected from the group consisting of hydrogen, alkyl, cycloalkyl, aryl and phosphonyl, or a pharmaceutically acceptable salt thereof.

Preferred L-DOPA amine analogues include: compounds wherein R5 and R6 are each hydrogen; compounds wherein R1 and R2 are each hydrogen; compounds wherein R3 and R4 are each hydrogen; compounds wherein at least one of R1, R2, R3 and R4, preferably R3 and/or R4 is carbonyl, e.g., acetyl. Additional preferred compounds according to the present embodiments include compounds wherein at least one of R1, R2, R3 and R4 is an alkyl, alkenyl or alkynyl having 1-30 carbon atoms, or, alternatively, at least one of R1, R2, R3 and R4 is a fatty acid acyl, derived from, for example, myristic acid, lauric acid, palmitic acid, stearic acid, oleic acid, arachidonic acid, linoleic acid or linolenic acid. Further preferred examples of L-DOPA amine analogues according to the present embodiments include α-amino-3,4-dihydroxybenzenepropanamide, α-N-acetyl-3,4-dihydroxy-benzenepropanamide and pharmaceutically acceptable salts thereof.

In a further preferred embodiment, L-DOPA prodrugs for use in the present invention, and methods for their synthesis, are disclosed in U.S. Pat. Nos. 4,065,566 and 4,035,507 and are represented by the formula

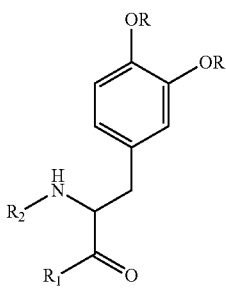

wherein each R is independently selected from the group consisting of a hydrogen atom, an acyl group, a

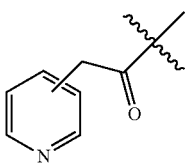

group, a —CO-pyridyl group, and a —CO—R3 group, wherein R3 represents the residue of any N,N—C1-C2 dialkylamino acid or a C4-C6 cycloalkylamino acid

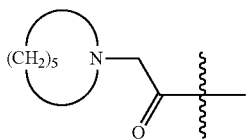

wherein R1 represents a member selected from the group consisting of a hydroxyl group and a —OM group, wherein M is an alkali metal (Na, K, etc.) or an ammonium ion; and
wherein R2 represents a member selected from the group consisting of a

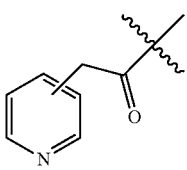

group,
a —CO-pyridyl group, and a —CO—R3 group, wherein R3 represents the residue of any N,N—(C1-C2)-dialkylamino acid or a C4-C6-cycloalkylamino acid

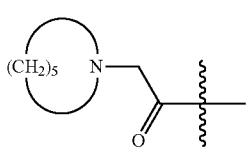

Further L-DOPA prodrugs for use in the present invention, and methods for their synthesis, disclosed in U.S. Pat. Nos. 4,065,566 and 4,035,507 are represented by the formula

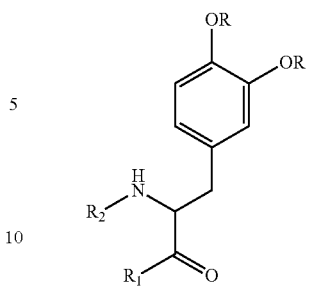

wherein R represents an acyl group; wherein R2 represents a hydrogen atom; and wherein R1 represents a —NHCH(R4)COOR5 group, wherein R4 represents the residue of any naturally occurring amino acid, and wherein R5 represents a member selected from the group consisting of a hydrogen atom, a C1-C5 alkyl group (e.g., methyl, ethyl, propyl, butyl, pentyl), and a C1-C5 alkylaryl group (e.g., —CH$_2$—C$_6$H$_5$, —CH$_2$—CH$_2$—C$_6$H$_5$, etc.), and the HX salts thereof, wherein X is a conventional pharmaceutically acceptable acid addition salt anion (e.g., chloride, bromide, perchlorate, methanesulfonate, succinate, etc.);

Preferred exemplary L-DOPA prodrugs disclosed in U.S. Pat. Nos. 4,065,566 and 4,035,507 include the following:

1. Glycyl-3,4-diacetyloxy-L-phenylalanine and its HX salt, wherein X represents a pharmaceutically acceptable anion.
2. Glycyl-3,4-diacetyloxy-L-phenylalanine-methyl ester and its HX salt, wherein X represents a pharmaceutically acceptable anion.
3. 3,4-diacetyloxy-L-phenylalanyl-glycine and its HX salt, wherein X represents a pharmaceutically acceptable anion.
4. N-nicotinoyl-3,4-dihydroxy-L-phenylalanine and its M salt, wherein M represents an alkali metal.
5. N-nicotinoyl-3,4-diacetyloxy-L-phenylalanine and its M salt, wherein M represents an alkali metal.
6. N-nicotinoyl-3,4-dipivalyloxy-L-phenylalanine and its M salt, wherein M represents an alkali metal.
7. 3,4-diacetyloxy-L-phenylalanyl-glycine and its HX salt, wherein X represents a pharmaceutically acceptable anion.
8. 3,4-diacetyloxy-L-phenylalanyl-glycine-methyl ester and its HX salt, wherein X represents a pharmaceutically acceptable anion.
9. 3,4-diacetyloxy-L-phenylalanyl-glycine-ethyl ester and its HX salt, wherein X represents a pharmaceutically acceptable anion.
10. 3,4-diacetyloxy-L-phenylalanyl-glycine-benzyl ester and its HX salt, wherein X represents a pharmaceutically acceptable anion.
11. 3,4-diacetyloxy-L-phenylalanyl-L-leucine and its HX salt, wherein X represents a pharmaceutically acceptable anion.
12. 3,4-diacetyloxy-L-phenylalanyl-L-leucine-methyl ester and its HX salt, wherein X represents a pharmaceutically acceptable anion.
13. 3,4-diacetyloxy-L-phenylalanyl-L-leucine-ethyl ester and its HX salt, wherein X represents a pharmaceutically acceptable anion.
14. 3,4-diacetyloxy-L-phenylalanyl-L-leucine-benzyl ester and its HX salt, wherein X represents a pharmaceutically acceptable anion.

15. 3,4-diacetyloxy-L-phenylalanyl-L-isoleucine and its HX salt, wherein X represents a pharmaceutically acceptable anion.
16. 3,4-diacetyloxy-L-phenylalanyl-L-isoleucine-methyl ester and its HX salt, wherein X represents a pharmaceutically acceptable anion.
17. 3,4-diacetyloxy-L-phenylalanyl-L-isoleucine-ethyl ester and its HX salt, wherein X represents a pharmaceutically acceptable anion.
18. 3,4-diacetyloxy-L-phenylalanyl-L-isoleucine-benzyl ester and its HX salt, wherein X represents a pharmaceutically acceptable anion.
19. 3,4-diacetyloxy-L-phenylalanyl-phenylalanine and its HX salt, wherein X represents a pharmaceutically acceptable anion.
20. 3,4-diacetyloxy-L-phenylalanyl-phenylalanine-methyl ester and its HX salt, wherein X represents a pharmaceutically acceptable anion.
21. 3,4-diacetyloxy-L-phenylalanyl-phenylalanine-ethyl ester and its HX salt, wherein X represents a pharmaceutically acceptable anion.
22. 3,4-diacetyloxy-L-phenylalanyl-phenylalanine-benzyl ester and its HX salt, wherein X represents a pharmaceutically acceptable anion.
23. Glycyl-3,4-diacetyloxy-L-phenylalanine and its HX salt, wherein X represents a pharmaceutically acceptable anion.
24. Glycyl-3,4-dipivalyloxy-L-phenylalanine and its HX salt, wherein X represents a pharmaceutically acceptable anion.
25. Glycyl-3,4-diacetyloxy-L-phenylalanine-methyl ester and its HX salt, wherein X represents a pharmaceutically acceptable anion.
26. Glycyl-3,4-diacetyloxy-L-phenylalanine-ethyl ester and its HX salt, wherein X represents a pharmaceutically acceptable anion.
27. Glycyl-3,4-diacetyloxy-L-phenylalanine-benzyl ester and its HX salt, wherein X represents a pharmaceutically acceptable anion.
28. L-leucyl-3,4-diacetyloxy-L-phenylalanine and its HX salt, wherein X represents a pharmaceutically acceptable anion.
29. L-leucyl-3,4-diacetyloxy-L-phenylalanine-methyl ester and its HX salt, wherein X represents a pharmaceutically acceptable anion.
30. L-leucyl-3,4-diacetyloxy-L-phenylalanine-ethyl ester and its HX salt, wherein X represents a pharmaceutically acceptable anion.
31. L-leucyl-3,4-diacetyloxy-L-phenylalanine-benzyl ester and its HX salt, wherein X represents a pharmaceutically acceptable anion.
32. L-isoleucyl-3,4-diacetyloxy-L-phenylalanine and its HX salt, wherein X represents a pharmaceutically acceptable anion.
33. L-isoleucyl-3,4-diacetyloxy-L-phenylalanine-methyl ester and its HX salt, wherein X represents a pharmaceutically acceptable anion.
34. L-isoleucyl-3,4-diacetyloxy-L-phenylalanine-ethyl ester and its HX salt, wherein X represents a pharmaceutically acceptable anion.
35. L-isoleucyl-3,4-diacetyloxy-L-phenylalanine-benzyl ester and its HX salt, wherein X represents a pharmaceutically acceptable anion.
36. Phenylalanyl-3,4-diacetyloxy-L-phenylalanine and its HX salt, wherein X represents a pharmaceutically acceptable anion.
37. Phenylalanyl-3,4-diacetyloxy-L-phenylalanine-methyl ester and its HX salt, wherein X represents a pharmaceutically acceptable anion.
38. Phenylalanyl-3,4-diacetyloxy-L-phenylalanine-ethyl ester and its HX salt, wherein X represents a pharmaceutically acceptable anion.
39. Phenylalanyl-3,4-diacetyloxy-L-phenylalanine-benzyl ester and its HX salt, wherein X represents a pharmaceutically acceptable anion.
40. 3,4-diacetyloxy-L-phenylalanyl-3,4-diacetyloxy-L-phenylalanine and its HX salt, wherein X represents a pharmaceutically acceptable anion.
41. 3,4-diacetyloxy-L-phenylalanyl-3,4-diacetyloxy-L-phenylalanine-methyl ester and its HX salt, wherein X represents a pharmaceutically acceptable anion.
42. 3,4-diacetyloxy-L-phenylalanyl-3,4-diacetyloxy-L-phenylalanine-ethyl ester and its HX salt, wherein X represents a pharmaceutically acceptable anion.
43. 3,4-diacetyloxy-L-phenylalanyl-3,4-diacetyloxy-L-phenylalanine-benzyl ester and its HX salt, wherein X represents a pharmaceutically acceptable anion.
44. N—[N,N-dimethylamino]-glycyl-3,4-diacetyloxy-L-phenylalanine and its M salt, wherein M represents an alkali metal.
45. N-nicotinoyl-3,4-dinicotinoyloxy-L-phenylalanine and its M salt, wherein M represents an alkali metal.
46. N-3-pyridylacetyl-3,4-dihydroxy-L-phenylalanine and its M salt, wherein M represents an alkali metal.
47. N-3-pyridylacetyl-3,4-diacetyloxy-L-phenylalanine and its M salt, wherein M represents an alkali metal.
48. 3,4-N,N-dimethylaminoglycyl-L-phenylalanine methylester and its HX salt, wherein X represents a pharmaceutically acceptable anion.
49. N—[N,N-dimethylamino]glycyl-3,4-[N,N-dimethylaminoglycyl]-L-phenylalanine and its M salt, wherein M represents an alkali metal.
50. N—[N,N-diethylaminoglycyl]-3,4-diacetyloxy-L-phenylalanine and its M salt, wherein M represents an alkali metal.

As used herein, the term "alkyl" refers to a saturated aliphatic hydrocarbon including straight chain and branched chain groups. The alkyl group preferably has between 1 and 30 carbon atoms, more preferably between 1 and 20 carbon atoms. While lower alkyls, e.g., of between 1 and 6 carbon atoms may facilitate the formulation of the compounds, higher alkyls provides for enhanced permeability thereof through the BBB.

The alkyl group, according to the present invention, may be substituted or non-substituted. When substituted, the substituent group can be, for example, cycloalkyl, alkenyl, aryl, heteroaryl, heteroalicyclic, hydroxy, alkoxy, aryloxy, thiohydroxy, thioalkoxy, thioaryloxy, halo, carboxy, alkoxycarbonyl, thiocarboxy, carbamyl, and amino, as these terms are defined herein.

As used herein, the term "cycloalkyl" refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. The cycloalkyl group, according to the present invention, may be substituted or non-substituted. When substituted, the substituent group can be, for example, alkyl, cycloalkyl, alkenyl, aryl, heteroaryl, heteroalicyclic, hydroxy, alkoxy, aryloxy, thiohydroxy, thioalkoxy, thioaryloxy, halo, carboxy, alkoxycarbonyl, thiocarboxy, carbamyl, and amino, as these terms are defined herein.

The term "alkenyl" refers to an alkyl group which consists of at least two carbon atoms and at least one carbon-carbon double bond.

The term "alkynyl" refers to an alkyl group which consists of at least two carbon atoms and at least one carbon-carbon triple bond.

As is discussed above, both the alkenyl and the alkynyl groups preferably have between 1 and 30 carbon atoms.

An "aryl" group refers to an all-carbon monocyclic or fused-ring polycyclic (i.e., rings which share adjacent pairs of carbon atoms) group having a completely conjugated pi-electron system. Examples, without limitation, of aryl groups are phenyl, naphthalenyl and anthracenyl. The aryl group, according to the present invention, may be substituted or non-substituted. When substituted, the substituent group can be, for example, alkyl, cycloalkyl, alkenyl, aryl, heteroaryl, heteroalicyclic, hydroxy, alkoxy, aryloxy, thiohydroxy, thioalkoxy, thioaryloxy, halo, carboxy, alkoxycarbonyl, thiocarboxy, carbamyl, and amino, as these terms are defined herein.

The term "C-carboxy" refers to a +C(=O)—OR' group, where R' is hydrogen, alkyl, cycloalkyl, alkenyl, aryl, heteroaryl (bonded through a ring carbon) or heteroalicyclic (bonded through a ring carbon) as defined herein.

The term "O-carboxy" refers to a R'—C(=O)—O— group, where R' is hydrogen, alkyl, cycloalkyl, alkenyl, aryl, heteroaryl (bonded through a ring carbon) or heteroalicyclic (bonded through a ring carbon) as defined herein.

The term "carbonyl" refers to a —C(=O)—R' group, where R' is as defined hereinabove.

The term "thiocarbonyl" refers to a —C(=S)—R' group, where R' is as defined hereinabove.

An "O-carbamyl" group refers to an —OC(=O)—NR'R" group, where R' is as defined hereinabove and R" is as defined for R'.

An "O-thiocarbamyl" group refers to an —OC(=S)—NR'R" group, where R' is and R" are as defined hereinabove.

A "fatty acid acyl" refers to a R'''C(=O)—O— group, where R''' is a saturated or unsaturated hydrocarbon chain having at least 10 carbon atoms.

The term "alkoxy" refers to both an —O-alkyl and an —O-cycloalkyl group, as defined hereinabove. Representative examples of alkoxy groups include methoxy, ethoxy, propoxy and tert-butoxy.

The —O-alkyl and the O-cycloalkyl groups, according to the present invention, may be substituted or non-substituted. When substituted, the substituent group can be, for example, cycloalkyl, alkenyl, aryl, heteroaryl, heteroalicyclic, hydroxy, alkoxy, aryloxy, thiohydroxy, thioalkoxy, thioaryloxy, halo, carboxy, alkoxycarbonyl, thiocarboxy, carbamyl, and amino, as these terms are defined herein.

The term "thioalkoxy" refers to both an —S-alkyl group, and an —S-cycloalkyl group, as defined herein.

The term "hydroxy" refers to an —OH group.

The term "thiohydroxy" refers to an —SH group.

An "aryloxy" group refers to both an —O-aryl and an —O-heteroaryl group, as defined herein.

A "thioaryloxy" group refers to both an —S-aryl and an —S-heteroaryl group, as defined herein.

The term "amino" refers to a —NR'R" group, with R' and R" as defined hereinabove.

The term "alkoxycarbonyl", which is also referred to herein interchangeably as "carbalkoxy", refers to a carboxy group, as defined hereinabove, where R' is not hydrogen.

The term "heteroaryl" group includes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system.

The term "halo" refers to a fluorine, chlorine, bromine or iodine atom.

The term "phosphonyl" describes an —P(=O)(OR')$_2$ group, with R' as defined hereinabove.

In any embodiment of the first or second aspect of the invention, the methods may comprise administering two or more compounds selected from the group consisting of L-DOPA and L-DOPA analogues. In another preferred embodiment, the methods may further comprise administering a further therapeutic compound to the subject, including but not limited to an L-amino acid decarboxylase inhibitor, such as carbidopa or benserazide. Such L-amino acid decarboxylase inhibitors can be used, for example, to increase plasma half-life of L-DOPA and reduce conversion of L-DOPA to dopamine peripherally, which reduces side effects of L-DOPA treatment. In another embodiment, the methods may further comprise administering one or more other compounds useful for treating or limiting development of AMD, including but not limited to anti-angiogenic therapeutics, such as anti-vascular endothelial growth factor (VEGF) agents, including but not limited to VEGF antibodies (or fragments thereof) such as ranibizumab or bevacizumab, or VEGF aptamers, such as pegaptanib. In another embodiment, the L-DOPA or L-DOPA analogues may be present in a more complex mixture, such as in a nutritional supplement containing L-DOPA or L-DOPA analogues.

In a preferred embodiment, any one or more of the L-DOPA and/or L-DOPA analogues described herein may be used in the form of a dietary supplement. Such a supplement may combine any one or more further components that might be beneficial in treating or limiting development of AMD. In one preferred embodiment, L-DOPA and/or an L-DOPA analogue are combined with a combination of vitamin C source, vitamin E source, Vitamin A source, zinc source, and, and copper source, disclosed in U.S. Pat. No. 6,660,297 as useful in treating AMD; U.S. Pat. No. 6,660,297 is incorporated by reference herein in its entirety. Any suitable amount of each of these additional components can be used in combination with L-DOPA and/or L-DOPA analogues in carrying out the methods of the invention. In a further preferred embodiment, this combination may further comprise lutein and/or zeaxanthin in an amount suitable to provide further protective retinal effects, preferably between 1 mg and 100 mg; between 1 mg and 50 mg, between 2 mg and 25 mg, or between 2 mg and 10 mg per day. In a further preferred embodiment of any of the above preferred embodiments, this combination may further comprise docosahexaenoic acid (DHA) and/or eicosapentaenoic acid (EPA) in an amount suitable to provide further protective retinal effects, preferably between 250 mg and 1000 mg; between 300 mg and 750 mg, between 350 mg and 750 mg, or between 350 mg and 650 mg per day.

Ascorbic acid is the preferred source of vitamin C, although other sources such as for example sodium ascorbate could alternatively be used.

Dl-alpha tocopheryl acetate is the preferred source of vitamin E, although other sources of vitamin E, such as for example trimethyl tocopheryl acetate and/or vitamin E succinate, may be used in the alternative.

Beta-carotene is preferred in the subject composition due to its ready commercial availability although alternative carotenoid proforms of vitamin A could likewise be used.

Zinc is preferred in the form of zinc oxide in subject tablets due to the fact zinc oxide provides the most concentrated form for elemental zinc and is well tolerated in the digestive system. However, other forms of zinc such as for example zinc gluconate may alternatively be used or be used in combination with zinc oxide in the subject composition.

Copper in the form of cupric oxide is preferred in the subject tablets to help prevent zinc induced copper deficiency anemia, although other forms of copper such as for example copper gluconate may alternatively be used or used in combination with cupric oxide in the subject composition.

In a preferred embodiment, the amounts of each of these other components (on a per day basis) is as follows:

between 450 mg and 600 mg vitamin C (approximately 7-10 times the recommended daily allowance (RDA))

between 400 IU and 540 IU vitamin E (approximately 13-18 times the RDA);

between 17.2 mg and 28 mg beta carotene (approximately 6-10 times the RDA of vitamin A; beta carotene is a prodrug of vitamin A);

between 68 mg and 100 mg zinc (approximately 4-7 times the RDA for zinc); and between 1.6 mg and 2.4 mg copper.

In a further preferred embodiment, the amounts of each of these other components (on a per day basis) is as follows:

500 mg Vitamin C;

400 IU Vitamin E;

0 mg or 15 mg beta carotene;

25 mg or 80 mg zinc oxide; and 2 mg cupric oxide.

In a further preferred embodiment, that may be combined with any other embodiments herein, other ingredients believed to be of benefit in maintaining eye health may likewise be combined with L-DOPA and/or L-DOPA analogues, including but not limited to lutein and/or zeaxanthin in an amount suitable to provide further protective retinal effects, preferably between 1 mg and 100 mg; between 1 mg and 50 mg, between 2 mg and 25 mg, or between 2 mg and 10 mg per day; and/or docosahexaenoic acid (DHA) and/or eicosapentaenoic acid (EPA) in an amount suitable to provide further protective retinal effects, preferably between 250 mg and 1000 mg; between 300 mg and 750 mg, between 350 mg and 750 mg, or between 350 mg and 650 mg per day. Further examples of additional compounds that may optionally be used include but are not limited to alpha-lipoic acid and, phenolic compounds such as for example but not limited to oligomeric proanthocyanidins, anthocyanosides and combinations thereof.

L-DOPA and/or L-DOPA analogues can be administered individually or in combination, usually in the form of a pharmaceutical composition. Such compositions are prepared in a manner well known in the pharmaceutical art. L-DOPA and/or L-DOPA analogues can be administered as the sole active pharmaceutical agent, or they can be used in combination with one or more other compounds useful for carrying out the methods of the invention, including but not limited to an anti-angiogenic therapeutics such as VEG-F, and L-amino acid decarboxylase inhibitors, such as carbidopa and benserazide. When administered as a combination, combination can be formulated as separate compositions that are given at the same time or different times, or can be given as a single composition.

The L-DOPA and/or L-DOPA analogues may be made up in a solid form (including granules, powders or suppositories) or in a liquid form (e.g., solutions, suspensions, or emulsions). The L-DOPA and/or L-DOPA analogues may be applied in a variety of solutions and may be subjected to conventional pharmaceutical operations such as sterilization and/or may contain conventional adjuvants, such as preservatives, stabilizers, wetting agents, emulsifiers, buffers etc.

The L-DOPA and/or L-DOPA analogues may be administered by any suitable route, including but not limited to oral, topical (including but not limited to eye drops and ophthalmic ointments), parenteral, intranasal, pulmonary, or rectal in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like.

In addition, there is provided a pharmaceutical formulation comprising a compound of the invention and a pharmaceutically acceptable carrier. L-DOPA and/or L-DOPA analogues may be present in association with one or more non-toxic pharmaceutically acceptable carriers and/or diluents and/or adjuvants, and if desired other active ingredients. The pharmaceutical compositions containing L-DOPA and/or L-DOPA analogues may be in a form suitable for oral use, for example, as tablets, troches, lozenges, aqueous or oily suspensions, dispersible powders or granules, emulsion, hard or soft capsules, or syrups or elixirs.

Eye drops can be prepared using any technique in the art, including but not limited to using a tonicity agent such as sodium chloride or concentrated glycerin, a buffer such as sodium phosphate or sodium acetate, a surfactant such as polyoxyethylene sorbitan monooleate, polyoxyl 40 stearate or polyoxyethylene hydrogenated castor oil, a stabilizer such as sodium citrate or sodium edetate, a preservative such as benzalkonium chloride or paraben as needed. The pH of the eye drops is preferably in the range of from 4 to 8. Ophthalmic ointments can be prepared with a generally used base such as white soft paraffin or liquid paraffin.

L-DOPA and/or L-DOPA analogues intended for oral use may be prepared according to any method known to the art for the manufacture of pharmaceutical compositions and such compositions may contain one or more agents selected from the group consisting of sweetening agents, flavoring agents, coloring agents and preservative agents in order to provide palatable preparations. Tablets contain the L-DOPA and/or L-DOPA analogues in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the L-DOPA and/or L-DOPA analogue is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the L-DOPA and/or L-DOPA analogues in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the L-DOPA and/or L-DOPA analogues in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions for use in the methods of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Specific methods for intranasal administration of L-DOPA and L-DOPA analogues are known in the art; see, for example, Kao et al., Pharmaceutical Research 17(8):978-984 (2000).

The dosage range depends on the choice of the compound, the route of administration, the nature of the formulation, the nature of the subject's condition, and the judgment of the attending practitioner. For example, oral administration would be expected to require higher dosages than administration by intravenous injection. Variations in these dosage levels can be adjusted using standard empirical routines for optimization, as is well understood in the art. In certain embodiments, L-DOPA and/or L-DOPAS analogues can be administered at dosages of between 10 mg/day and 1500 mg/day; in various preferred embodiments administration can be between 20 mg and 1200 mg/day, 50 mg and 1000 mg/day, 100 mg and 500 mg/day, and 200 mg and 400 mg/day.

Pharmaceutical compositions containing the compounds described herein are administered to an individual in need thereof. In a preferred embodiment, the subject is a mammal; in a more preferred embodiment, the subject is a human. In therapeutic applications, compositions are administered in an amount sufficient to carry out the methods of the invention. Amounts effective for these uses depend on factors including, but not limited to, the nature of the compound (specific activity, etc.), the mute of administration, the stage and severity of the disorder, the weight and general state of health of the subject, and the judgment of the prescribing physician. The active compounds are effective over a wide dosage range. However, it will be understood that the amount of the compound actually administered will be determined by a physician, in the light of the above relevant circumstances. Therefore, the above dosage ranges are not intended to limit the scope of the invention in any way.

In a third aspect, the present invention provides compositions comprising:

(a) an amount effective of L-DOPA or an L-DOPA analogue for treating or limiting development of AMD; and (b) an amount effective for treating or limiting development of AMD of a composition comprising a source of vitamin C, a source of vitamin E, a source of vitamin A, a source of zinc, and a source of copper.

The amount of L-DOPA and/or L-DOPAS analogues in the compositions is suitable to provide for administration at dosages of between 10 mg/day and 1500 mg/day; in various preferred embodiments administration can be between 20 mg and 1200 mg/day, 50 mg and 1000 mg/day, 100 mg and 500 mg/day, and 200 mg and 400 mg/day.

Ascorbic acid is the preferred source of vitamin C in the subject tablets, although other sources such as for example sodium ascorbate could alternatively be used. Dl-alpha tocopheryl acetate is the preferred source of vitamin E in the subject tablets although other sources of vitamin E, such as for example trimethyl tocopheryl acetate and/or vitamin E succinate, may be used in the alternative. Beta-carotene is preferred in the subject composition due to its ready commercial availability although alternative carotenoid proforms of vitamin A could likewise be used. Zinc is preferred in the form of zinc oxide in subject tablets due to the fact zinc oxide provides the most concentrated form for elemental zinc and is well tolerated in the digestive system. However, other forms of zinc such as for example zinc gluconate may alternatively be used or be used in combination with zinc oxide in the subject composition. Copper in the form of cupric oxide is preferred in the subject tablets to help prevent zinc induced copper deficiency anemia, although other forms of copper such as for example copper gluconate may alternatively be used or used in combination with cupric oxide in the subject composition.

In one preferred embodiment of this third aspect of the invention, composition "b" provides a formulation suitable to permit ingestion of the following amounts of each component:

Ascorbic acid: at least 450 mg;
dl-alpha tocopheryl acetate: 400 IU;
beta carotene: 17.2 mg;
zinc oxide: 68 mg; and
cupric oxide: 1.6 mg.

In one preferred embodiment of this third aspect of the invention, composition "b" provides a formulation suitable to permit ingestion of the following amounts of each component:

500 mg Vitamin C;
400 IU Vitamin E;
0 mg or 15 mg beta carotene;
25 mg or 80 mg zinc oxide; and
2 mg cupric oxide.

The preferred daily dosage of the subject composition as specified above may be administered in the form of 1, 2, 3, 4, or more dosage forms according to any suitable route of administration as disclosed above. In preferred embodiments, the dosage form is an oral or topical dosage form, according to any embodiment of such dosage forms described herein. In another preferred embodiment the daily dosage of the subject composition is provided in the form of one dosage form taken twice daily, for a total of two dosage forms a day, or in the form of two dosage forms taken twice daily, for a total of four dosage forms a day. Compared to taking the total daily dose once a day, twice daily dosing of half the total daily dose in one or more dosage forms per dose provides improved absorption and better maintenance of blood levels of the essential ingredients. Accordingly, if two dosage forms of the preferred formulation of the subject composition are to be ingested each day, each dosage form is formulated to preferably provide not less than approximately 225 mg ascorbic acid, approximately 200 IU dl-alpha tocopheryl acetate, approximately 8.6 mg beta-carotene, approximately 34 mg zinc oxide and approximately 0.8 mg cupric oxide upon oral administration. If four tablets of the preferred formulation of the subject composition are to be ingested each day, each tablet is formulated to preferably provide not less than approximately 112.5 mg ascorbic acid, approximately 100 IU dl-alpha tocopheryl acetate, approximately 4.3 mg beta-carotene, approximately 17 mg zinc oxide, approximately 0.4 mg cupric oxide, and between 5 mg and 750 mg or L-DOPA and/or L-DOPA analogues.

In another preferred embodiment, the compositions comprise
(a) between 5 mg and 1500 mg L-DOPA or L-DOPA analogue;
(b) between 450 mg and 600 mg vitamin C (approximately 7-10 times the recommended daily allowance (RDA))
(c) between 400 IU and 540 IU vitamin E (approximately 13-18 times the RDA);
(d) between 17.2 mg and 28 mg beta carotene (approximately 6-10 times the RDA of vitamin A; beta carotene is a prodrug of vitamin A);
(e) between 68 mg and 100 mg of zinc (approximately 4-7 times the RDA for zinc); and
(f) at least 1.6 mg of copper.

In various preferred embodiments, the composition may comprise between 10 mg and 1200 mg; between 25 mg and 1000 mg; between 50 mg and 500 mg, or between 100 mg and 400 mg L-DOPA or L-DOPA analogue.

In a further preferred embodiment, that may be combined with any other embodiments herein, other ingredients believed to be of benefit in maintaining eye health may likewise be combined with L-DOPA and/or L-DOPA analogues, including but not limited to lutein and/or zeaxanthin in an amount suitable to provide further protective retinal effects, preferably between 1 mg and 100 mg; between 1 mg and 50 mg, between 2 mg and 25 mg, or between 2 mg and 10 mg per day; and/or docosahexaenoic acid (DHA) and/or eicosapentaenoic acid (EPA) in an amount suitable to provide further protective retinal effects, preferably between 250 mg and 1000 mg; between 300 mg and 750 mg, between 350 mg and 750 mg, or between 350 mg and 650 mg per day. The amounts necessary in any particular dosage form to provide the recited amounts can be determined by one of skill in the art based on the teachings herein and the number of dosage forms to be administered per day.

In a fourth aspect, the present invention provides in vitro methods for identifying compounds to treat AMD, comprising contacting cells with a test compound, wherein the cells comprise:

(a) a first cell population expressing OA1; and, optionally,
(b) a second cell population not expressing OA1; and
(c) identifying as positive test compounds those test compounds that increase one or both of
  (i) pigment epithelium-derived factor (PEDF) expression in the first cell population relative to one or both (A) PEDF expression in the first population of cells not contacted with the test compound, and (B) the second cell population, and
  (ii) intracellular calcium concentration in the first cell population relative to one or both (A) intracellular calcium concentration in the first population of cells not contacted with the test compound, and (B) the second cell population
wherein the positive test compounds are candidate compounds for treating and/or limiting development of AMD.

As described above, human OA1 (SEQ ID NO:1-2 NP 000264.1) is a G-protein coupled receptor and the inventors have herein identified L-DOPA as an OA1 ligand. As disclosed in more detail below, the inventor has discovered the existence of an autocrine loop between OA1 and tyrosinase linked through L-DOPA, and this loop includes the secretion of at least one very potent retinal neurotrophic factor (PEDF) as well as an increase in intracellular calcium concentration. OA1 is a selective L-DOPA receptor whose downstream effects govern spatial patterning of the developing retina. Thus, test compounds that selectively up-regulate PEDF expression and/or intracellular calcium concentration via stimulation of the OA1 pathway are candidate compounds for treating and/or limiting development of AMD. The methods of this aspect of the invention can be carried out with any OA1 homologue of, including but not limited to:

Mouse: SEQ ID NO:3-4 (NM_010951);
*Xenopus tropicalis*: SEQ ID NOS:5-6 (NM_001011018);
Cow: SEQ ID NOS:7-8 (XM_001506318);
Rat: SEQ ID NOS: 9-10 (NM_001106958);
Platypus: SEQ ID NOS: 11-12 (XM_001506318);
*Xenopus laevis*: SEQ ID NOS: 13-14 (NM_001096842)

Chicken: SEQ ID NOS:15-16 (XM_416848);
Zebrafish: SEQ ID NOS: 17-18 (NM_200822);
Chimpanzee: SEQ ID NO: 19 (XR_025625);
Rhesus monkey: SEQ ID NOS:21-22 (XM_001090139; and
Macaque: SEQ ID NO: 23 (BV209253).

PEDF is pigment epithelium-derived factor (Exp Eye Res 53: 411-414), and is a known neurotrophic factor with the potential to alter neurosensory retina development, and to inhibit blood vessel growth. The methods of this aspect of the invention can be carried out with any PEDF homologue of, including but not limited to:

preferably 10 second and 30 minutes, 10 seconds and 10 minutes, and 10 seconds and 5 minutes. 10 seconds and 1 minutes, and 10 seconds and 30 seconds. In various embodiments, measurement of PEDF expression can range between 1 minute and 72 hours, with analysis of PEDF secretion requiring later measurements than analysis of PEDF mRNA expression, PEDF intracellular protein expression, or expression of detectable signals driven by the PEDF promoter.

Any suitable cell culture conditions can be used as appropriate for a given assay. In one preferred embodiment, the contacting occurs in cell culture medium that has either a very low concentration of tyrosine (for example, between 0.1 um and 10 um tyrosine) or no tyrosine, to reduce its production of endogenous L-DOPA in the cells, and to maintain the amount of OA1 present at the cell surface (since OA1 internalizes to the endosomes upon ligand binding). In one preferred embodiment, cells are cultured prior to test compound contacting in low tyrosine medium to maximize OA1 expression and localization at the cell surface, followed by plating into tyrosine-free media for contacting with the test compounds. In another preferred embodiment, contacting occurs in low tyrosine medium. In another preferred embodiment, which can be combined with other embodiments disclosed above, the culture media includes a tyrosinase inhibitor, including but not limited to phenylthiourea, to limit cell production of L-DOPA from tyrosine. This embodiment is particularly preferred when using pigmented cells.

In another preferred embodiment, the method may further comprise use of one or more of L-DOPA, tyrosine, and dopamine as competitors for binding to OA1. This embodiment may be carried out after identifying a test compound as an OA1 ligand, or it may be carried out in an initial screen of test compounds for binding to OA1. As shown in the examples below, at concentrations of 1 mM and above, tyrosine and dopamine can compete with L-DOPA for binding to OA1. Thus, competitive assays using tyrosine and/or dopamine at concentrations between 1 mM and 100 mM, preferably between 1 mM and 50 mM or between 1 mM and 25 mM, can be used to further verify that the test compounds are operating via the OA1 pathway, and to measure the ability of tyrosine and dopamine to displace positive test compound binding to OA1 as compared to displacement of L-DOPA. Similarly, competitive binding compared to L-DOPA (at similar molarity to the test compounds being tested) can help identify those compounds with increased avidity for OA1 compared to L-DOPA.

Any suitable test compounds can be assessed using the methods of the fourth and fifth aspects (see below) of the invention, including small molecules, polypeptides, and nucleic acids. When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with standard deprotecting, neutralization, coupling and wash protocols, or standard base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art.

In addition, the polypeptides can be synthesized with other Nα-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988).

When the test compounds comprise nucleic acid sequences, such nucleic acids may be chemically synthesized or recombinantly expressed as well. Recombinant expression techniques are well known to those in the art (See, for example, Sambrook, et al., 1989, supra). The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell. For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other then polypeptides, antibodies, or nucleic acids, such compounds can be made by any of the variety of methods in the art for conducting organic chemical synthesis.

Test compounds identified as increasing the expression of PEDF and/or intracellular calcium concentration in the first cell population relative to the second cell population, can be further assessed for use as a candidate compound for treating or limiting development of AMD using any further technique, including but not limited to the in vivo methods of the fourth aspect of the invention, described below. In one preferred embodiment, the method may further comprise re-testing the positive test compounds in the assay in the presence of competitive amounts of tyrosine and/or dopamine, as described above.

In a fifth aspect, the present invention provides methods for identifying compounds to treat AMD, comprising (a) administering a test compound to a tyrosinase deficient pregnant female non-human mammal, wherein the test compound is administered during embryonic photoreceptor and/or retinal ganglion development; and (b) comparing an effect of the test compound on photoreceptor and/or retinal ganglion development in the embryo or post-natal non-human mammal, to photoreceptor and/or retinal ganglion development in an embryo or post-natal non-human mammal not administered the test compound, wherein those test compounds that increase photoreceptor and/or retinal ganglion development are candidate compounds for treating and/or limiting development of AMD.

The inventor has determined that OA1 signaling can be used to rescue photoreceptor and ganglion cell development in tyrosinase-deficient animals, and in the process establish the neurotrophic effect of OA1 signaling. Thus, compounds that rescue neurosensory retinal development through OA1 signaling are good candidates for AMD treatment. The present invention provides the first establishment of such an animal model for AMD drug screening.

As described in more detail herein, tyrosinase acts on tyrosine to create L-DOPA. Thus, a tyrosinase deficient mammal does not produce L-DOPA, permitting the use of such mammals to identify activators of OA1 (via rescue of retinal development and/or increased PEDF expression) in the absence of endogenous L-DOPA. As used herein, a "tyrosinase deficient" means that the pregnant female non-human mammal does not produce adequate amounts of tyrosinase to create L-DOPA in amounts adequate for normal pigment formation. In one preferred embodiment, the pregnant non-human mammal is a knockout animal (deleted for portion or all of the tyrosinase gene, or have naturally occurring mutations in the tyrosinse gene or accessory genes that control, activate, or traffic tyrosinase to the melanosome) with no ability to express or traffic functional tyrosinase. Such tyrosinase knockouts are known in the art and are commercially available (Lexicon Pharmaceuticals, Jackson Laboratories, Taconic Farms. In other embodiments, the tyrosinase deficiency may be transiently induced by methods known in the art including, but not limited to, administering siRNAs targeting tyrosinase, tyrosinase antibody/aptamer treatment, etc.

The non-human mammal can be any in which tyrosinase-deficient (retinal albino) females can be obtained, which includes all mammals. In various preferred embodiments, the non-human mammal is mouse, pig, apes, and rat.

In one preferred embodiment, administration of test compound is continued during the post-natal period of photoreceptor and/or retinal ganglion development. The embryonic and post-natal photoreceptor and/or retinal ganglion development pathways in various non-human mammals is well understood by those of skill in the art. In one exemplary embodiment, mouse embryonic photoreceptor and retinal ganglion development begins on embryonic day 10 (E10) and retinal development is complete by postnatal day 14 (P14) when the pups eyes are open. Thus, in various embodiments, test compounds are first administered at about day E7, E8, E9, or E10 (to facilitate its presence at the earliest stage of ocular development) and administration can continue as desired for a given assay between day P1, P2, P3, P4, P5, P6, P7, P8, P9, P10, P11, P12, P13, and day P14 or later as desired (up to one year post-natal). As will be understood by those of skill in the art, administration will be to the pregnant female mother during the embryonic phase and to the pup postnatally. In another embodiment, pigmented cell development begins in earnest at approximately day E10.5 (when OA1 and tyrosinase appear), and thus in one embodiment, administration of test compound may begin on about day E10, E10.5, or E11 and continue as desired up to about day P1, P2, P3, P4, P5, P6, P7, P8, P9, P10, P11, P12, P13, P14 or later as desired. In another embodiment, test compound administration may be limited to between day E7 and E10 or E11. In a further embodiment, retinal ganglion development begins in earnest at about day E12, and thus in one embodiment, administration of test compound may begin on about day E12 or E13 and continue as desired up to about day P1, P2, P3, P4, P5, P6, P7, P8, P9, P10, P11, P12, P13, P14 or later as desired. In another embodiment, test compound administration may be limited to between day E7 and E12 or E13. In a most preferred embodiment test compounds are first administered daily from day E7 until day P14. As will be understood by those of skill in the art, the exact timing of test compound administration will depend on the goals of the particular assay and can be determined by one of skill in the art based on the teachings herein.

The test compounds may be administered by any route suitable for use with experimental animals, including those routes of administration disclosed above for therapeutic administration of L-DOPA or L-DOPA analogues. In a preferred embodiment, the test compounds are administered in the animal's drinking water, parenterally (as discussed above) or topically (for example, in eye drops or ophthalmic ointments). Frequency of test compound administration can be as often as appropriate for a given assay; in a preferred embodiment, test compound is administered daily throughout the desired course of treatment; in other embodiments, administration is every second, third, fourth, or fifth day during the course of treatment; the frequency of administration can be determined by one of skill in the art based on the teachings herein and the specific goals of a given assay.

As used herein, an "increase in photoreceptor and/or retinal ganglion development" is any increase in photoreceptor and/or retinal ganglion development in test-compound treated vs. non-treated embryos/animals. The method does not require a specific amount of increase in photoreceptor and/or retinal ganglion development over control, so long as the compound(s) promotes an increase in photoreceptor and/or retinal ganglion development above that seen in the control. In a preferred embodiment, the increase is a statistically significant increase as measured by standard statistical measurements. In one embodiment, animals are euthanized at the appropriate time point, and retinal ganglion cells and/or photoreceptors are counted using standard methods in the art, including but not limited to those disclosed in the examples below.

Test compounds identified as increasing photoreceptor and/or retinal ganglion development, can be further assessed for use as a candidate compound for treating or limiting development of AMD using any further technique, including but not limited to re-testing the positive test compounds using the in vitro methods disclosed in the third aspect of the invention in the presence of competitive amounts of tyrosine and/or dopamine. As shown in the examples below, at concentrations of 1 mM and above, tyrosine and dopamine can compete with L-DOPA for binding to OA1. Thus, competitive assays using tyrosine and/or dopamine at concentrations between 1 mM and 100 mM, preferably between 1 mM and 50 mM or between 1 mM and 25 mM, can be used to further verify that the test compounds are operating via the OA1 pathway, and to measure the ability of tyrosine and dopamine to displace positive test compound binding to OA1 as compared to displacement of L-DOPA.

EXAMPLES

L-DOPA is an Endogenous Ligand for OA1

Background:

Albinism is a genetic defect characterized by a loss of pigmentation. The neurosensory retina, which is not pigmented, exhibits pathologic changes secondary to the loss of pigmentation in the retina pigment epithelium (RPE). How the loss of pigmentation in the RPE causes developmental defects in the adjacent neurosensory retina has not been determined, but offers a unique opportunity to investigate the interactions between these two important tissues. One of the genes which causes albinism encodes for an orphan GPCR (OA1) expressed only in pigmented cells, including the RPE.

Methodology/Principle Findings:

The function and signaling of OA1 was investigated in RPE and transfected cell lines. The results indicate that OA1 is a selective L-DOPA receptor, with no measurable second messenger activity from two closely related compounds, tyrosine and dopamine. Radiolabeled ligand binding confirmed that OA1 exhibited a single, saturable binding site for L-DOPA. Dopamine competed with L-DOPA for the single OA1 binding site suggesting it could function as an OA1 antagonist. OA1 response to L-DOPA was defined by several common measures of GPCR activation including influx of intracellular calcium and recruitment of β-arrestin. Further, inhibition of tyrosinase, the enzyme that makes L-DOPA, resulted in decreased PEDF secretion by RPE. Further, stimulation of OA1 in RPE with L-DOPA resulted in increased PEDF secretion.

Conclusions/Significance:

Taken together the results illustrate an autocrine loop between OA1 and tyrosinase linked through L-DOPA, and this loop includes the secretion of at least one very potent retinal neurotrophic factor. OA1 is a selective L-DOPA receptor whose downstream effects govern spatial patterning of the developing retina. The results suggest that the retinal consequences of albinism caused by changes in melanin synthetic machinery may be treated by L-DOPA supplementation.

Introduction:

Albinism is a group of inherited genetic diseases in which there is a variable loss of pigmentation in the eye, hair or skin. When the eye is affected, there are significant alterations in neurosensory retina development that lead to low vision [1-8]. There are two broad classes of albinism, ocular-cutaneous albinism (OCA) and ocular albinism (OA). OCA occurs when all pigmented tissues exhibit hypopigmentation and involves genetic mutations that result in defects in the melanin synthetic machinery [3,7-9]. OA occurs when cutaneous tissues pigment normally, but the ocular tissues are hypopigmented [10,11]. Since the same proteins produce pigment in all tissues, OA most likely results from lack of expression of the melanogenic enzymes in ocular tissue rather than an inability to synthesize melanin because the other tissues pigment normally.

OA can be linked to at least one gene, Oa1, which is found on the X chromosome. Oa1 encodes a 404 amino acid protein likely to be an orphan G-protein coupled receptor (GPCR), OA1 (Genbank GPR143) [12,13] based upon sequence analysis [14]. Schiaffino et al. has demonstrated that OA1 associates with several $G_\alpha$ subunits as well as $G_\beta$ adding further evidence that OA1 is a GPCR [14,15]. Indeed, Innamorati et. al. used a combinatorial expression strategy to illustrate GPCR-like activity from OA1, as well as β-arrestin association, even in the absence of a ligand [16]. This work suggested that OA1 could signal through a Gαq subunit through phospholipase C and inositol triphosphate second messengers. In a yeast based expression system, Staleva and Orlow have demonstrated GPCR signaling from OA1 that appeared to be activated by a component in the melanosomal compartment [17]. Despite the significant amount of circumstantial evidence that OA1 is a GPCR, confirmation is lacking because no ligand has been identified. Other data has called into question the idea that OA1 is a GPCR. For example, the localization of OA1 as a fully intracellular protein is not typical of GPCRs and suggests that it would be a unique member of the family [14]. OA1 is primarily localized to the endolysosomal compartment [14,15,18-21] and melanosomes [11,14,22] rather than the cell surface.

In this study the function of OA1 as a potential GPCR was investigated, based on the hypothesis that the endosomal localization of OA1 in cultured cells was due to internalization of OA1 in response to an agent in the culture medium. Further, a ligand for OA1 was sought based on the observation that all forms OCA and OA appear to have the same retinal phenotype, indicating that tyrosinase activity and OA1 signaling are coupled upstream of retinal development. Thus, tests on whether tyrosinase activity produces the ligand for OA1 were carried out. A by-product of melanin synthesis is L-DOPA, which is released to the retina during melanin synthesis in the RPE at a critical time in retinal development [23,24]. The data suggest that OA1 is a highly selective L-DOPA receptor, and that L-DOPA causes OA1 signaling with the downstream effect of neurotrophic factor secretion by RPE. Thus, the first evidence is presented of a ligand for OA1, and provide a mechanism through which either tyrosinase or OA1 deficiency results in changes to retinal development.

Results:

Cell Surface Localization of OA1.

OA1 has previously been localized in pigment granules in situ [22], however, using transfected cells of various types, OA1 also has been localized to both the plasma membrane [16,17] and the endosomal fraction of cultured cells [14,16-18,20,21]. The investigation began by determining where OA1 resides in the human tissue using cell surface biotinylation/western blot strategies. In the human eye, OA1 was present on the apical cell surface of the RPE in situ (FIG. 1A). Quantification of cell surface, biotinylated OA1 in five human eyes indicated that at least 3.5+/−0.7% of the total OA1 resided on the apical cell surface of RPE in situ. Access to the biotinylation reagent using eye cup preparations is restricted to the apical surface, so the polarity of OA1 in the epithelium cannot be determined. Further, the total cell surface OA1 is likely underestimated because of the lack of access to the basal cell surface. Blots were also probed with antibodies against actin as a control to verify that cytoplasmic proteins were not biotinylated. In each experiment actin was only found in the unbound fraction.

Others have reported that recombinant OA1 and OA1-GFP is almost exclusively localized to the endosomal compartment in cultured cells [14,15,17,18,20-22]. However, when overexpressed [16], or when endocytosis is inhibited [17], OA1 accumulates at the cell surface. The observation that OA1 protein is present on the apical surface of RPE in situ led us to explore the issue further.

Effects of Tyrosine on OA1 Expression and Distribution

Endosomal localization of GPCRs occurs normally after exposure to a ligand. Therefore, it was investigated whether a ligand for the receptor was present in the standard incubation medium that could drive internalization of OA1. Since the standard culture medium contains 500 μM tyrosine, and tyrosine is the starting material for pigment synthesis, the effect of tyrosine on receptor distribution was evaluated. To test whether tyrosine affected OA1 distribution in cultured cells DMEM was formulated without tyrosine, and dialyzed fetal bovine serum was used. In the presence of tyrosine-free medium, OA1 was detected on the plasma membrane of cultured RPE cells both in the absence (not shown), and in medium containing low concentrations of tyrosine (1 μM, FIG. 1B). Averaged over five experiments, 4.5+/−1% of total OA1 protein was observed on the surface of cultured RPE maintained in 1 μM tyrosine, similar to what was observed for RPE in situ. In all experiments actin was observed in the unbound protein fraction, demonstrating the absence of any cytoplasmic protein in the cell surface assay. Similarly, OA1-GFP expressed in COS illustrated a cell surface expression that was tyrosine sensitive (FIG. 1C). Quantification of six such experiments indicated significant variability in the amount of OA1 found at the cell surface using transient transfections. The range of OA1 in the bound fraction of transfected cells maintained in 1 μM tyrosine ranged between 5-40%, unlike the results with the endogenous OA1 protein that were reproducibly ~5%.

Not only was the distribution of OA1 in transfected cells sensitive to tyrosine levels in the medium, total OA1-GFP expression was increased 5-fold in cells maintained in 1 μM tyrosine. To verify that this difference related to OA1 expression rather than cell number, actin expression was evaluated from the paired samples. The data (FIG. 1D) presented as optical density units indicate no difference in actin. The amount of cell surface OA1 between the normal and low tyrosine groups was also compared. Importantly, in the five RPE experiments and six OA1-GFP in COS experiments, OA1 in the plasma membrane fraction of cells in standard medium was not reproducibly detected, similar to that found by others.

The distribution of OA1 in RPE cells also was evaluated by confocal microscopy. OA1 has previously been characterized as an endosomal protein in cultured RPE cells as shown in (FIG. 1E). In contrast, the distribution of OA1 in low tyrosine medium was diffuse on the plasma membrane of cultured RPE cells, with little endosomal accumulation (FIG. 1F), an observation consistent with the results obtained using biochemical methods.

L-DOPA as a Natural Agonist for OA1.

Figure 2:
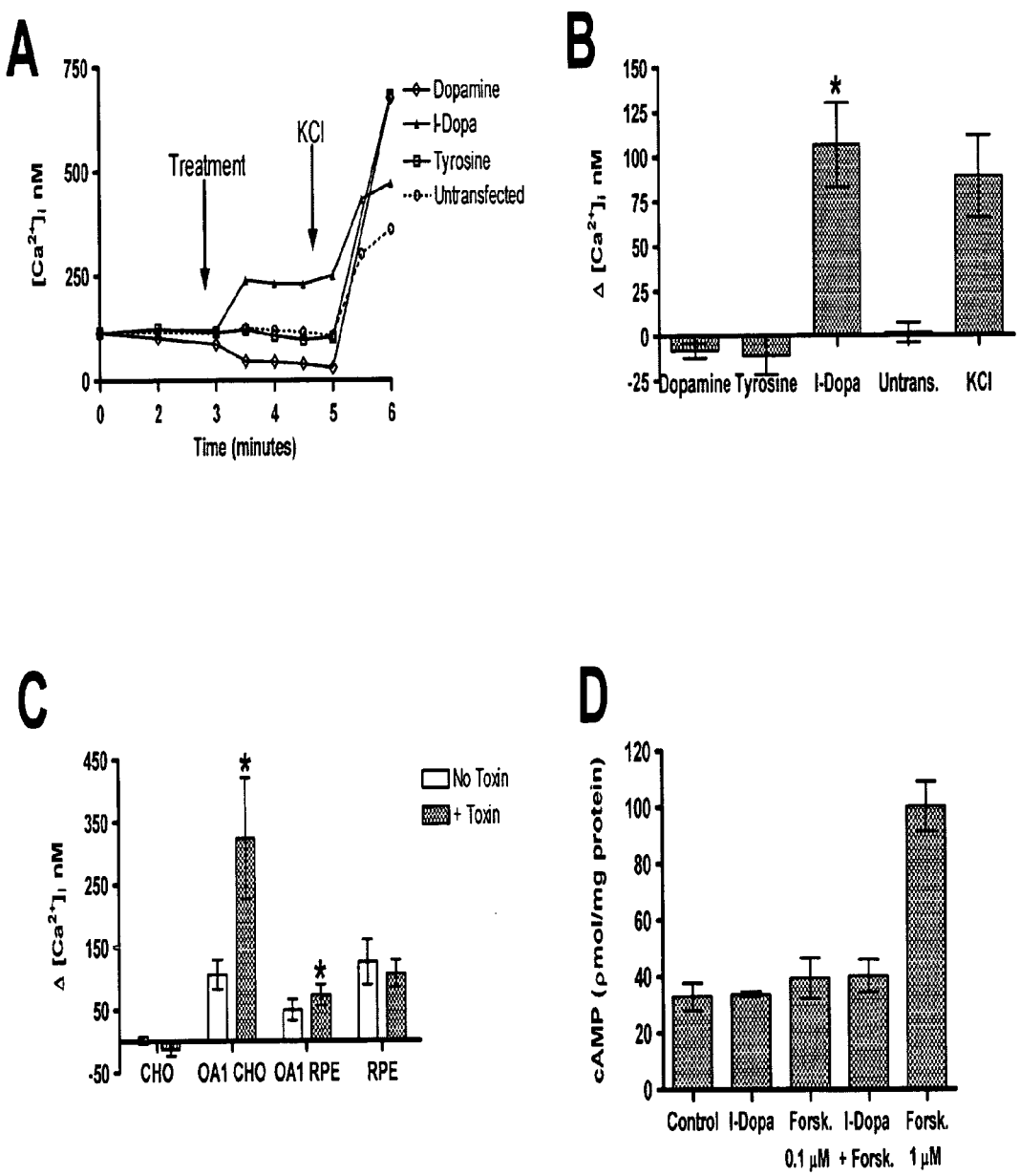
FIG. 2(*a*) Representative traces of $[Ca^{2+}]i$ during the time course of the standard experimental protocol in transfected and untransfected CHO cells. After establishment of a stable baseline for 3 minutes, the test agent was added at 1 µM. At 5 minutes, KCl was added to serve as a control that the cells were Fura-2 loaded and patent. Identical protocols were performed for both transfected cells and paired untransfected cells.

Tyrosinase function in melanogenesis begins with its activity on tyrosine to create L-DOPA, followed by a second reaction to create dopaquinone that leads to pigment formation [25]. Of the intermediates between tyrosine and melanin, L-DOPA has the greatest half-life, and L-DOPA is released into the subretinal space apical to the RPE when melanin synthesis occurs [23,24]. L-DOPA is also the precursor to dopamine, a neurotransmitter produced by dopaneurgic neurons from tyrosine. The release of calcium from intracellular stores is a common downstream effect of GPCR activation by a ligand. Since the expression of OA1 on the cell surface appears to be sensitive to tyrosine, it was examined whether tyrosine, or its metabolites L-DOPA and dopamine, could stimulate influx of $Ca^{2+}$ into the cytoplasm in an OA1-dependent manner. CHO cells were transfected with an OA1 expression vector then maintained in DMEM containing 1 µM tyrosine for 48 hours followed by tyrosine-free DMEM for 24 hours to facilitate cell surface expression of OA1. Intracellular $Ca^{2+}$ was evaluated using Fura-2, and $[Ca^{+2}]i$ was determined by ratiometric imaging [26]. In the absence of any ligand, $[Ca^{2+}]i$ was not significantly different between transfected and untransfected cells (FIG. 2). Tyrosine and several tyrosine metabolites were tested at 1 µM for an effect on $[Ca^{2+}]i$. As a positive control each experiment was ended by treatment with 20 mM KCl to depolarize the cell and increase $[Ca^{2+}]i$ via activation of voltage-gated channels. This maneuver served to verify the Fura-2 loading and responsiveness of the cells being tested (FIG. 2). Only L-DOPA elicited a significant increase in $[Ca^{2+}]i$ (FIG. 2A). Tyrosine and dopamine had no positive effect on intracellular at $[Ca^{2+}]i$ concentrations up to 1 mM (not shown). The slight negative effect of 1 µM dopamine was not statistically significant, but reproducible among the 11 experiments with dopamine (FIG. 2B).

Over expression of GPCRs in non-native cell lines can lead to false signal transduction coupling. To verify that OA1 signaling in response to L-DOPA was indeed a natural response, OA1 was expressed in RPE cells (FIG. 2C). Results using transfected RPE cells were similar to those achieved with transfected CHO cells. RPE cells transfected to express OA1 responded to 1.0 µM L-DOPA with an increase in $[Ca^2]i$. It was next determined whether RPE cells expressing the endogenous OA1 receptor, at endogenous levels exhibited L-DOPA responsiveness. Like all of the transfected cell experiments, RPE expressing OA1 demonstrated an increase in $[Ca^{2+}]i$ after treatment with 1.0 µM L-DOPA (FIG. 2C).

To further characterize OA1 signaling activity, pertussis toxin was used to distinguish between $G_q$ coupled $[Ca^{2+}]i$ signaling and $G_t$ linked signaling (FIG. 2C). In all cells studied, pertussis toxin lowered the basal level of $[Ca^{2+}]i$, indicating its activity on inhibition of the background signaling through $G_t$ subunit activity. Pertussis toxin was used in experiments conducted in cells transfected to express OA1 including both CHO and RPE, as well as RPE expressing the endogenous OA1 protein at natural levels. In all transfected cells tested the measured $[Ca^{2+}]i$ response to L-DOPA was greater than in the absence of the toxin (FIG. 2), owing largely to the lower initial $[Ca^{2+}]i$. Thus, the signaling through OA1 in response to L-DOPA that results in increase $[Ca^{2+}]i$ is not pertussis toxin sensitive and likely $G_q$ subunit mediated. The second messenger cAMP was also measured in CHO cells transfected to express OA1 (FIG. 2D). Using inactive cells or a submaximal forskolin treatment, the experiments were set up to measure either an increase or decrease in cAMP in response to L-DOPA. In six such experiments, no change in cAMP was observed suggesting neither $G_s$ nor $G_i$ subunits are involved in OA1 signaling.

Figure 3:
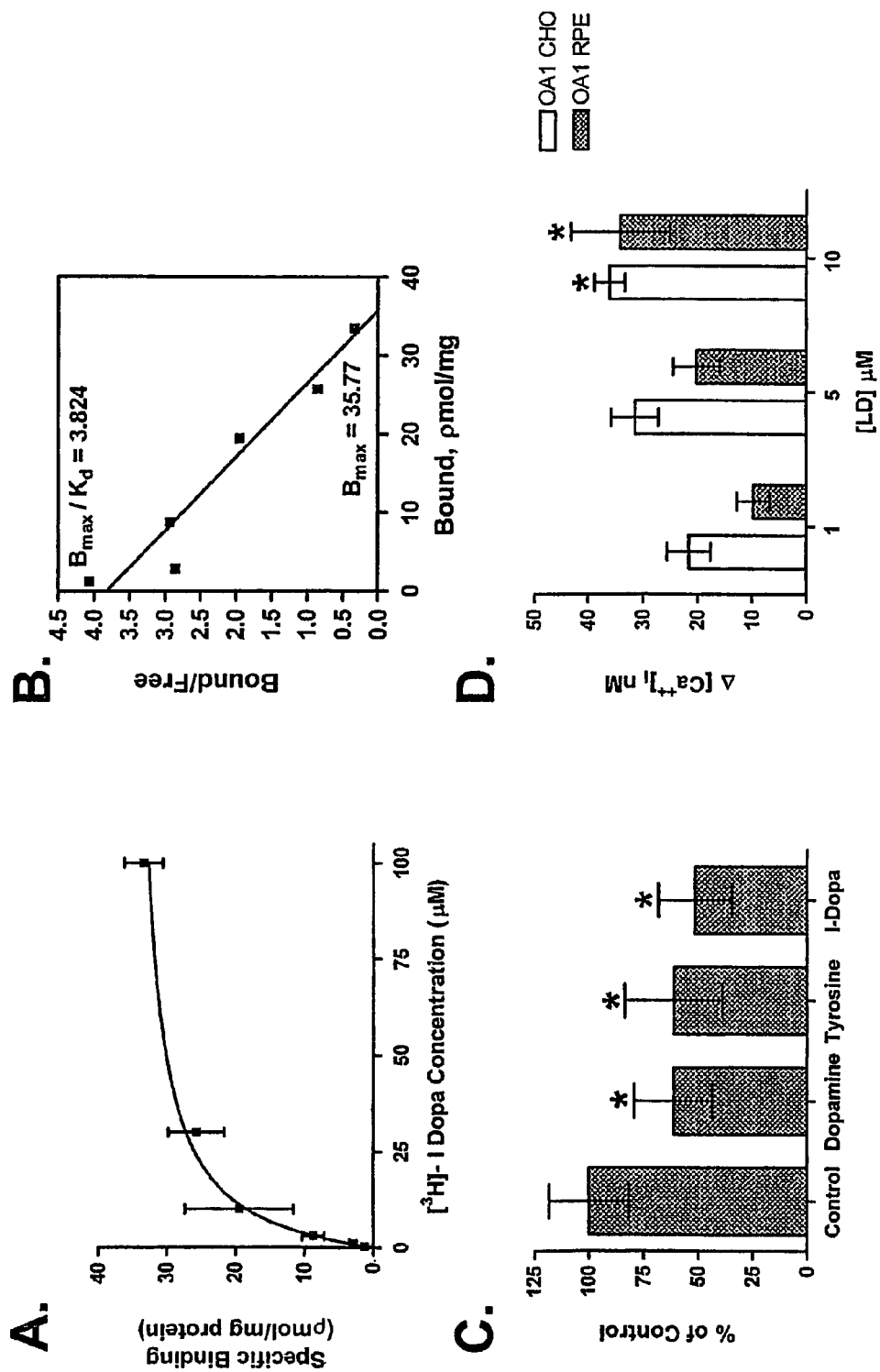
FIG. 3(a) Binding kinetics between OA1 and L-DOPA were determined using radiolabeled ligand binding assays. Results represent data collected from 5 such experiments and are presented as mean specific binding+/−SEM. The hyperbolic curve fit exhibited an $R^2$ value of 0.994, Kd was determined to be $9.34 \times 10^{-6}$ M+/−$1.14 \times 10^{-6}$ M.
FIG. 3(b) Comparative binding of 5 µM [$H^3$] L-DOPA to OA1 transfected CHO cells was compared in the presence of 1.0 mM dopamine, tyrosine, or L-DOPA. The data represent mean total binding+/−S.D. for each group. * denotes p<0.05 when comparing the results between the control group to the binding in the presence of the potential competitive ligands.
FIG. 3(c) Competitive interaction between 5 µM [$H^3$] L-DOPA and dopamine were assessed to determine whether dopamine functions as an antagonist of OA1 activity. Results indicate that dopamine and L-DOPA compete for the same OA1 binding site, and the data fits the binding model with an $r^2$ value of 0.95. The Ki for dopamine was 2.388+/−0.266 µM (mean+/−SEM), similar to the Kd for L-DOPA.
FIG. 3(d) Dose-dependent OA1 signaling through OA1. Data represent mean increase in $[Ca^{2+}]_i$ elicited by L-DOPA treatment of the cells at the concentrations given (n=6 for each dose). T-test analyzes were used to compare between the responses achieved at each dose, and * denotes p<0.01 for the comparison at 1 and 10 µM.
FIG. 3(e) Scatchard plot illustrating the kinetics of a single site binding relationship based on FIG. 3(a).
Figure 3E:
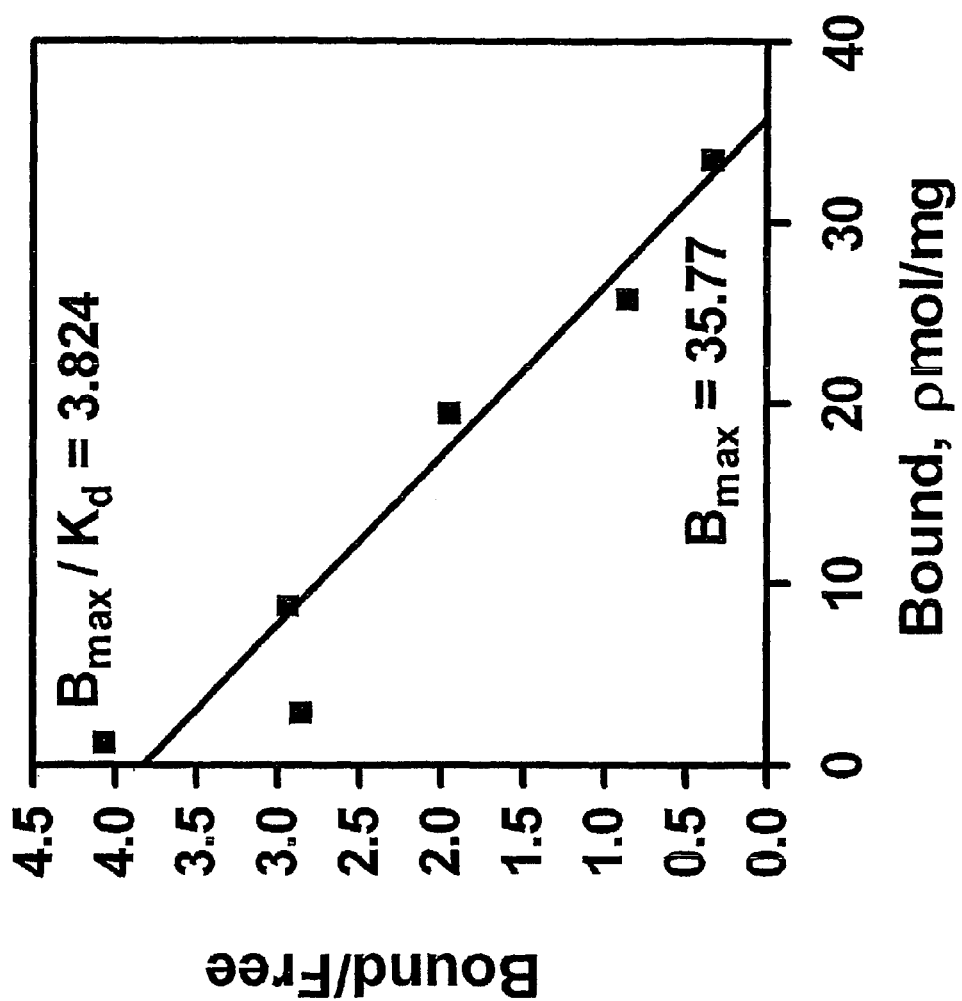
Figure 6:
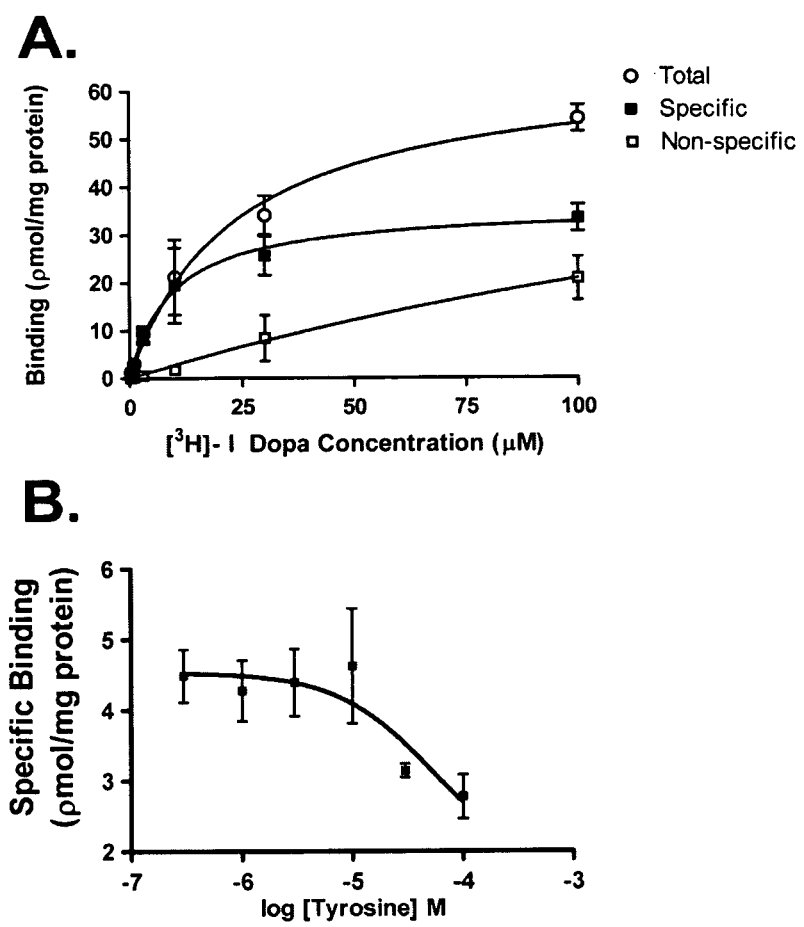
FIG. 6(a) Data represents mean+/−SEM bound [3H]-L-DOPA in all fractions, total, specific and non-specific. Non-specific binding was determined by measuring radiolabeled-L-DOPA bound in the presence of excess unlabeled L-DOPA (1 mM). Specific binding at each given concentration is determined by subtracting the measured non-specific binding from the measured total binding.
FIG. 6(b) The figure illustrates competitive interaction between tyrosine and L-DOPA, measured using increasing concentrations of tyrosine and 5 µM [$H^3$] L-DOPA. Each data point represents the mean data from 5 replicate wells, and the error bars are S.D. Data illustrate that tyrosine competes for binding with L-DOPA, but with a low affinity. The results suggest tyrosine has a Ki of 52.9 µM, and fits the single site binding model with an $r^2$ value of 0.85. Saturation could not be achieved because of the limited solubility of tyrosine.

Standard methods of radiolabeled ligand binding were used to characterize the interaction between OA1 and L-DOPA (FIG. 3A). CHO cells were transfected to express OA1, then binding of L-DOPA was quantified in a concentration-dependent manner, and the results were further characterized by Scatchard Plot analysis (FIG. 3E). Results illustrate saturable binding of L-DOPA to OA1 expressing cells with a Kd of $9.35 \times 10^{-6}$M. No specific binding was observed in untransfected CHO cells, indicating that the cells do not have an endogenous L-DOPA receptor (not shown). All binding parameters, total, specific, and nonspecific are shown as supplemental data (FIG. 6A). Tyrosine exhibited the potential to interact with OA1, but neither tyrosine nor dopamine stimulated OA1 signaling (see FIG. 2). Competitive ligand binding was used to determine whether either tyrosine or dopamine competed with L-DOPA for OA1 binding. At high concentrations (1 mM), both tyrosine and dopamine competed with L-DOPA for OA1 binding (FIG. 3B). To further characterize this the kinetics of the competition between L-DOPA and either dopamine (FIG. 3C) or tyrosine (FIG. 6B) was examined. Dopamine exhibited competitive binding to a single site with L-DOPA with a Ki of $2.33 \times 10^{-6} +/- 0.2 \times 10^{-6}$ M. Similar experiments with tyrosine demonstrated inhibition of L-DOPA binding only at high concentrations (FIG. 6B). Saturation kinetics were not possible with tyrosine because of its low affinity and insolubility at the high concentrations.

Given the relatively low affinity of OA1 for L-DOPA it was determined whether its signaling activity was dose-dependent in the range of this binding affinity. The concentrations in which binding data suggested the steepest rise in association between L-DOPA and OA1, 1.0-10 µM were tested, and results illustrate a concentration dependent GPCR response as measured by $[Ca^{2+}]i$ (FIG. 3C). Thus, the activation kinetics of L-DOPA and OA1 matched the concentration range observed in radiolabeled ligand binding experiments.

Figure 4:
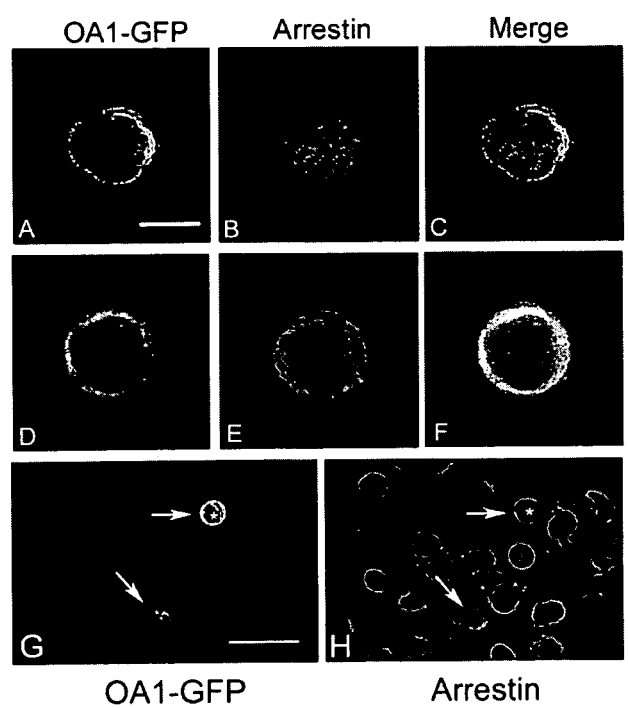
FIG. 4(a-h) All images represent 2 µm thick confocal sections of CHO cells transfected to express OA1-GFP. β-arrestin was visualized using immuno fluorescence methods. Prior to addition of L-DOPA (a-c) and after treatment with 1 µM L-DOPA (d-f), and the merged images (c, f) illustrate regions where the two proteins co-localize, at the resolution of white light imaging. (g,h) are low magnification of field of transfected CHO cells, with two transfected cells visible (arrows) (g). The remainder of the cell population is visualized using antibodies to β-arrestin (h) to illustrate that β-arrestin recruitment to the membrane only occurred in the OA1 expressing cells (arrows).

In response to ligand binding, GPCRs recruit β-arrestin to the plasma membrane which is followed by internalization of the ligand-receptor complex [27-33]. The effect of L-DOPA on β-arrestin localization was then tested (FIG. 4). Cells were transfected to express OA1 then cultured in 1 µM tyrosine DMEM for 48 hours prior to analysis to allow cell surface expression of the protein. Cells were then treated with 1 µM L-DOPA followed by rapid fixation on ice in cold methanol. Initially, under resting conditions in the absence of an agonist, OA1-GFP was found at the cell surface and β-arrestin was diffuse in the cytoplasm (FIG. 4A-C), with no co-localization between the proteins. After stimulation with L-DOPA, OA1 and β-arrestin were co-localized at the plasma membrane (FIG. 4D-F). Untransfected cells showed no response to L-DOPA treatment (FIG. 4G,H), illustrating that the L-DOPA effect on β-arrestin distribution was OA1 dependent, similar to results obtained for [Ca$^{2+}$]i.

Effects of 1-DOPA on PEDF Secretion

Figure 5:
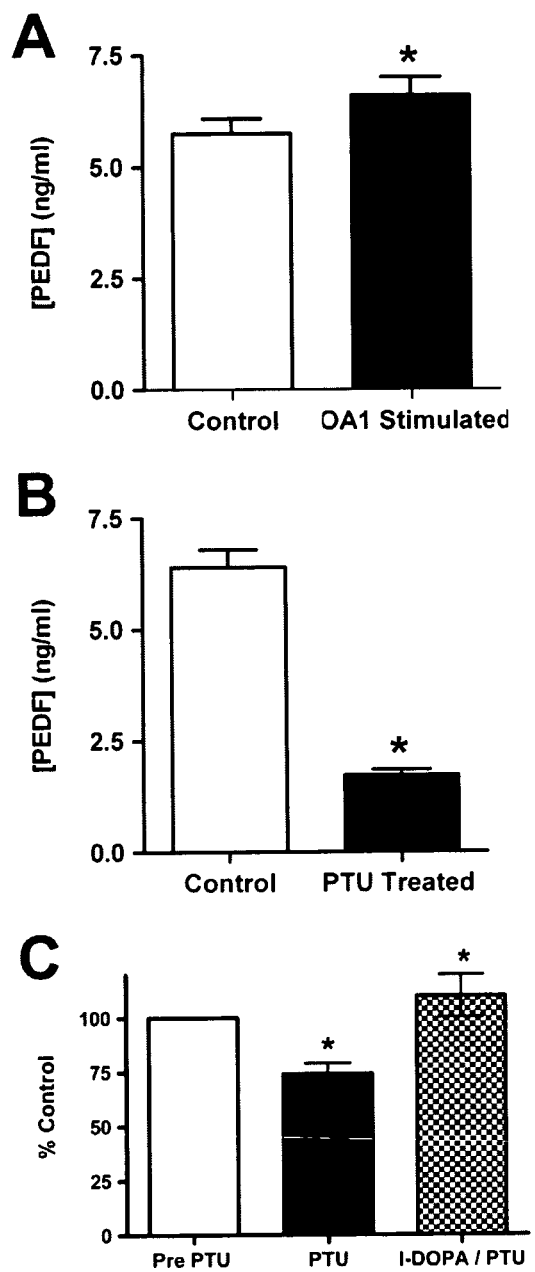
FIG. 5(a) PEDF concentrations were determined by ELISA of cell conditioned medium. RPE cells were control cells, without L-DOPA treatment, or OA1 stimulated cells that were treated with 1 µM L-DOPA prior to being maintained for 3 days in normal DMEM. Data are presented as the mean of 3 experiments conducted in triplicate, error bars represent S.D, and * denotes P<0.01 using a paired t-test.
FIG. 5(b) PEDF concentrations in conditioned medium from pigmenting RPE determined by ELISA. Cells were either control pigmenting RPE cultures or paired cultures treated with phenylthiourea (PTU) at 200 µM. Data are presented as the mean of 3 experiments conducted in triplicate, error bars represent S.D, and * denotes P<0.01 using a paired t-test.
FIG. 5(c) PEDF concentrations in conditioned medium of pigmented RPE cells treated with PTU then treated with L-DOPA to stimulate OA1 signaling. ELISA assays were conducted prior to PTU treatment, then after PTU treatment, and then from the same cultures after L-DOPA stimulation. Results are presented as mean+/−S.D. of the value achieved related to that culture of cells. * denotes p<0.01 when comparing PTU to the control (same culture tested prior to PTU), and L-DOPA/PTU compared to the PTU sample from that same culture.

Mutations in OA1 cause defects in the development of the neurosensory retina. In previous work it has been shown that pigmented RPE secrete significantly more PEDF than non-pigmented RPE [34], and PEDF is a neurotrophic factor with the potential of altering neurosensory retina development [35-41]. Mutations in OA1 cause a loss of pigmentation in the RPE, suggesting that OA1 activity governs RPE pigmentation. Thus, it was determined whether L-DOPA stimulation of pigmented RPE cells caused increased secretion of PEDF (FIG. 5). This assay is made somewhat more difficult because pigmenting RPE cells produce L-DOPA, which is the agonist for OA1, and OA1 is not readily detectable in nonpigmented cultures of RPE. Thus, pigmented RPE were used to determine whether L-DOPA stimulation increases PEDF expression/secretion. RPE cells were placed in tyrosine-free medium for 24 hours then treated with 1 μM L-DOPA for one hour. After treatment, the cells were returned to standard medium without exogenous L-DOPA for three days. Control cells were not treated with L-DOPA, but the medium was changed at the same time the experimental cells were returned to normal medium. Conditioned medium was collected after three days and PEDF was measured. Results illustrate a significant increase in the secretion of PEDF in pigmented cells treated with L-DOPA when compared to paired, control monolayers of pigmented RPE (FIG. 5A). Importantly, this significant increase occurred in cells which were pigmenting and therefore expressed OA1 and had a basal level of PEDF expression.

To determine whether pigmented RPE cells secrete PEDF through an autocrine loop involving tyrosinase activity and OA1 signaling, a specific tyrosinase inhibitor phenylthiourea (PTU) was used to inhibit pigmentation and L-DOPA production (FIG. 5B). In these experiments, pigmented RPE cells were either maintained in DMEM, or DMEM containing 200 μM PTU for three days, then PEDF secretion was measured. Pigmented RPE secreted substantial PEDF, but PTU caused a significant decrease in PEDF secretion indicating that tyrosinase activity is necessary for the high level of PEDF secretion observed in pigmented RPE cells. To verify that it was the lack of L-DOPA in the PTU treated cells that caused the decreased PEDF secretion, 3 different cultures of pigmented RPE were used, and exposed to PTU for 48 hours, then treated with 1.0 μM L-DOPA in the continued presence of PTU; PEDF was measured after 72 hours (FIG. 5C). The data are presented as percent of control for this experiment because the cultures used varied in both pigmentation and PEDF expression before the experiment began. PTU treated RPE responded to the added L-DOPA by increasing PEDF secretion, indicating that the effect of PTU on PEDF secretion is caused be the lack of L-DOPA production when tyrosinase is inhibited.

Discussion:

There is a complex inter-tissue relationship between the RPE and the neurosensory retina. One aspect of this relationship is centered on RPE pigmentation, and defects in melanin synthesis which result in significant neurosensory retina alterations [8,23,42]. The data suggest that OA1 and tyrosinase participate in an autocrine loop through L-DOPA that regulates the secretion of at least one potent neurotrophic factor, PEDF. The data also suggest that the pathologic changes in retinal development that occur in albinism may result from changes in the activity of the OA1 signaling pathway. Reduced OA1 signaling activity can be caused either directly through OA1 mutations or indirectly through changes in L-DOPA production by tyrosinase activity. Thus, it is hypothesized that the similar retinal phenotypes that accompany the diverse forms of albinism can be reconciled to a single common pathway, OA1 signaling.

In the study, OA1 on the apical surface of human RPE in situ was observed. Previous reports have suggested that OA1 in mice is localized to the melanosome [22], and in cultured cells to the endosomal compartment [15-18,20-22,43]. The results from in situ RPE preparations indicate that OA1 is distributed to the apical surface of the RPE. The limited quantities of OA1 on the surface of the RPE (~3.5% of total OA1) may account for the lack of observation of the protein in previous studies where immunogold electron microscopy was used. Like many cell surface GPCRs, OA1 is not an abundant protein.

The endosomal localization of OA1 reported in previous studies using cultured cells was reproduced in this study for both the endogenous protein and the transgenic protein. When tested in normal culture medium little detectable OA1 protein on the cell surface was found, in agreement with all previous work. However, reduction of tyrosine in the medium caused a modest increase in cell surface receptor accumulation of both the endogenous and recombinant OA1 proteins. This suggests that the distribution of OA1 to the cell surface in cultured cells is sensitive to tyrosine. A previous study has demonstrated OA1 could be localized to the cell surface when endocytosis in inhibited [17] and OA1 on the apical surface of human RPE was observed in situ. The data suggest OA1 is a cell surface GPCR, but is a target for endocytosis that may be stimulated by tyrosine or tyrosine metabolites. In this regard, the results differ from past reports of OA1 localization that have classified OA1 as a unique type of intracellular GPCR. Most GPCRs are cell surface proteins that are internalized by a variety of signals, and the data suggest OA1 is similar to most other GPCRs.

OA1 signaling activity was stimulated by L-DOPA, but not by either its precursor, tyrosine, or its neuronal metabolite dopamine. This result suggests an exquisitely sensitive receptor activity able to distinguish between closely related molecules, after all L-DOPA and tyrosine differ by a sole hydroxyl group. OA1 is sensitive to tyrosine, as tyrosine causes an intracellular localization of OA1 in cultured cells. However, no signaling response to tyrosine was noted, and competition binding studies suggest that tyrosine has a low affinity for OA1. The data suggest that the continuous exposure of cells to high concentrations of tyrosine present in normal medium is sufficient to result in internalization of OA1, but it is unlikely to result in measurable OA1 activation. Strong evidence of a single site competitive interaction between L-DOPA and dopamine was found. The Ki observed for dopamine was similar to the Kd observed for L-DOPA, suggesting that the affinity for the two tyrosine metabolites is similar. The results illustrated a slight, but reproducible, decrease in OA1 signaling from dopamine, suggesting that dopamine may be an effective antagonist or inverse agonist for OA1.

As an orphan GPCR, its signaling pathway has not previously been identified. In this study it was illustrated that OA1 signaling in response to L-DOPA causes an increase in [Ca$^{2+}$] i. The data illustrate that the increased [Ca$^{2+}$]i observed in response to L-DOPA was insensitive to pertussis toxin and no effects on cAMP were found, indicating that OA1 is likely signaling through a $G_q$ subunit. Previous work has suggested that OA1 can associate with multiple subunits in transfected cells including members of the $G_o$, $G_i$, and $G_q$ subunit families. Innamorati et al. has shown that spontaneous activity of overexpressed OA1 is likely signaled through a Gq subunit [16]. The data indicate that ligand-dependent signaling from endogenous OA1 in RPE most likely occurs through a $G_q$ mediated pathway, and no promiscuous coupling activities were observed when comparing OA1 overexpression in CHO and RPE to natural OA1 expressed in RPE. Interestingly, two overactive mutant forms of Gq subunits cause hyperpigmentation in skin and hair [44], but whether they have an effect in RPE is unknown. RPE and cutaneous melanocytes use the same enzymes to produce pigmentation but differ in their control of melanogenesis. A recent report suggests that OA1 may signal through Gαi3, because the retinal phenotype of OA1$^{-/-}$ and Gαi3$^{-/-}$ are similar [45]. That study provided no data regarding interaction or signaling between Gαi3 and OA1, and the results do not support OA1 signaling through Gαi3. However, both OA1 and Gαi3 could have activity in convergent pathways that govern some part of the complex system of retinal development.

The response of OA1 to L-DOPA was measured in three ways, increased $[Ca^{2+}]i$, recruitment of β-arrestin to plasma membrane OA1, and the increased secretion of PEDF. In addition, inhibiting the activity of tyrosinase in pigmented RPE inhibits L-DOPA production, and results in a decreased secretion of PEDF. Taken together, these studies present a strong argument for a productive ligand:receptor relationship between L-DOPA and OA1. Further, the data suggest selectivity among tyrosine and its metabolites, with only L-DOPA being a productive ligand for OA1. We have determined the binding kinetics between OA1 and L-DOPA, and observed a typical one site receptor:ligand relationship between the two. The binding affinity between OA1 and L-DOPA, with a Kd in the μM range, is not uncommon for an endogenous ligand: receptor relationship. Future identification of a specific, high affinity antagonist for OA1 will aid in further biochemical characterization of the interaction between OA1 and L-DOPA, and be useful in determining whether dopamine is an inverse agonist.

This study illustrated the selective activation of OA1, an orphan GPCR, by L-DOPA, an intermediate product of melanin synthesis. This study has also illustrated that OA1 activity stimulates PEDF secretion by RPE, a molecule that has the potential to support normal retinal development [40,41]. In humans, this suggests that pharmacologic intervention through OA1 activation could be useful for albinism caused by defects in the melanogenic machinery (OCA 1-4). Unfortunately, the data also suggest that OA1 is necessary for such pharmacologic intervention, and mutations in Oa1 are the most common cause of albinism.

Methods:
Cell Culture
RPE—

Cells were isolated as described [46] and maintained in Dulbecco's modified essential medium (DMEM) supplemented with 5% fetal bovine serum (FBS). For experiments in which tyrosine concentrations were lowered, custom manufactured DMEM produced without tyrosine by JRH Biosciences (Lenexa, Kans.) was used. Dialyzed FBS was purchased from Invitrogen, (San Diego, Calif.).

COS-7 and CHO—

Cells were obtained from ATCC and cultured in DMEM supplemented with 5% FBS. For analysis of OA1 distribution, cells were cultured in tyrosine-free DMEM supplemented with 1 μM tyrosine, 5% dialyzed FBS for 2-4 days, then tyrosine-free media as described for the experiment.

Cell Surface Biotinylation
Human RPE In Situ—

Human eyecups were produced by dissection ~2 mm anterior to the equator and removals of the anterior segment. The vitreous and retina were removed without impairing the underlying RPE monolayer, and the retina was cut at the optic nerve head. The resulting eyecups with RPE exposed were rinsed three times with reaction buffer (100 mM NaCl, 50 mM NaHCO3, pH 8.0) then filled with Sulfo-NHS-LC-Biotin (1 mg/ml) two times for thirty minutes. The reaction was stopped with TG buffer (25 mM Tris, 192 mM Glycine, pH 8.3) then the cells were harvested in lysis buffer (2 mM EDTA, 1% Triton X and 1% Tween 20 in Tris Base Saline Buffer) containing Halt Protease Inhibitor Cocktail. Intact cells and pigment granules were removed by centrifugation at 14,000 rpm for 20 minutes. Biotinylated proteins were captured overnight with immobilized streptavidin beads and then mixed with 4× reducing buffer (250 mM Tris, pH 6.8, 8% SDS, 40% Glycerol, 20% Beta-mercaptoethanol, 0.08% bromophenol blue). The OA1 protein was separated on a 10% SDS-PAGE gel and identified by a using a polyclonal rabbit OA1 antibody for western blot analysis. Paired western blots were probed with a monoclonal antibody directed against actin.

Cultured Cells—

RPE and transfected cells were maintained in DMEM containing tyrosine concentrations described for the experiment. Cultures were rinsed three times in reaction buffer, then biotinylated as described above for the in situ preparation.

Cloning of Oa1

A cDNA library was constructed from pooled tissue from 6 human donor eyes. Total RNA was harvested using Trizol reagent, then cDNA was synthesized using Poly-T primers for the first strand synthesis, and random hexamers for the second strand. Following cDNA synthesis, RNA was removed using RNase A. The coding sequence for OA1 was obtained by PCR using terminal primers that added restriction sites to the 5' and 3' ends and removed the native stop codon. The PCR product was ligated in frame with GFP in the pEGFP N-1 vector (Clontech). The sequence was verified by automated sequencing in both directions over the entire sequence.

Immunocytochemistry

Cells on slides were fixed with 3% paraformaldehyde at RT, rinsed with 0.1% Triton X-100 in 10% milk in TBST then blocked with 10% milk in TBST. β-arrestin was visualized using a polyclonal antibody directed against β-arrestin, and incubated overnight at 4° C. Cover slips were mounted using 50% glycerol and immunostaining was analyzed by optical sectioning using a Nikon Eclipse E800 laser scanning confocal microscope powered by Compix Confocal Imaging Systems software (Simple PCI Version 4.0.6.1605). Three-dimensional analysis of OA1-GFP and β-arrestin distribution was performed in Image J 1.32.

Measurement of $[Ca^{2+}]i$

OA1-GFP expressing CHO cells plated on glass cover slips were rinsed in $Ca^{2+}$ containing HEPES buffered Hanks Balanced Salt Solution (HBSS) (pH 7.45), then incubated with 2.5 μM Fura-2 (solubilized in anhydrous dimethylsulfoxide and 0.002% pluronic acid) for 20 minutes at 37° C., 5% $CO_2$. The Fura-2 loaded cells were rinsed with HBSS for 15 minutes at 37° C., 5% $CO_2$ to allow for full cleavage of the dye to its active form. Each cover slip was incubated in 1 ml of HBSS in a chamber held at 37° C. on the stage of an inverted Olympus IX70 microscope equipped with a 40×1.35 NA UV-fluor objective.

Using a filter wheel, excitation light from a 200 W Xe bulb was passed alternately through 340 and 380 nm filters. A 10 nm bandpass filter, centered at 510 nm, selected for the emitted fluorescence which was passed to a CCD camera (Photometrics CH-250). For each experiment, image pairs were taken every minute for the first three minutes, which established a stable baseline. Then L-DOPA (1 µM final concentration) was added and image sets were taken every 30 seconds for the next three minutes. Finally, KCl (20 mM final concentration) was added one minute before completion of each experiment as a positive control to establish that the cells were loaded with Fura-2. The same was repeated independently for tyrosine and dopamine (both at 1 µM final concentration). Using a Silicon Graphics Personal IRIS computer, the 340/380 nm ratio was computed for each pixel within a cell, and then analyzed using Microsoft Excel version 4.0 (Microsoft, Redmond, Wash.). Once the 340/380 nm ratio was determined, each ratio was normalized to 1 (ratio at time zero divided by itself), then the free ion concentration was calculated using the following equation:

$$[Ca_i]\# = Kd\# * (R - R_{min}\#)/R_{max}\# - R)$$

in which R, $R_{min}$, and $R_{max}$ are the measured, minimum, and maximum ratios, respectively. $R_{max}$ represents the ratio of fluorescence intensity of ion-sensitive wavelengths under fully deprotonated conditions, whereas $R_{min}$ is the ratio for the dye when it is fully protonated. In the case of Fura-2, R increases with increasing $Ca^{2+}$; hence $R_{min}$ represents Fura-2 in the absence of $Ca^{2+}$ ($Ca^{2+} < 1$ nM) whereas $R_{max}$ represents the $Ca^{2+}$-Fura-2 chelate as previously described [26]. $R_{min}$, $R^{max}$ and Kd were determined in independent experiments in Fura-2 loaded cells, and subsequently utilized for calculation of free $Ca^{2+}$ for the experimental procedures.

Radiolabeled Ligand Binding

CHO cells were transfected to express OA1-GFP were plated into 24-well plates. Cells were chilled to −2 C, then rinsed in cold binding buffer, 25 mM Tris, 150 mM NaCl, 5 mM EDTA, 5 µM digitonin (pH 7.45). Cells were incubated for two hours in binding buffer containing [$^3$H]-L-DOPA (Moravek Biochemicals, Brea, Calif.) at concentrations between $10^{-4}$M to $10^{-9}$M. The temperature was not allowed to exceed −2° C. at any step of the assay. Controls included assays conducted on nontransfected CHO and specific binding was determined by competition with excess unlabelled L-DOPA at $10^{-3}$M. Bound L-DOPA was quantified by scintillation spectroscopy.

Measurement of cAMP

Cells were pretreated with forskolin (15 minutes) then challenged with L-DOPA using an assay setup as previously described [47]. After 1 minute of ligand exposure, cells are scraped into ice-cold buffer, boiled then centrifuged. Equivalent volumes, 50 µl, of supernate and $^3$H-cAMP (New England Nuclear) then combined with 100 µl cold PKA. After 2 hours, the solution is passed over activated charcoal, and supernates are counted in a scintillation counter. Results are compared to those achieved using a standard curve, instead of cytosol, produced using 50 µl of cAMP 0.25-32.0 pmole/500 µl.

Example 2

The OA1 Loop Functions In Vivo

Figure 7:
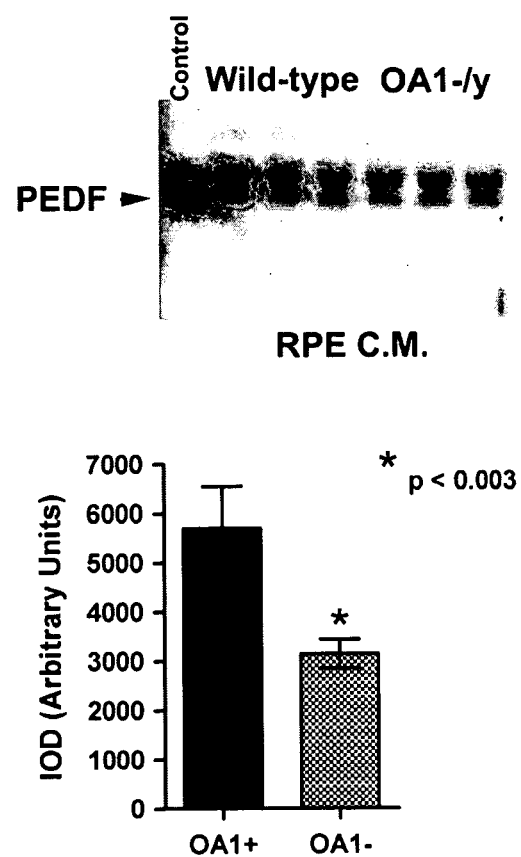
FIG. 7 Western blot and graphical representation of PEDF secretion in wild-type vs OA deficient mice.

PEDF secretion in OA deficient mice was compared to wild type mice, and showed that wild-type mice secreted significantly more PEDF than OA1-/y mice. The culture medium (C.M.) used contains PEDF, and it is likely that PEDF in the CM from OA1-/y is from the medium used, not the RPE. Results (FIG. 7) are quantified and summarized in the graph. The difference, even with the background PEDF in the CM for both groups is significant. T-test analysis results are presented Tyrosinase deficient pregnant mice were maintained under normal conditions (No L-DOPA), or supplemented with 1.0 mg/mL-DOPA in there drinking water, beginning on embryonic day 7 for their pups. Animals were maintained on supplemental until post-natal day 14, when ocular development is over and the eyes are open.

Figure 8:
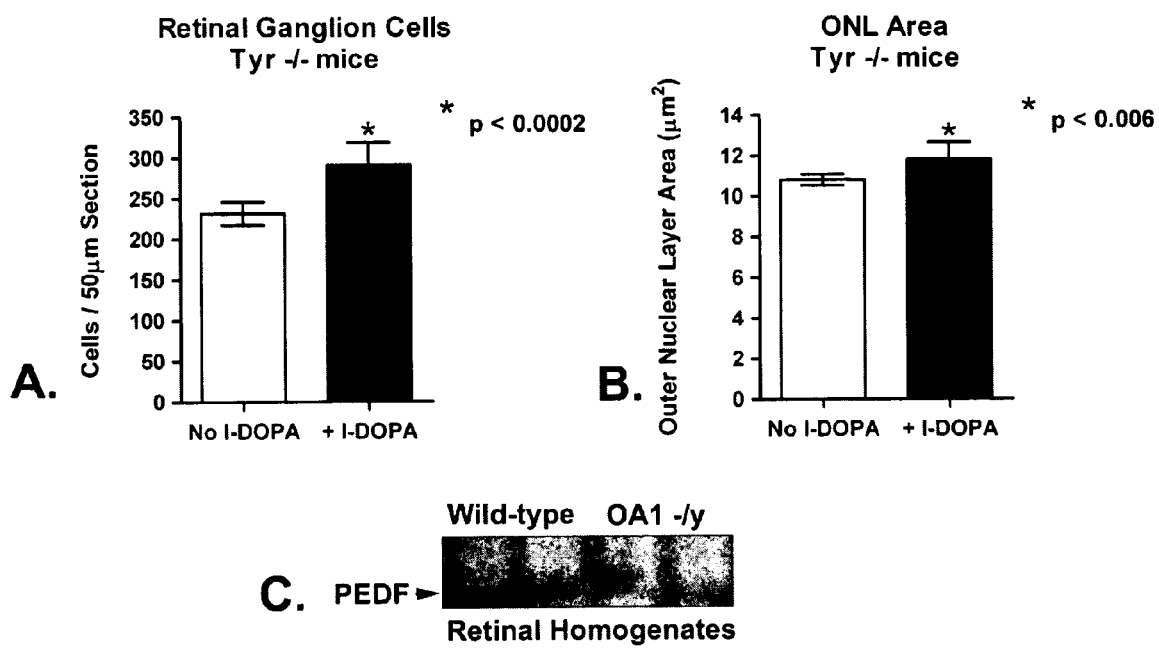
FIG. 8(a) is a graphical representation of data demonstrating that L-DOPA supplementation increases retinal ganglion cell numbers compared to what is expected in a normal wild-type mouse.
FIG. 8(b) is a graphical representation of data demonstrating that L-DOPA supplementation increases photoreceptor numbers compared to what is expected in a normal wild-type mouse.
FIG. 8(c) is a Western blot showing PEDF detection in 2 wild-type and 2OA1-/y mice.

Two cell types are reduced in number in albinism: retinal ganglion cells and photoreceptors. FIG. 8A demonstrates that L-DOPA supplementation increases retinal ganglion cell numbers compared to what is expected in a normal wild-type mouse. FIG. 8B shows the same result for photoreceptors. Photoreceptors are not counted directly as they are too dense. Rather, the area occupied by photoreceptor nuclei is measured as a measure of photoreceptor numbers. L-DOPA supplementation increased the photoreceptor nuclear area, so the number of photoreceptors were increased. Again, this appeared to restore the albino animal to normal levels.

As shown in FIG. 8C, Four paired littermate animals, 2 wild-type and 2 OA1-/y (female OA1 deficient) were euthanized and the retinas from each animal were loaded independently in a lane, then proteins were western blotted to detect PEDF, which was readily observed in the retina from wild-type mice. In contrast, PEDF is not readily detected in the retinas from the OA1-/y mice.

In summary this data illustrate that OA1-/y mice make less PEDF than wild type mice. L-DOPA stimulation in tyrosinase defective mice rescues the two most prominent neurosensory retina defects of albinism: a loss of photoreceptor cells and retinal ganglion cells. Finally, PEDF levels are reduced in the retinas of mice lacking OA1. Thus, it is concluded that the OA1 autocrine loop functions in vivo, and can be stimulated with oral L-DOPA.

The data together illustrate that the linkage between RPE pigmentation and AMD are likely through the signaling activity of OA1. The data illustrate that the ligand for OA1 is L-DOPA, and that OA1 signaling from L-DOPA controls the expression of PEDF. PEDF is the most potent neurotrophic factor made by RPE. Thus, the identification of L-DOPA as the ligand for OA1, which controls PEDF expression, ties together L-DOPA and neurotrophic activity in the RPE. Because L-DOPA is produced as a by-product of pigment production, this established for the first time a linkage between RPE pigmentation and neurotrophic activity. This system is defined as the OA1 autocrine loop. Tyrosinase makes pigment and releases L-DOPA. Released L-DOPA binds to and initiates signaling through OA1. OA1 signaling controls the expression of both tyrosinase and PEDF.

To date the data illustrate this model biochemically, in cultured cells, and in vivo. The fact that retinal development in an albino animal can be rescued using dietary L-DOPA indicates that dietary L-DOPA can be used to stimulate RPE trophic factor expression in vivo. AMD is clearly tied to an RPE defect somehow related to its pigmentation. Blue-eyed individuals get AMD at a much greater frequency than dark-eyed individuals, so the level of RPE pigmentation controls the AMD process. The level of RPE pigmentation is controlled by OA1 signaling and is part of the same OA1 autocrine loop described above. Thus, AMD is related to OA1 signaling in RPE. Therefore, those with lower RPE pigmentation will have lower tyrosinase, lower L-DOPA, lower OA1 signaling, and lower PEDF production. We can use dietary L-DOPA or related compounds as ligands for OA1 and stimulate that activity. The final determinant of the health of the neurosensory retina is PEDF, but we can use OA1 signaling to increase the OA1 loop activity, and increase the neurotrophic activity of the RPE. The effect of OA1 signaling will be to foster neuron survival.

LITERATURE CITED

1. Akeo K, Shirai S, Okisaka S, Shimizu H, Miyata H, et al. (1996) Histology of fetal eyes with oculocutaneous albinism. Arch Ophthalmol 114: 613-616.
2. Gregor Z (1978) The perifoveal vasculature in albinism. Br J Ophthalmol 62: 554-557.
3. Schraermeyer U, Heimann K (1999) Current understanding on the role of retinal pigment epithelium and its pigmentation. Pigment Cell Res 12: 219-236.
4. Rachel R A, Mason C A, Beermann F (2002) Influence of tyrosinase levels on pigment accumulation in the retinal pigment epithelium and on the uncrossed retinal projection. Pigment Cell Res 15: 273-281.
5. Okulicz J F, Shah R S, Schwartz R A, Janniger C K (2003) Oculocutaneous albinism. J Eur Acad Dermatol Venereol 17: 251-256.
6. Donatien P, Jeffery G (2002) Correlation between rod photoreceptor numbers and levels of ocular pigmentation. Invest Ophthalmol V is Sci 43: 1198-1203.
7. Russell-Eggitt I (2001) Albinism. Ophthalmol Clin North Am 14: 533-546.
8. Oetting W S (1999) Albinism. Curr Opin Pediatr 11: 565-571.
9. Oetting W S, King R A (1999) Molecular basis of albinism: mutations and polymorphisms of pigmentation genes associated with albinism. Hum Mutat 13: 99-115.
10. Shen B, Samaraweera P, Rosenberg B, Orlow S J (2001) Ocular albinism type 1: more than meets the eye. Pigment Cell Res 14: 243-248.
11. Incerti B, Cortese K, Pizzigoni A, Surace E M, Varani S, et al. (2000) Oa1 knock-out: new insights on the pathogenesis of ocular albinism type 1. Hum Mol Genet. 9: 2781-2788.
12. Bassi M T, Schiaffino M V, Renieri A, De Nigris F, Galli L, et al. (1995) Cloning of the gene for ocular albinism type 1 from the distal short arm of the X chromosome. Nat Genet 10: 13-19.
13. Schiaffino M V, Bassi M T, Galli L, Renieri A, Bruttini M, et al. (1995) Analysis of the OA1 gene reveals mutations in only one-third of patients with X-linked ocular albinism. Hum Mol Genet 4: 2319-2325.
14. Schiaffino M V, d'Addio M, Alloni A, Baschirotto C, Valetti C, et al. (1999) Ocular albinism: evidence for a defect in an intracellular signal transduction system. Nat Genet 23: 108-112.
15. Schiaffino M V, Tacchetti C (2005) The ocular albinism type 1 (OA1) protein and the evidence for an intracellular signal transduction system involved in melanosome biogenesis. Pigment Cell Res 18: 227-233.
16. Innamorati G, Piccirillo R, Bagnato P, Palmisano I, Schiaffino M V (2006) The melanosomal/lysosomal protein OA1 has properties of a G protein-coupled receptor. Pigment Cell Research 19: 125-135.
17. Staleva L, Orlow S J (2006) Ocular albinism 1 protein: trafficking and function when expressed in *Saccharomyces cerevisiae*. Exp Eye Res 82: 311-318.
18. Shen B, Orlow S J (2001) The ocular albinism type 1 gene product is an N-glycoprotein but glycosylation is not required for its subcellular distribution. Pigment Cell Res 14: 485-490.
19. d'Addio M, Pizzigoni A, Bassi M T, Baschirotto C, Valetti C, et al. (2000) Defective intracellular transport and processing of OA1 is a major cause of ocular albinism type 1. Hum Mol Genet 9: 3011-3018.
20. Shen B, Rosenberg B, Orlow S J (2001) Intracellular distribution and late endosomal effects of the ocular albinism type 1 gene product: consequences of disease-causing mutations and implications for melanosome biogenesis. Traffic 2: 202-211.
21. Samaraweera P, Shen B, Newton J M, Barsh G S, Orlow S J (2001) The mouse ocular albinism 1 gene product is an endolysosomal protein. Exp Eye Res 72: 319-329.
22. Schiaffino M V, Baschirotto C, Pellegrini G, Montalti S, Tacchetti C, et al. (1996) The ocular albinism type 1 gene product is a membrane glycoprotein localized to melanosomes. Proc Natl Acad Sci USA 93: 9055-9060.
23. Ilia M, Jeffery G (2000) Retinal cell addition and rod production depend on early stages of ocular melanin synthesis. J Comp Neurol 420: 437-444.
24. Ilia M, Jeffery G (1999) Retinal mitosis is regulated by dopa, a melanin precursor that may influence the time at which cells exit the cell cycle: analysis of patterns of cell production in pigmented and albino retinae. J Comp Neurol 405: 394-405.
25. Ito S (2003) The IFPCS presidential lecture: a chemist's view of melanogenesis. Pigment Cell Res 16: 230-236.
26. Martinez-Zaguilan R, Tompkins L S, Gillies R J, Lynch R M (2006) Simultaneous analysis of intracellular pH and Ca2+ from cell populations. Methods Mol Biol 312: 269-287.
27. Ferguson S S, Caron M G (2004) Green fluorescent protein-tagged beta-arrestin translocation as a measure of G protein-coupled receptor activation. Methods in Molecular Biology 237: 121-126.
28. Barak L S, Warabi K, Feng X, Caron M G, Kwatra M M (1999) Real-time visualization of the cellular redistribution of G protein-coupled receptor kinase 2 and beta-arrestin 2 during homologous desensitization of the substance P receptor. J Biol Chem 274: 7565-7569.
29. Zhang J, Barak L S, Anborgh P H, Laporte S A, Caron M G, et al. (1999) Cellular trafficking of G protein-coupled receptor/beta-arrestin endocytic complexes. J Biol Chem 274: 10999-11006.
30. Tohgo A, Choy E W, Gesty-Palmer D, Pierce K L, Laporte S, et al. (2003) The stability of the G protein-coupled receptor-beta-arrestin interaction determines the mechanism and functional consequence of ERK activation. J Biol Chem 278: 6258-6267.
31. Ferguson S S, Zhang J, Barak L S, Caron M G (1998) Molecular mechanisms of G protein-coupled receptor desensitization and resensitization. Life Sci 62: 1561-1565.
32. Barak L S, Ferguson S S, Zhang J, Caron M G (1997) A beta-arrestin/green fluorescent protein biosensor for detecting G protein-coupled receptor activation. J Biol Chem 272: 27497-27500.
33. Barak L S, Ferguson S S, Zhang J, Martenson C, Meyer T, et al. (1997) Internal trafficking and surface mobility of a functionally intact beta2-adrenergic receptor-green fluorescent protein conjugate. Mol Pharmacol 51: 177-184.
34. McKay B S, Goodman B, Falk T, Sherman S J (2006) Retinal pigment epithelial cell transplantation could provide trophic support in Parkinson's disease: Results from an in vitro model system. Exp Neurol 201: 234-243.
35. Tombran-Tink J, Shivaram S M, Chader G J, Johnson L V, Bok D (1995) Expression, secretion, and age-related downregulation of pigment epithelium-derived factor, a serpin with neurotrophic activity. J Neurosci 15: 4992-5003.
36. Malchiodi-Albedi F, Feher J, Caiazza S, Formisano G, Perini R, et al. (1998) PEDF (pigment epithelium-derived factor) promotes increase and maturation of pigment granules in pigment epithelial cells in neonatal albino rat retinal cultures. Int J Dev Neurosci 16: 423-432.
37. Behling K C, Surace E M, Bennett J (2002) Pigment epithelium-derived factor expression in the developing mouse eye. Mol V is 8: 449-454.
38. Aymerich M S, Alberdi E M, Martinez A, Becerra S P (2001) Evidence for pigment epithelium-derived factor receptors in the neural retina. Invest Ophthalmol V is Sci 42: 3287-3293.
39. Tombran-Tink J, Chader G G, Johnson L V (1991) PEDF: a pigment epithelium-derived factor with potent neuronal differentiative activity. Exp Eye Res 53: 411-414.
40. Jablonski M M, Tombran-Tink J, Mrazek D A, Iannaccone A (2001) Pigment epithelium-derived factor supports normal Muller cell development and glutamine synthetase expression after removal of the retinal pigment epithelium. Glia 35: 14-25.
41. Jablonski M M, Tombran-Tink J, Mrazek D A, Iannaccone A (2000) Pigment epithelium-derived factor supports normal development of photoreceptor neurons and opsin expression after retinal pigment epithelium removal. J Neurosci 20: 7149-7157.
42. Jeffery G (1998) The retinal pigment epithelium as a developmental regulator of the neural retina. Eye 12 (Pt 3b): 499-503.
43. Piccirillo R, Palmisano I, Innamorati G, Bagnato P, Altimare D, et al. (2003) An unconventional dileucine-based motif and a novel cytosolic motif are required for the lysosomal and melanosomal targeting of OA1. Journal of Cell Science 119: 2003-2014.
44. Van Raamsdonk C D, Fitch K R, Fuchs H, de Angelis M H, Barsh G S (2004) Effects of G-protein mutations on skin color. Nat Genet 36: 961-968.
45. Young A, Powelson E B, Whitney I E, Raven M A, Nusinowitz S, et al. (2008) Involvement of OA1, an intracellular GPCR, and G alpha i3, its binding protein, in melanosomal biogenesis and optic pathway formation. Invest Ophthalmol V is Sci 49: 3245-3252.
46. Hu J, Bok D (2001) A cell culture medium that supports the differentiation of human retinal pigment epithelium into functionally polarized monolayers. Mol V is 7: 14-19.
47. Stamer W D, Golightly S F, Hosohata Y, Ryan E P, Porter A C, et al. (2001) Cannabinoid CB(1) receptor expression, activation and detection of endogenous ligand in trabecular meshwork and ciliary process tissues. Eur J Pharmacol 431: 277-286.

We claim:

1. A method for treating age-related macular degeneration (AMD), comprising administering to a subject with AMD an amount of an agonist of the OA1 receptor selected from the group consisting of L-DOPA, an L-DOPA analogue, and pharmaceutically acceptable salts thereof, effective for treating AMD.

2. The method of claim 1, wherein the agonist comprises L-DOPA, or a pharmaceutically acceptable salt thereof.

3. The method of claim 1, wherein the L-DOPA analogue comprises an L-DOPA prodrug, or a pharmaceutically acceptable salt thereof.

4. The method of claim 3, wherein the L-DOPA prodrug comprises an L-DOPA ester, or a pharmaceutically acceptable salt thereof.

5. The method of claim 3, wherein the L-DOPA prodrug comprises a bile acid conjugate of L-DOPA, or a pharmaceutically acceptable salt thereof.

6. The method of claim 3 wherein the L-DOPA prodrug comprises a di- or tri-peptide L-DOPA analogue, or a pharmaceutically acceptable salt thereof.

7. The method claim 1, wherein the subject is over the age of 60.

8. The method of claim 1, wherein the subject has wet AMD.

9. The method of claim 1, wherein the subject has dry AMD.

10. The method of claim 1, further comprising administering to the subject a combination of a vitamin C source, a vitamin E source, a beta-carotene source, a zinc source, and a copper source.

11. The method of claim 10, comprising administering
between 450 mg and 600 mg vitamin C;
between 400 IU and 540 IU vitamin E;
between 17.2 mg and 28 mg beta-carotene;
between 68 mg and 100 mg zinc; and
between 1.6 mg and 2.4 mg copper.

12. The method claim 2, wherein the subject is over the age of 60.

13. The method of claim 2, wherein the subject has wet AMD.

14. The method of claim 2, wherein the subject has dry AMD.

15. The method of claim 2, further comprising administering to the subject a combination of a vitamin C source, a vitamin E source, a beta-carotene source, a zinc source, and a copper source.

16. The method of claim 15, comprising administering
between 450 mg and 600 mg vitamin C;
between 400 IU and 540 IU vitamin E;
between 17.2 mg and 28 mg beta-carotene;
between 68 mg and 100 mg zinc; and
between 1.6 mg and 2.4 mg copper.

* * * * *

SEQUENCE LISTING

```
<160> NUMBER OF SEQ ID NOS: 58

<210> SEQ ID NO 1
<211> LENGTH: 1607
<212> TYPE: DNA
<213> ORGANISM: Homo sapiens

<400> SEQUENCE: 1
atgacccagg caggccggcg gggtcctggc acacccgagc cgcgtccgcg aacacagccc      60
atggcctccc cgcgcctagg gaccttctgc tgccccacgc gggacgcagc cacgcagctc     120
gtgctgagct tccagccgcg ggccttccac gcgctctgcc tgggcagcgg cgggctccgc     180
ttggcgctgg gccttctgca gctgctgccc ggccgccggc ccgcgggccc cgggtccccc     240
gcgacgtccc cgccggcctc ggtccgcatc ctgcgcgctg ccgctgcctg cgaccttctc     300
ggctgcctgg gtatggtgat ccggtccacc gtgtggttag gattcccaaa ttttgttgac     360
agcgtctcgg atatgaacca cacggaaatt tggcctgctg ctttctgcgt ggggagtgcg     420
atgtggatcc agctgttgta cagtgcctgc ttctggtggc tgttttgcta tgcagtggat     480
gcttatctgg tgatccggag atcggcagga ctgagcacca tcctgctgta tcacatcatg     540
gcgtggggcc tggccaccct gctctgtgtg gagggagccg ccatgctcta ctaccttcc     600 gtgtccaggt gtgagcgggg cctggaccac gccatccccc actatgtcac catgtacctg     660
cccctgctgc tggttctcgt ggcgaacccc atcctgttcc aaaagacagt gactgcagtg     720
gcctctttac ttaaaggaag acaaggcatt tacacggaga acgagaggag gatgggagcc     780
gtgatcaaga tccgattttt caaaatcatg ctggttttaa ttatttgttg gttgtcgaat     840
atcatcaatg aaagcctttt attctatctt gagatgcaaa cagatatcaa tggaggttct     900
ttgaaacctg tcagaactgc agccaagacc acatggttta ttatgggaat cctgaatcca     960 gcccaggat ttctcttgtc tttggccttc tacgctgga caggatgcag cctgggtttt    1020
cagtctccca ggaaggagat ccagtgggaa tcactgacca cctcggctgc tgaggggct    1080
```

-continued

```
cacccatccc cactgatgcc ccatgaaaac cctgcttccg ggaaggtgtc tcaagtgggt    1140
gggcagactt ctgacgaagc cctgagcatg ctgtctgaag gttctgatgc cagcacaatt    1200
gaaattcaca ctgcaagtga atcctgcaac aaaaatgagg gtgaccctgc tctcccaacc    1260
catggagacc tatgaagggg atgtgctggg ggtccagacc ccatattcct cagactcaac    1320
aattcttgtt ctttagaact gtgttctcac cttcccaaca ctgcactgcc gaagtgtagc    1380
ggcccccaaa ccttgctctc atcaccagct agagcttctt cccgaagggc ctttaggata    1440
ggagaaaggg ttcatgcaca cacgtgtgag aatggaagag ccccctccag accactctac    1500
agctgctcta gccttagttg ccactaggaa gttttctgag gctggctgta aagtaagtgt    1560
aaggtccaca tccttgggga agtagttaaa taaaatagtt atgactg                  1607
```

<210> SEQ ID NO 2
<211> LENGTH: 424
<212> TYPE: PRT
<213> ORGANISM: Homo sapiens

<400> SEQUENCE: 2

```
Met Thr Gln Ala Gly Arg Arg Gly Pro Gly Thr Pro Glu Pro Arg Pro
1               5                   10                  15

Arg Thr Gln Pro Met Ala Ser Pro Arg Leu Gly Thr Phe Cys Cys Pro
            20                  25                  30

Thr Arg Asp Ala Ala Thr Gln Leu Val Leu Ser Phe Gln Pro Arg Ala
        35                  40                  45

Phe His Ala Leu Cys Leu Gly Ser Gly Gly Leu Arg Leu Ala Leu Gly
    50                  55                  60

Leu Leu Gln Leu Leu Pro Gly Arg Arg Pro Ala Gly Pro Gly Ser Pro
65                  70                  75                  80

Ala Thr Ser Pro Pro Ala Ser Val Arg Ile Leu Arg Ala Ala Ala
                85                  90                  95

Cys Asp Leu Leu Gly Cys Leu Gly Met Val Ile Arg Ser Thr Val Trp
            100                 105                 110

Leu Gly Phe Pro Asn Phe Val Asp Ser Val Ser Asp Met Asn His Thr
        115                 120                 125

Glu Ile Trp Pro Ala Ala Phe Cys Val Gly Ser Ala Met Trp Ile Gln
    130                 135                 140

Leu Leu Tyr Ser Ala Cys Phe Trp Trp Leu Phe Cys Tyr Ala Val Asp
145                 150                 155                 160

Ala Tyr Leu Val Ile Arg Arg Ser Ala Gly Leu Ser Thr Ile Leu Leu
                165                 170                 175

Tyr His Ile Met Ala Trp Gly Leu Ala Thr Leu Leu Cys Val Glu Gly
            180                 185                 190

Ala Ala Met Leu Tyr Tyr Pro Ser Val Ser Arg Cys Glu Arg Gly Leu
        195                 200                 205

Asp His Ala Ile Pro His Tyr Val Thr Met Tyr Leu Pro Leu Leu Leu
    210                 215                 220

Val Leu Val Ala Asn Pro Ile Leu Phe Gln Lys Thr Val Thr Ala Val
225                 230                 235                 240

Ala Ser Leu Leu Lys Gly Arg Gln Gly Ile Tyr Thr Glu Asn Glu Arg
                245                 250                 255

Arg Met Gly Ala Val Ile Lys Ile Arg Phe Phe Lys Ile Met Leu Val
            260                 265                 270

Leu Ile Ile Cys Trp Leu Ser Asn Ile Ile Asn Glu Ser Leu Leu Phe
```

```
                275                 280                 285
Tyr Leu Glu Met Gln Thr Asp Ile Asn Gly Gly Ser Leu Lys Pro Val
    290                 295                 300

Arg Thr Ala Ala Lys Thr Thr Trp Phe Ile Met Gly Ile Leu Asn Pro
305                 310                 315                 320

Ala Gln Gly Phe Leu Ser Leu Ala Phe Tyr Gly Trp Thr Gly Cys
                325                 330                 335

Ser Leu Gly Phe Gln Ser Pro Arg Lys Glu Ile Gln Trp Glu Ser Leu
                340                 345                 350

Thr Thr Ser Ala Ala Glu Gly Ala His Pro Ser Pro Leu Met Pro His
            355                 360                 365

Glu Asn Pro Ala Ser Gly Lys Val Ser Gln Val Gly Gly Gln Thr Ser
    370                 375                 380

Asp Glu Ala Leu Ser Met Leu Ser Glu Gly Ser Asp Ala Ser Thr Ile
385                 390                 395                 400

Glu Ile His Thr Ala Ser Glu Ser Cys Asn Lys Asn Glu Gly Asp Pro
            405                 410                 415

Ala Leu Pro Thr His Gly Asp Leu
            420

<210> SEQ ID NO 3
<211> LENGTH: 1651
<212> TYPE: DNA
<213> ORGANISM: Mus musculus

<400> SEQUENCE: 3
gaggttcggg aagaggcaca gggcacatga cgcccaatct ccctcaccag cccagcacct      60
gatcaggaaa agctgaaagc tgtgggttcc gcaaaccaga gaccggtccc tgagcaagac     120
gaatggcctc cccgcgcctg ggaatttcct gctgccctac gtgggacgca gccacacagc     180
tggtgctaag cttccaaccg cgggtgttcc atgccctgtg cctgggaagc ggcactctcc     240
gcctggtgct tggcctcctt cagctcctat cagggcgtcg atctgttggt cacagggcgc     300
ctgcgacatc cccagccgcc tcagtccaca tcctccgtgc tgccactgcc tgtgacttgc     360
ttggctgcct gggaatcgtt atcaggtcca cagtgtggat agcctaccca gagttcattg     420
aaaacatttc caatgtgaat gcaacagaca tttggcctgc tactttctgt gtggggagcg     480
caatgtggat ccagctgttg tacagtgcct gcttctggtg gctcttttgc tatgcagttg     540
atgtatactt ggtgatcagg agatcggcgg acggagcac catcctgctg taccacatca     600
tggcctgggg cctggctgtg ctgctctgtg tggaggagc agtcatgctc tactaccctt     660
ctgtgtccag gtgtgagagg ggcctggacc atgccatccc ccattatgtc accacatact     720
tgccacttct gcttgtcctg gtggccaacc caatcctgtt tcacaagaca gtgacttcag     780
tggcctcttt actgaaagga agaaaaggtg tttacacaga gaatgagaga ctgatggggg     840
ctgtgatcaa gacccgtttt ttcaaaataa tgctggtgtt aattgcatgt tggttgtcca     900
atatcatcaa tgaaagtctt ttgttctacc ttgaaatgca accagatatc catggaggct     960
ctctgaaacg catccagaat gcagctagga ccacatggtt tataatggga atactgaatc    1020
cagcccaagg acttctcttg tctctggcct tctatggctg acaggatgc agcctggatg    1080
tccatcctcc caagatggtg attcagtggg aaacaatgac tgcctctgct gctgagggca    1140
cgtaccagac ccctgtgcgt tcctgtgtgc cccatcaaaa ccccaggaag gttgtatgtg    1200
tcgggggaca tacttctgat gaggtgctga gcattttgtc tgaagattca gatgccagta    1260
```

```
ctgttgaaat ccatactgca actgggtcct gcaacataaa ggaagttgac tccatttccc    1320
aagcccaggg ggaactctga aggaatggga taggggtcag acaccccctat ttttcaggtt   1380 ctgtgtcttg ttgttttgga ttgtgttctt gctgccacaa tgtatgtatg atctttcaaa    1440
ttccactctg gtcaccatag tggagttcac tgaatatgtc ctttatactg ggagaaacaa    1500
cacatcagaa cttgaagatg gaaagttccc tctagaacag tcagtatcac ctcttgactc    1560
ttaattaccc cttggacttt ttctaaggcc agctgtaatg ctaagtgcca gatccaaatc    1620
catgagaaaa tagttaaata aagtcattgt g                                   1651
```

<210> SEQ ID NO 4
<211> LENGTH: 405
<212> TYPE: PRT
<213> ORGANISM: Mus musculus

<400> SEQUENCE: 4

```
Met Ala Ser Pro Arg Leu Gly Ile Phe Cys Cys Pro Thr Trp Asp Ala
1               5                   10                  15

Ala Thr Gln Leu Val Leu Ser Phe Gln Pro Arg Val Phe His Ala Leu
            20                  25                  30

Cys Leu Gly Ser Gly Thr Leu Arg Leu Val Leu Gly Leu Leu Gln Leu
        35                  40                  45

Leu Ser Gly Arg Arg Ser Val Gly His Arg Ala Pro Ala Thr Ser Pro
    50                  55                  60

Ala Ala Ser Val His Ile Leu Arg Ala Ala Thr Ala Cys Asp Leu Leu
65                  70                  75                  80

Gly Cys Leu Gly Ile Val Ile Arg Ser Thr Val Trp Ile Ala Tyr Pro
                85                  90                  95

Glu Phe Ile Glu Asn Ile Ser Asn Val Asn Ala Thr Asp Ile Trp Pro
            100                 105                 110

Ala Thr Phe Cys Val Gly Ser Ala Met Trp Ile Gln Leu Leu Tyr Ser
        115                 120                 125

Ala Cys Phe Trp Trp Leu Phe Cys Tyr Ala Val Asp Val Tyr Leu Val
    130                 135                 140

Ile Arg Arg Ser Ala Gly Arg Ser Thr Ile Leu Leu Tyr His Ile Met
145                 150                 155                 160

Ala Trp Gly Leu Ala Val Leu Leu Cys Val Glu Gly Ala Val Met Leu
                165                 170                 175

Tyr Tyr Pro Ser Val Ser Arg Cys Glu Arg Gly Leu Asp His Ala Ile
            180                 185                 190

Pro His Tyr Val Thr Thr Tyr Leu Pro Leu Leu Leu Val Leu Val Ala
        195                 200                 205

Asn Pro Ile Leu Phe His Lys Thr Val Thr Ser Val Ala Ser Leu Leu
    210                 215                 220

Lys Gly Arg Lys Gly Val Tyr Thr Glu Asn Glu Arg Leu Met Gly Ala
225                 230                 235                 240

Val Ile Lys Thr Arg Phe Phe Lys Ile Met Leu Val Leu Ile Ala Cys
                245                 250                 255

Trp Leu Ser Asn Ile Ile Asn Glu Ser Leu Leu Phe Tyr Leu Glu Met
            260                 265                 270

Gln Pro Asp Ile His Gly Gly Ser Leu Lys Arg Ile Gln Asn Ala Ala
        275                 280                 285

Arg Thr Thr Trp Phe Ile Met Gly Ile Leu Asn Pro Ala Gln Gly Leu
    290                 295                 300
```

```
Leu Leu Ser Leu Ala Phe Tyr Gly Trp Thr Gly Cys Ser Leu Asp Val
305                 310                 315                 320

His Pro Pro Lys Met Val Ile Gln Trp Glu Thr Met Thr Ala Ser Ala
                325                 330                 335

Ala Glu Gly Thr Tyr Gln Thr Pro Val Arg Ser Cys Val Pro His Gln
            340                 345                 350

Asn Pro Arg Lys Val Val Cys Val Gly Gly His Thr Ser Asp Glu Val
        355                 360                 365

Leu Ser Ile Leu Ser Glu Asp Ser Asp Ala Ser Thr Val Glu Ile His
    370                 375                 380

Thr Ala Thr Gly Ser Cys Asn Ile Lys Glu Val Asp Ser Ile Ser Gln
385                 390                 395                 400

Ala Gln Gly Glu Leu
            405

<210> SEQ ID NO 5
<211> LENGTH: 1723
<212> TYPE: DNA
<213> ORGANISM: Xenopus tropicalis

<400> SEQUENCE: 5
```

| | | | | |
|---|---|---|---|---|
| cggatctgcc tgacactttc tcttctgctc cttcccttgg gagactgcgg ggcttccgag | 60 |
| cgtaaggatg gcttccccca ggctggagac tttctgctgc cccaacaggg atccagctac | 120 |
| tcagttagtg cttgatttcc agcctcagat ctatggctcg ctgtgtatcg gcagtggctt | 180 |
| ggtgagtctc ctgctgacca ttgtccagct gctgcccaag acaaagcagg gttacaggag | 240 |
| gctagggaga gccatgctgc caaaaccttc ctcgtccaga atcttgtttc tagttattat | 300 |
| ctgtgacctg ctgggctgcc taggcatttt aattcgatca tcagtttgga tttcatcccc | 360 |
| aggtttcatt agtaatatgt cactaatgaa cacgtcagac atctggcctt caacttttg | 420 |
| tgttggaagt gcgatgtgga tacagctgtt ttacagtgca agtttctggt ggttattttg | 480 |
| ctatgcaatt gatgcttacc tggtggttcg cagatcagca ggaataagca caattgtttt | 540 |
| gtatcacatg atgacatggg gcctggcact gatgctctgc atcgaaggtg tggctatgct | 600 |
| ttattatcct tccgtttcca attgtgaaaa cggactagaa catgcaatcc ctcattatgt | 660 |
| cacaacctat gcgccacttc ttattgtaat gttcgctaat ccaatcctct ttaggagaac | 720 |
| agtcgctgca gttgcttctt tactgaaagg aagacaaggg atttatacag aaaatgaaag | 780 |
| acggctgggg acagaaattc agctccgttt tttcaagatt atgttggtgt ttatgatctg | 840 |
| ttggacagcc aatattatca atgagaccct tttgttctac ctggaaatgc agccagacat | 900 |
| caacacagat cagctgaaaa atgtcaggaa tgctgctctc atcacatggt ttataatggg | 960 |
| tatactgaat ccaatgcaag gctttctctt cactctggct ttctatgggt ggacaggatg | 1020 |
| gaatgttgat tttaatttca gacagaagga aacagcttgg aacgagtgt ccacatctac | 1080 |
| aataactgaa actgcacaca tggcaccaa tggatcttc ctggattacc ctggctatat | 1140 |
| acagaaccaa aacaagactg aaattggaaa cagccaacaa acagatgaag ctctgagcat | 1200 |
| actgtctgaa ggtaatggga gtatagtgga acgactgaac aggaactccc ccatttatca | 1260 |
| aggatggtag tttgttgatg tcatttcaca tctaggcaat tattccagcc ttgaatactt | 1320 |
| tggtatagta tttgtgcttc ctttggcaga caagcagtca taaaaccttc acaataaaac | 1380 |
| aaataatgtg ctatggagaa gcaattgcaa tggctgaact taaacacaa tctcatactc | 1440 |
| cattatacag ttgcctattg gaaaaataat aaacctgtgt ctcaatttaa cattttgtaa | 1500 |

```
cagataattt gagtgcatgt tgcctgccac tgatgttgtg taatcaagat gggatataaa    1560
gcccttttta agtctctgca tcttttgctg tactcaggga aataatatgg ctgaatagga    1620
ctagtccata aacagaaata actttggatg ttaatgggat agaggaagat atggtaattt    1680
gctatttcaa taaatatttt tttgtacaaa aaaaaaaaaa aaa                      1723
```

```
<210> SEQ ID NO 6
<211> LENGTH: 400
<212> TYPE: PRT
<213> ORGANISM: Xenopus tropicalis

<400> SEQUENCE: 6

Met Ala Ser Pro Arg Leu Glu Thr Phe Cys Cys Pro Asn Arg Asp Pro
1               5                   10                  15

Ala Thr Gln Leu Val Leu Asp Phe Gln Pro Gln Ile Tyr Gly Ser Leu
            20                  25                  30

Cys Ile Gly Ser Gly Leu Val Ser Leu Leu Thr Ile Val Gln Leu
        35                  40                  45

Leu Pro Lys Thr Lys Gln Gly Tyr Arg Arg Leu Gly Arg Ala Met Leu
    50                  55                  60

Pro Lys Pro Ser Ser Arg Ile Leu Phe Leu Val Ile Ile Cys Asp
65                  70                  75                  80

Leu Leu Gly Cys Leu Gly Ile Leu Ile Arg Ser Ser Val Trp Ile Ser
                85                  90                  95

Ser Pro Gly Phe Ile Ser Asn Met Ser Leu Met Asn Thr Ser Asp Ile
            100                 105                 110

Trp Pro Ser Thr Phe Cys Val Gly Ser Ala Met Trp Ile Gln Leu Phe
        115                 120                 125

Tyr Ser Ala Ser Phe Trp Trp Leu Phe Cys Tyr Ala Ile Asp Ala Tyr
    130                 135                 140

Leu Val Val Arg Arg Ser Ala Gly Ile Ser Thr Ile Val Leu Tyr His
145                 150                 155                 160

Met Met Thr Trp Gly Leu Ala Leu Met Leu Cys Ile Glu Gly Val Ala
                165                 170                 175

Met Leu Tyr Tyr Pro Ser Val Ser Asn Cys Glu Asn Gly Leu Glu His
            180                 185                 190

Ala Ile Pro His Tyr Val Thr Thr Tyr Ala Pro Leu Leu Ile Val Met
        195                 200                 205

Phe Ala Asn Pro Ile Leu Phe Arg Arg Thr Val Ala Ala Val Ala Ser
    210                 215                 220

Leu Leu Lys Gly Arg Gln Gly Ile Tyr Thr Glu Asn Glu Arg Arg Leu
225                 230                 235                 240

Gly Thr Glu Ile Gln Leu Arg Phe Phe Lys Ile Met Leu Val Phe Met
                245                 250                 255

Ile Cys Trp Thr Ala Asn Ile Ile Asn Glu Thr Leu Leu Phe Tyr Leu
            260                 265                 270

Glu Met Gln Pro Asp Ile Asn Thr Asp Gln Leu Lys Asn Val Arg Asn
        275                 280                 285

Ala Ala Leu Ile Thr Trp Phe Ile Met Gly Ile Leu Asn Pro Met Gln
    290                 295                 300

Gly Phe Leu Phe Thr Leu Ala Phe Tyr Gly Trp Thr Gly Trp Asn Val
305                 310                 315                 320

Asp Phe Asn Phe Arg Gln Lys Glu Thr Ala Trp Glu Arg Val Ser Thr
                325                 330                 335
```

```
Ser Thr Ile Thr Glu Thr Ala His Asn Gly Thr Asn Gly Ser Phe Leu
        340                 345                 350

Asp Tyr Pro Gly Tyr Ile Gln Asn Gln Asn Lys Thr Glu Ile Gly Asn
        355                 360                 365

Ser Gln Gln Thr Asp Glu Ala Leu Ser Ile Leu Ser Glu Gly Asn Gly
        370                 375                 380

Ser Ile Val Glu Arg Leu Asn Arg Asn Ser Pro Ile Tyr Gln Gly Trp
385                 390                 395                 400

<210> SEQ ID NO 7
<211> LENGTH: 1585
<212> TYPE: DNA
<213> ORGANISM: Bos taurus

<400> SEQUENCE: 7
atggcctctc cgcgactagg caccttctgc tgccccacgc gggacgccgc cacgcagctc      60
gcgctgggct ccagccgcg ggcttttccac gcgctgtgtc tgggtagcgg cgcgctccgc     120
ctggcgctcg gcctcctgca gctgcggccc gggcgccggc ccgcgggccc cgggatcgcc     180
tcagcctcgc cggcgacctc ggcccgcgtc cccgcctccg tgcgcatcgt gcgcgccgca     240
accgcttgcg acctgcttgg ctgcctgggt atcgcggtcc gatctgcggt gtggttaggg     300
tttccgagtt cgtggacga catctctgcc gtgaacaaca cagatgtgtg gcctgccgtc     360
ttctgcgtgg ggagtgcact ctggatccag ctgctgtaca gtgcctgctt ctggtggtgg     420
ttctgctacg cagtggatgc ctacctggtg atccagaggt cggctggaca gagcaccatc     480
ctgctgtacc acctcatgac ctggggcctg gctgccctgc tgagcgtgga gggtgccctc     540
atgctgtact atccttccat ggccaggtgc gagaggggcc tggagcatgc catcccccac     600
tacatcacca cgtacttgcc gctgctactg gtcctggtgg gcaacccat cctatttcga      660 aagacagtga ccgcagtggc ctccttactg aagggaagac aaggcattta cacggagaac     720
gagagacgca tgggagccag gatcaagacc cgattcttca aaataatgct ggttttcatt     780
gtttgctggt tctcaaatgt catcaacgaa agccttttgt tctatcttga aatgcaacca     840
gatatcaaca gcagctcttt gaaacaggtc agaaacgcag ccaagaccac gtggttcatg     900
atggggatcc tgaatccagc ccaaggtttc ctgttgtccc tggccttcta tggctggacg     960
ggctgccgcc tgacgcttcc aggtccagc aaggagatcc agtgggactc gatgaccacc     1020
tcggccaccg agggggcgcc ccctcccccc gggggccccc aagagcccgg ggaaggcccc     1080
gctcccaaga aggagcttcc gggcggcacg cacacttccg atgaggcctt gagcttgctt     1140
tctgaaggtt ccggcggcag caccattgaa atccacatcg caagcgggtc ccgcggcgga     1200
aaggcccccg actctcttcc gaaagtccaa ggaaccccgt agagaggacg agacagaggg     1260
ctctggaccc tgtgtgtatt ttcagacgcg acggttctca tcccttatga cggtaccctt     1320
gcccttcagt cagcacactg cggggtgtag cgtccccccc aactgaatct tcctgccatc     1380
acagttaaca gagtgttccc tggcagcctc tgtgtgatgc agaggccac cgtgagcctg     1440 tgcttggaaa ggaaaggcag attcccttgg agcccagcag cttgtccgga gtctccgtgg     1500
acgttcgttt ctctgatctg gctgtaatgt caacgccaga tccaggtcct tggaagagtt     1560
aataaataac aataattaaa aaaaa                                           1585

<210> SEQ ID NO 8
<211> LENGTH: 413
<212> TYPE: PRT
<213> ORGANISM: Bos taurus
```

```
<400> SEQUENCE: 8

Met Ala Ser Pro Arg Leu Gly Thr Phe Cys Cys Pro Thr Arg Asp Ala
1               5                   10                  15

Ala Thr Gln Leu Ala Leu Gly Phe Gln Pro Arg Ala Phe His Ala Leu
            20                  25                  30

Cys Leu Gly Ser Gly Ala Leu Arg Leu Ala Leu Gly Leu Leu Gln Leu
            35                  40                  45

Arg Pro Gly Arg Arg Pro Ala Gly Pro Gly Ile Ala Ser Ala Ser Pro
        50                  55                  60

Ala Thr Ser Ala Arg Val Pro Ala Ser Val Arg Ile Val Arg Ala Ala
65              70                  75                  80

Thr Ala Cys Asp Leu Leu Gly Cys Leu Gly Ile Ala Val Arg Ser Ala
                85                  90                  95

Val Trp Leu Gly Phe Pro Ser Phe Val Asp Asp Ile Ser Ala Val Asn
                100                 105                 110

Asn Thr Asp Val Trp Pro Ala Val Phe Cys Val Gly Ser Ala Leu Trp
            115                 120                 125

Ile Gln Leu Leu Tyr Ser Ala Cys Phe Trp Trp Trp Phe Cys Tyr Ala
130                 135                 140

Val Asp Ala Tyr Leu Val Ile Gln Arg Ser Ala Gly Gln Ser Thr Ile
145                 150                 155                 160

Leu Leu Tyr His Leu Met Thr Trp Gly Leu Ala Ala Leu Leu Ser Val
                165                 170                 175

Glu Gly Ala Leu Met Leu Tyr Tyr Pro Ser Met Ala Arg Cys Glu Arg
            180                 185                 190

Gly Leu Glu His Ala Ile Pro His Tyr Ile Thr Thr Tyr Leu Pro Leu
        195                 200                 205

Leu Leu Val Leu Val Gly Asn Pro Ile Leu Phe Arg Lys Thr Val Thr
210                 215                 220

Ala Val Ala Ser Leu Leu Lys Gly Arg Gln Gly Ile Tyr Thr Glu Asn
225                 230                 235                 240

Glu Arg Arg Met Gly Ala Arg Ile Lys Thr Arg Phe Phe Lys Ile Met
                245                 250                 255

Leu Val Phe Ile Val Cys Trp Phe Ser Asn Val Ile Asn Glu Ser Leu
            260                 265                 270

Leu Phe Tyr Leu Glu Met Gln Pro Asp Ile Asn Ser Ser Ser Leu Lys
        275                 280                 285

Gln Val Arg Asn Ala Ala Lys Thr Thr Trp Phe Met Met Gly Ile Leu
    290                 295                 300

Asn Pro Ala Gln Gly Phe Leu Leu Ser Leu Ala Phe Tyr Gly Trp Thr
305                 310                 315                 320

Gly Cys Arg Leu Thr Leu Pro Gly Pro Ser Lys Glu Ile Gln Trp Asp
                325                 330                 335

Ser Met Thr Thr Ser Ala Thr Glu Gly Ala Pro Pro Ser Pro Gly Gly
            340                 345                 350

Pro Gln Glu Pro Gly Glu Gly Pro Ala Pro Lys Lys Glu Leu Pro Gly
        355                 360                 365

Gly Thr His Thr Ser Asp Glu Ala Leu Ser Leu Leu Ser Glu Gly Ser
    370                 375                 380

Gly Gly Ser Thr Ile Glu Ile His Ile Ala Ser Gly Ser Arg Gly Gly
385                 390                 395                 400

Lys Ala Pro Asp Ser Leu Pro Lys Val Gln Gly Thr Pro
```

<210> SEQ ID NO 9
<211> LENGTH: 1612
<212> TYPE: DNA
<213> ORGANISM: Rattus norvegicus

<400> SEQUENCE: 9

```
gcccagcacc tgaccaggaa aagctgtggg ttctgcagac cagagaccgg tccgtgagca      60
agaccaatgg cctccccgcg cctgggaatc ttctgctgcc cttcgtggga tgcagccaca     120
cagctggtgc tgaccttcca accgcgggtg ttccatgcgc tgtgtctggg cagcggcgcc     180
ctccgcctgg tgcttggcct ccttcagctc ctaacagggc gccgatctgt tggtcacagg     240
gcgcctgcga caaccccagc agcctcagtc cacatccttc gtgctgccac cgcctgtgat     300
ttgcttggct gcctgggaat cgttatcagg tccacagtgt ggatagccta cccagaattc     360
attgaaaaca tttccaatat gaatggaaca gacatttggc ctactgcttt ctgtgtcggg     420
agtgcaatgt ggatccagct gttgtacagt gcctgcttct ggtggctctt ctgctatgca     480
gttgatgtat acttggtgat caggagatca gcaggacgga gcaccatcct gctgtaccac     540
atcatggcct ggggcctgcc tgtgctgctc tgtgtggaag tgcagtcat gctttattac      600
ccttctgtgt ccaggtgtga gagaggcctg gaccatgcca tcccccatta tgtcaccaca     660
tacttgccac ttatgcttgt ccttgtggcc aacccgatcc tgtttcacaa gacagtgatt     720
tcagtggcct ctttactgaa aggacgaaaa ggtgtttata cagagaatga gagattgatg     780
ggggccgtga tcaagacccg ttttttcaaa ataatgctgg tgttaattgc atgttggttg     840
tccaatatca tcaatgaatg tcttttgttc taccttgaaa tgcaaccaga tacccatgga     900
ggctctctga aacgcatcca gaatgcagcc aggaccacat ggtttattat gggaatattg     960
aatccatctc aaggacttct cttgtctctg gccttctatg ctggacagg atgcagcctg    1020
gatgtccatg ctcccaagat ggtgattcag tgggaaacaa tgactgcctc ggctgctgag    1080
ggcacatatc agacccctga gggttcctgt gtgccccatc aaaacccag gaaggtggtg    1140
tgtgttgggg ggcacacttc tgatgaggtg ctgagtattt tgtctgaagg ttcggatgct    1200
agcactgttg aaatccatac tgcaactggg tcccacaaca taaggaagt tgactccatt    1260
tcccaagccc aggggatct ctgaatggat gggatggggg ccagacatcc ctgtttttca    1320
ggttctgtgt cttgttgttt tggattgtgt tcttgccttc cttcctatca cagtgctgcc    1380
atgatgtagc atccttcaaa ttccactttg gtcaccatag aggagctcac tgaggatggc    1440
ctttatgctg ggagaaacaa cacaccagaa cttggacatg gaaaatttcc tctagaacat    1500
tcagtgtcac ctcttgactt ttaattaccc cttggacttt tactaaggcc agttgtagtg    1560
cttaagtgcc agacccaaat tcttgagaaa atagttaaat aaagtcattg tg            1612
```

<210> SEQ ID NO 10
<211> LENGTH: 405
<212> TYPE: PRT
<213> ORGANISM: Rattus norvegicus

<400> SEQUENCE: 10

Met Ala Ser Pro Arg Leu Gly Ile Phe Cys Cys Pro Ser Trp Asp Ala
1               5                   10                  15

Ala Thr Gln Leu Val Leu Thr Phe Gln Pro Arg Val Phe His Ala Leu
            20                  25                  30

Cys Leu Gly Ser Gly Ala Leu Arg Leu Val Leu Gly Leu Leu Gln Leu

```
            35                  40                  45
Leu Thr Gly Arg Arg Ser Val Gly His Arg Ala Pro Ala Thr Thr Pro
 50                  55                  60

Ala Ala Ser Val His Ile Leu Arg Ala Ala Thr Ala Cys Asp Leu Leu
 65                  70                  75                  80

Gly Cys Leu Gly Ile Val Ile Arg Ser Thr Val Trp Ile Ala Tyr Pro
                 85                  90                  95

Glu Phe Ile Glu Asn Ile Ser Asn Met Asn Gly Thr Asp Ile Trp Pro
                100                 105                 110

Thr Ala Phe Cys Val Gly Ser Ala Met Trp Ile Gln Leu Leu Tyr Ser
                115                 120                 125

Ala Cys Phe Trp Trp Leu Phe Cys Tyr Ala Val Asp Val Tyr Leu Val
                130                 135                 140

Ile Arg Arg Ser Ala Gly Arg Ser Thr Ile Leu Leu Tyr His Ile Met
145                 150                 155                 160

Ala Trp Gly Leu Pro Val Leu Leu Cys Val Glu Gly Ala Val Met Leu
                165                 170                 175

Tyr Tyr Pro Ser Val Ser Arg Cys Glu Arg Gly Leu Asp His Ala Ile
                180                 185                 190

Pro His Tyr Val Thr Thr Tyr Leu Pro Leu Met Leu Val Leu Val Ala
                195                 200                 205

Asn Pro Ile Leu Phe His Lys Thr Val Ile Ser Val Ala Ser Leu Leu
210                 215                 220

Lys Gly Arg Lys Gly Val Tyr Thr Glu Asn Glu Arg Leu Met Gly Ala
225                 230                 235                 240

Val Ile Lys Thr Arg Phe Phe Lys Ile Met Leu Val Leu Ile Ala Cys
                245                 250                 255

Trp Leu Ser Asn Ile Ile Asn Glu Cys Leu Leu Phe Tyr Leu Glu Met
                260                 265                 270

Gln Pro Asp Thr His Gly Gly Ser Leu Lys Arg Ile Gln Asn Ala Ala
                275                 280                 285

Arg Thr Thr Trp Phe Ile Met Gly Ile Leu Asn Pro Ser Gln Gly Leu
                290                 295                 300

Leu Leu Ser Leu Ala Phe Tyr Gly Trp Thr Gly Cys Ser Leu Asp Val
305                 310                 315                 320

His Ala Pro Lys Met Val Ile Gln Trp Glu Thr Met Thr Ala Ser Ala
                325                 330                 335

Ala Glu Gly Thr Tyr Gln Thr Pro Glu Gly Ser Cys Val Pro His Gln
                340                 345                 350

Asn Pro Arg Lys Val Val Cys Val Gly Gly His Thr Ser Asp Glu Val
                355                 360                 365

Leu Ser Ile Leu Ser Glu Gly Ser Asp Ala Ser Thr Val Glu Ile His
                370                 375                 380

Thr Ala Thr Gly Ser His Asn Ile Lys Glu Val Asp Ser Ile Ser Gln
385                 390                 395                 400

Ala Gln Gly Asp Leu
                405

<210> SEQ ID NO 11
<211> LENGTH: 425
<212> TYPE: DNA
<213> ORGANISM: Ornithorhynchus anatinus

<400> SEQUENCE: 11
```

```
atggcttctc ctaggctgga gaccttctgc tgccccaacc gggatgcagc cacacaactg      60
atgttgaatt ttcagcctca aattttcaac ggcgtctgcc tgggaagtgc ttcagccaac     120
ctcctgctca gcatcttcca gctccttccc aaacgaggcc aaggcccag gaaactaact      180 caaacctcct ctgccagcat cctgctcttc atctctgcct gtgaccttct ggctgtctg     240 ggtgtaatat tcaggtccac agtgtggtta ggattcccag atttcgttgg aaacatctcg     300
gtggtgaatg ggacagatgg atggccctca gctttctgtg tagggagtgc aatgtggatt     360
caactgctgt acagtgcttg cttctggtgg cttgtttgct atgctgtaga tgccttacct     420
tgctt                                                                 425
```

<210> SEQ ID NO 12
<211> LENGTH: 141
<212> TYPE: PRT
<213> ORGANISM: Ornithorhynchus anatinus

<400> SEQUENCE: 12

```
Met Ala Ser Pro Arg Leu Glu Thr Phe Cys Cys Pro Asn Arg Asp Ala
1               5                   10                  15

Ala Thr Gln Leu Met Leu Asn Phe Gln Pro Gln Ile Phe Asn Gly Val
            20                  25                  30

Cys Leu Gly Ser Ala Ser Ala Asn Leu Leu Leu Ser Ile Phe Gln Leu
        35                  40                  45

Leu Pro Lys Arg Gly Gln Gly Pro Arg Lys Leu Thr Gln Thr Ser Ser
    50                  55                  60

Ala Ser Ile Leu Leu Phe Ile Ser Ala Cys Asp Leu Leu Gly Cys Leu
65                  70                  75                  80

Gly Val Ile Phe Arg Ser Thr Val Trp Leu Gly Phe Pro Asp Phe Val
                85                  90                  95

Gly Asn Ile Ser Val Val Asn Gly Thr Asp Gly Trp Pro Ser Ala Phe
            100                 105                 110

Cys Val Gly Ser Ala Met Trp Ile Gln Leu Leu Tyr Ser Ala Cys Phe
        115                 120                 125

Trp Trp Leu Val Cys Tyr Ala Val Asp Ala Leu Pro Cys
    130                 135                 140
```

<210> SEQ ID NO 13
<211> LENGTH: 1800
<212> TYPE: DNA
<213> ORGANISM: Xenopus laevis

<400> SEQUENCE: 13

```
cacgggaacc cctgacccag aattgagccg agcgagacaa agacgtagct gggggggat      60 tgtaaaggca catgatcgca ttctccccgt gatcagcagc gctgtagcat gaagctcaga    120
gggtagcgtg catctgcctc gacgctttct cttctcttct gccttttgg agactgcggg     180 gctcttgagc ctataaggat ggcttccccc aggctggaga cttctgctg ccccaacagg      240 gatgcagcta cacagttagt gcttgatttc agcctcagg tctatggctc gctgtgtctc     300
ggcagcggct tggtgagtct cctgctgacc attgtccagc tgttgcccaa gacaaagcac    360
ggctacagga ggcacgggag atccatgctg ccaaaacctt cttcctccag gatcttgttt    420
ctagttattg tctgtgacct actgggctgc ctaggaattt taattcgatc atcggtatgg    480
atatcatccc caggtttcat tagtaatatg tcactaatga atacttcaga catctggcct    540
tcaagctttt gcgttggaag tgcgatgtgg atacagctgt tttacagtgc aagtttctgg    600
```

-continued

```
tggttatttt gctatgcaat tgatgcttac ctagttgttc gcagatctgc aggaataagc    660
acaattgtgt tgtatcacat gatgacgtgg ggcctggcac ttatgctctg cgttgaaggt    720
gtggctatgc tttactatcc ttcagtttcc aattgtgaaa atggactaga acatgcaatt    780
cctcattatg tcacaaccta tgcaccactt cttatcgtaa tgtttgcgaa tccaatcctc    840
tttcgaagaa cagttgcagc agttgcttct ttactgaaag gaagacaagg aatttataca    900
gagaatgaaa acggctggg acagaaatt caactccgtt ttttcaagat catgttggtg    960
tttatgatct gttggacagc taatattatc aatgagactc ttttgttcta cctggaaatg   1020
cagccagaca tcaaaacgga tcagctaaag aatgtcagga atgcagcact catcacatgg   1080
tttataatgg gtatactgaa tccaatgcaa ggctttctct tcactttggc tttctacggg   1140
tggacagggt ggaatgttga ctttaatttc agacaaaagg aaacagcttg gaacgagta   1200
tctacatctt cattgactga agctgcacac aatggcacca atggatcttt cctggattac   1260
cctggctaca tacagaacca aaacaagact gaaattggaa acagtcaaca aacagatgag   1320
gctttgagca tactatctga aggtaatggg agtatagtgg aacgactaag caggaactcc   1380
cctgtatatc aaggatggta gtttccagat gtcatttat atctaggcta ttattccacc   1440
ttgattactt tggtgtagta ttgttgctcc cgttggcggc aagaagtcat cactctatct   1500
caataatggg tacctggcaa tatgaagaag caattgcaat gactgaattt aaaacacatt   1560
ctcataatca cttcacaatt tcaaatatta aacttgtgtc tccattaaac attttgtaac   1620
agataatttg agtgcatgtt gcctgccact gtcgtcatat aatcaagatg ggatatgtag   1680
tctgcatcgt ttgctataat tcataaattg aaatggatgt taaggggata gaggaatttt   1740
ggtaaaatta ataaaaatat ttttatacac gtcaaaaaaa aaaaaaaaaa aaaaaaaaa    1800
```

<210> SEQ ID NO 14
<211> LENGTH: 400
<212> TYPE: PRT
<213> ORGANISM: Xenopus laevis

<400> SEQUENCE: 14

```
Met Ala Ser Pro Arg Leu Glu Thr Phe Cys Cys Pro Asn Arg Asp Ala
1               5                  10                  15

Ala Thr Gln Leu Val Leu Asp Phe Gln Pro Gln Val Tyr Gly Ser Leu
            20                  25                  30

Cys Leu Gly Ser Gly Leu Val Ser Leu Leu Thr Ile Val Gln Leu
        35                  40                  45

Leu Pro Lys Thr Lys His Gly Tyr Arg Arg His Gly Arg Ser Met Leu
    50                  55                  60

Pro Lys Pro Ser Ser Arg Ile Leu Phe Leu Val Ile Val Cys Asp
65                  70                  75                  80

Leu Leu Gly Cys Leu Gly Ile Leu Ile Arg Ser Ser Val Trp Ile Ser
                85                  90                  95

Ser Pro Gly Phe Ile Ser Asn Met Ser Leu Met Asn Thr Ser Asp Ile
            100                 105                 110

Trp Pro Ser Ser Phe Cys Val Gly Ser Ala Met Trp Ile Gln Leu Phe
        115                 120                 125

Tyr Ser Ala Ser Phe Trp Trp Leu Phe Cys Tyr Ala Ile Asp Ala Tyr
    130                 135                 140

Leu Val Val Arg Arg Ser Ala Gly Ile Ser Thr Ile Val Leu Tyr His
145                 150                 155                 160

Met Met Thr Trp Gly Leu Ala Leu Met Leu Cys Val Glu Gly Val Ala
```

```
                    165                 170                 175
Met Leu Tyr Tyr Pro Ser Val Ser Asn Cys Glu Asn Gly Leu Glu His
            180                 185                 190

Ala Ile Pro His Tyr Val Thr Thr Tyr Ala Pro Leu Leu Ile Val Met
        195                 200                 205

Phe Ala Asn Pro Ile Leu Phe Arg Arg Thr Val Ala Ala Val Ala Ser
    210                 215                 220

Leu Leu Lys Gly Arg Gln Gly Ile Tyr Thr Glu Asn Glu Arg Arg Leu
225                 230                 235                 240

Gly Thr Glu Ile Gln Leu Arg Phe Phe Lys Ile Met Leu Val Phe Met
            245                 250                 255

Ile Cys Trp Thr Ala Asn Ile Ile Asn Glu Thr Leu Leu Phe Tyr Leu
        260                 265                 270

Glu Met Gln Pro Asp Ile Lys Thr Asp Gln Leu Lys Asn Val Arg Asn
    275                 280                 285

Ala Ala Leu Ile Thr Trp Phe Ile Met Gly Ile Leu Asn Pro Met Gln
290                 295                 300

Gly Phe Leu Phe Thr Leu Ala Phe Tyr Gly Trp Thr Gly Trp Asn Val
305                 310                 315                 320

Asp Phe Asn Phe Arg Gln Lys Glu Thr Ala Trp Glu Arg Val Ser Thr
            325                 330                 335

Ser Ser Leu Thr Glu Ala Ala His Asn Gly Thr Asn Gly Ser Phe Leu
        340                 345                 350

Asp Tyr Pro Gly Tyr Ile Gln Asn Gln Asn Lys Thr Glu Ile Gly Asn
    355                 360                 365

Ser Gln Gln Thr Asp Glu Ala Leu Ser Ile Leu Ser Glu Gly Asn Gly
370                 375                 380

Ser Ile Val Glu Arg Leu Ser Arg Asn Ser Pro Val Tyr Gln Gly Trp
385                 390                 395                 400

<210> SEQ ID NO 15
<211> LENGTH: 1622
<212> TYPE: DNA
<213> ORGANISM: Gallus gallus

<400> SEQUENCE: 15
agcacacgct gcctttgga agcaacagcg gcggcttctg cttgcgggcc cccttcgcca    60
gccgggtgct tcatggcctc tcccaggtta gaaacctact gctgcccaa cagggatgca   120 gccacgcagc tcgtgatgaa cttccagccc caggtcttct gtggggtctg catcggcagc   180
gcctctgcca gcctgctgct gaccatcctg cagctcctgc cgaagaaggg gcagagcctg   240
cggaagatgc ccaaagcctc ctcctcctcc accattcttc tccttatctc cgtctgtgac   300
atccttggtg gctcaggtgt gatcttcaga tcgagtgtct ggttgggctt cccgagcttc   360
attgccaaca tctcagtggc caacgggact gacatatggc cctctgcctt ctgcgtgggc   420
agcgcgatgt ggatccagct gttgtatagt gctggcttct ggtggttatt ttgctatgct   480
gtcgattctt acttggtggt aagaagatca gcaggacgga gtacaattgt gctgtaccat   540
atgatggcct gggggctggc agttttgctc tgcatggagg cgtcatgct gctttactac   600 ccgtcccttt ccagctgtga agaggcctg agcatgcaa tcccacatta tcacaaacc   660 tatgccccac tcctgctggt gctggtggtc aacccagtcc tgttcagaag acggtgact   720 gcagttgcct ctttactgaa agggagacaa gggatttaca cagagaatga gagcggctg   780 gggacagaga tccagatgcg cttttttcaag attatgctgg tattcactgt tgctggtca   840
```

```
tctaatatca tcaacgagag ccttttgttc tatctcgaaa tgcagccaga tatcaatgaa      900
acacctttga aaacattag aagtgctgca ttgatcacat ggattataat gggagttctt       960
aatccgatgc aaggcttcct cttcacatta gctttctatg ctggacagg atggaaagtg      1020
gacctgaaat ggcagaagag agaaataccc tgggaatcga tgtcctcatc aacagtgggc     1080
gacaatgact atccctcacc agtgaactac caaagcaacg tccacgattc aaagaagata     1140
tcgaccactg acagccagca gactgatgag gctattagca tgttgtctga aggtaacact     1200
agcagtgatg acaggttgac caggagctct gccatctacc agggctggta gcttaaaggt     1260
ggagagctga atctcacttc tcccattgtc aagactcaca aaaccatggc actgtgtgaa     1320
ccactgctca ctctggaatt tttgcctaat ggttttggc taatggctca atgtaatttc     1380
ctgtagcttt tgttcgtgtg tgagactgtg tatgatgcag agaaatgatg gttaatgtct     1440
tcacttgcct tataggagat gtgtagcaag gtacaaaggc ctgatcgctt ttagcaggcg     1500
tatgtctctg cagggatcta tgttacttat gattcatctg ttttctttca atctctcctg     1560
taacctccgt atggtagaag agtcttttgt ttaaataaac agactattaa tatgttggtt     1620
tt                                                                    1622
```

<210> SEQ ID NO 16
<211> LENGTH: 392
<212> TYPE: PRT
<213> ORGANISM: Gallus gallus

<400> SEQUENCE: 16

```
Met Ala Ser Pro Arg Leu Glu Thr Tyr Cys Cys Pro Asn Arg Asp Ala
1               5                   10                  15

Ala Thr Gln Leu Val Met Asn Phe Gln Pro Gln Val Phe Cys Gly Val
            20                  25                  30

Cys Ile Gly Ser Ala Ser Ala Ser Leu Leu Leu Thr Ile Leu Gln Leu
        35                  40                  45

Leu Pro Lys Lys Gly Gln Ser Leu Arg Lys Met Pro Lys Ala Ser Ser
    50                  55                  60

Ser Ser Thr Ile Leu Leu Ile Ser Val Cys Asp Ile Leu Gly Gly
65                  70                  75                  80

Ser Gly Val Ile Phe Arg Ser Ser Val Trp Leu Gly Phe Pro Ser Phe
                85                  90                  95

Ile Ala Asn Ile Ser Val Ala Asn Gly Thr Asp Ile Trp Pro Ser Ala
            100                 105                 110

Phe Cys Val Gly Ser Ala Met Trp Ile Gln Leu Leu Tyr Ser Ala Gly
        115                 120                 125

Phe Trp Trp Leu Phe Cys Tyr Ala Val Asp Ser Tyr Leu Val Val Arg
    130                 135                 140

Arg Ser Ala Gly Arg Ser Thr Ile Val Leu Tyr His Met Met Ala Trp
145                 150                 155                 160

Gly Leu Ala Val Leu Leu Cys Met Glu Gly Val Met Leu Leu Tyr Tyr
                165                 170                 175

Pro Ser Leu Ser Ser Cys Glu Arg Gly Leu Glu His Ala Ile Pro His
            180                 185                 190

Tyr Ile Thr Thr Tyr Ala Pro Leu Leu Leu Val Leu Val Asn Pro
        195                 200                 205

Val Leu Phe Arg Arg Thr Val Thr Ala Val Ala Ser Leu Leu Lys Gly
    210                 215                 220
```

```
            Arg Gln Gly Ile Tyr Thr Glu Asn Glu Arg Arg Leu Gly Thr Glu Ile
            225                 230                 235                 240

Gln Met Arg Phe Phe Lys Ile Met Leu Val Phe Thr Val Cys Trp Ser
                            245                 250                 255

Ser Asn Ile Ile Asn Glu Ser Leu Leu Phe Tyr Leu Glu Met Gln Pro
                        260                 265                 270

Asp Ile Asn Glu Thr Pro Leu Lys Asn Ile Arg Ser Ala Ala Leu Ile
                    275                 280                 285

Thr Trp Ile Ile Met Gly Val Leu Asn Pro Met Gln Gly Phe Leu Phe
                290                 295                 300

Thr Leu Ala Phe Tyr Gly Trp Thr Gly Trp Lys Val Asp Leu Lys Trp
            305                 310                 315                 320

Gln Lys Arg Glu Ile Pro Trp Glu Ser Met Ser Ser Thr Val Gly
                            325                 330                 335

Asp Asn Asp Tyr Pro Ser Pro Val Asn Tyr Gln Ser Asn Val His Asp
                            340                 345                 350

Ser Lys Lys Ile Ser Thr Thr Asp Ser Gln Thr Asp Glu Ala Ile
                        355                 360                 365

Ser Met Leu Ser Glu Gly Asn Thr Ser Ser Asp Asp Arg Leu Thr Arg
                370                 375                 380

Ser Ser Ala Ile Tyr Gln Gly Trp
            385                 390

<210> SEQ ID NO 17
<211> LENGTH: 1712
<212> TYPE: DNA
<213> ORGANISM: Danio rerio

<400> SEQUENCE: 17
gctcgtgatc cagcagtcgc acttcaggcc agcacaatga atgaatgagc ttctgcgctc      60
tgcttctgct ccatcttcat cttcagcatt attttcatct tcattttctt catcttcttc     120
atcttcttca tcatcttcat catcatggcc tctccgcgcc tcgagacctt ctgctgcccg     180
aaccgcgacg cgccaccgga gctggtggtg gcttccagc cgctgttctt cggggtgatg      240
tgtgtgtgca gcgccgctct gagctccggc ctggcgctgc tgcagattct gcccaagcgg     300
aggagcttca gaccgcaggc gcacagcagc agagccgcgt cctccagccg catcctcacc     360
atcatcagcg tctgcgacat actgggctgc agggatca tcatccgctc ctcgctgtgg       420
atcggtttgc caaacctcgt ctcggagatc tcagatggaa acagcagctc ggtgtggccg     480
caggtcttct gtgttggcag cgcgatgtgg atacagctgt tctttagcgc ctccttctgg     540
tggactttct gctacgccgt cgacgtcttc ctggtggtca agatctgc aggcatcagc       600 accatcatcc tctaccacat gatcacgtgg ggtttgacat tgctgctgtg tgtggaagga    660
gtcgccatgc tttactaccc gtccatctcc agttgtgaga cggtcttca acatgccatt     720 cctcattacg tcaccacata cgctccaatg ctgctggtgc tggcggtcaa tccagtactc     780
ttcaccagga ccgtatccgc cgtgacgtct ctgctcaagg gtcagcaggg catttacacg     840
gagaacgaga ggagactcgg ctctgagatc aaaatacgct tcttcaagat catgctggtg    900
ttcttcattt gctggctgcc caacatcatc aacgagagtc tgctgtttta tctggagatg    960
caggacgatg ttaaatccag cgatctgaag aacattcgca acgctgcgct aatcacatgg    1020
ttcatcatgg gaatcctgaa ccccatgcag ggcttcctga acacgctggc gtttcacggc    1080
tggacgggtc tggatctgga cttcagtcgg cagagacgtc gcgagctgcc ctgggactcg    1140
```

-continued

```
gcctccacat ctcttgctgg aggattcact cctgtggtcg gatcatcttt aatttaccag    1200
agccacgtgc aggagatcaa gaaaaacctg agcgccaacg gaggccagca gccgtcggac    1260
gccatcagtg tgctttctga agattcagag tcgagtacgg tagaaatcca catttccagc    1320
gagcagcgag aatttgagga gctgaagcga acggagcat cgtgggagat ttctacaggc     1380
taaagattca gaagagtcat tgctgatca gcgattccct gaacaaatgc ttctgtctga     1440
ggcccgtttc tgttcaagat ttctctaaga acttctccag actttaagtt ttaaagcttt    1500
aacctgcact ttgagcaata tctctggtta aactgcgttc ctgacatcac tctaggctac    1560
cttttgagtg ttttgtttta atcctctgta attcagtgta cactattacg tgcttcgggt    1620
cgccttcact aaagctctac aataaagcag atccattgaa cttcaaaaaa aaaaaaaaaa    1680
aaaaaaaaaa aaaaaaaaaa aaaaaaaaaa aa                                  1712
```

<210> SEQ ID NO 18
<211> LENGTH: 412
<212> TYPE: PRT
<213> ORGANISM: Danio rerio

<400> SEQUENCE: 18

```
Met Ala Ser Pro Arg Leu Glu Thr Phe Cys Cys Pro Asn Arg Asp Gly
  1               5                  10                  15

Ala Thr Glu Leu Val Val Gly Phe Gln Pro Leu Phe Phe Gly Val Met
             20                  25                  30

Cys Val Cys Ser Ala Ala Leu Ser Ser Gly Leu Ala Leu Leu Gln Ile
         35                  40                  45

Leu Pro Lys Arg Arg Ser Phe Arg Pro Gln Ala His Ser Ser Arg Ala
     50                  55                  60

Ala Ser Ser Ser Arg Ile Leu Thr Ile Ile Ser Val Cys Asp Ile Leu
 65                  70                  75                  80

Gly Cys Thr Gly Ile Ile Ile Arg Ser Ser Leu Trp Ile Gly Leu Pro
                 85                  90                  95

Asn Leu Val Ser Glu Ile Ser Asp Gly Asn Ser Ser Ser Val Trp Pro
            100                 105                 110

Gln Val Phe Cys Val Gly Ser Ala Met Trp Ile Gln Leu Phe Phe Ser
        115                 120                 125

Ala Ser Phe Trp Trp Thr Phe Cys Tyr Ala Val Asp Val Phe Leu Val
    130                 135                 140

Val Lys Arg Ser Ala Gly Ile Ser Thr Ile Ile Leu Tyr His Met Ile
145                 150                 155                 160

Thr Trp Gly Leu Thr Leu Leu Leu Cys Val Glu Gly Val Ala Met Leu
                165                 170                 175

Tyr Tyr Pro Ser Ile Ser Ser Cys Glu Asn Gly Leu Gln His Ala Ile
            180                 185                 190

Pro His Tyr Val Thr Thr Tyr Ala Pro Met Leu Leu Val Leu Ala Val
        195                 200                 205

Asn Pro Val Leu Phe Thr Arg Thr Val Ser Ala Val Thr Ser Leu Leu
    210                 215                 220

Lys Gly Gln Gln Gly Ile Tyr Thr Glu Asn Glu Arg Arg Leu Gly Ser
225                 230                 235                 240

Glu Ile Lys Ile Arg Phe Phe Lys Ile Met Leu Val Phe Phe Ile Cys
                245                 250                 255

Trp Leu Pro Asn Ile Ile Asn Glu Ser Leu Leu Phe Tyr Leu Glu Met
            260                 265                 270
```

```
Gln Asp Asp Val Lys Ser Ser Asp Leu Lys Asn Ile Arg Asn Ala Ala
            275                 280                 285

Leu Ile Thr Trp Phe Ile Met Gly Ile Leu Asn Pro Met Gln Gly Phe
        290                 295                 300

Leu Asn Thr Leu Ala Phe His Gly Trp Thr Gly Leu Asp Leu Asp Phe
305                 310                 315                 320

Ser Arg Gln Arg Arg Glu Leu Pro Trp Asp Ser Ala Ser Thr Ser
                325                 330                 335

Leu Ala Gly Gly Phe Thr Pro Val Val Gly Ser Ser Leu Ile Tyr Gln
            340                 345                 350

Ser His Val Gln Glu Ile Lys Lys Asn Leu Ser Ala Asn Gly Gly Gln
        355                 360                 365

Gln Pro Ser Asp Ala Ile Ser Val Leu Ser Glu Asp Ser Glu Ser Ser
    370                 375                 380

Thr Val Glu Ile His Ile Ser Ser Glu Gln Arg Glu Phe Glu Glu Leu
385                 390                 395                 400

Lys Arg Asn Gly Ala Ser Trp Glu Ile Ser Thr Gly
                405                 410

<210> SEQ ID NO 19
<211> LENGTH: 1476
<212> TYPE: DNA
<213> ORGANISM: Pan troglodytes

<400> SEQUENCE: 19
atgacccagg caggccggcg gggtcctggc acacccgagc cgcgtctgtg aacacagccc      60
atggcctccc cgcgcctagg gaccttctgc tgccccacgc gggacgcggc cacgcagctc     120
gtgctgagct tccagccgcg ggccttccac gcgctctgcc tgggcagcgg tgggctccgc     180
ttggcgctgg gccttctgca gctgctgccc ggctgccggc ccgcgggccc cgggtcctcc     240
gcgacgtccc cgccggcctc ggtccacatc ctgcgcgctg ccgctgcctg cgaccttctc     300
ggctgcctgg gtatggtgat ccggtccacc gtgtggttag gattcccaaa ttttgttgac     360
agcgtctcgg atatgaacca cacggaaatt tggcctgctg ctttctgcgt ggggagtgcg     420
atgtggatcc agctgttgta cagtgcctgc ttctggtggc tgttttgcta tgcagtggat     480
gcttatctgg tgatccggag atcggcagga ctgagaacag tcctgaaaca tcacatcatc     540
aactttggtc tctctgtctt gctctgtcgc ccaggctgga atgactttg gttttcctct     600 ctcaggtgtg agcggggcct ggaccacgcc atccccccact atgtcaccat gtacctgccc     660
ctgctgctgt ttctcgtggc gaaccccatc ctgttccaaa agacagtgac tgcagtggcc     720
tctttactta aggaagaca aggcatttac acggagaacg agaggaggat gggagccgtg     780
atcaagatcc gattttttcaa aatcatgctg gttttaatta tttgttggtt gtcgaatatc     840
atcaatgaaa gccttttatt ctatcttgag atgcaaacag atatcaatgg aggttctttg     900
aaacctgtca gaactgcagc caagaccaca tggtttatta tggacacaga cagacacagt     960
cagtcttttg tctttttcctc tccaggttct gatgccagca caattgaaat tcacactgca    1020
agtgaatcct gcaacaaaaa tgagggtgac cctgctctcc caacccatgg agacctatga    1080
aggggatgtg ctgggggtcc agaccccata ttcctcagac tcaacaattc ttgttcttta    1140
gaactgtgtt ctcaccttcc caacactgca ctgccaaagt gtagcggccc ccaaaccttg    1200
ctctcatcac cagttagagc ttcttcccga gagcctttta ggataggaga aacgattcat    1260
gcacacgcgt gtgagaatgg aagagccccc tccagaccac tctacagctt ctctagcctt    1320
```

| | |
|---|---|
| agttgccact aggaagtttt ctgaggctgg ctgtaaagta agtgtaaggt ccacatcctt | 1380 |
| ggggaagtag ttaaataaaa tagttatgac tgagctctca gcctgacttg gattctgtct | 1440 |
| taacacttct agcaaaagaa aatatatgta cagtta | 1476 |

<210> SEQ ID NO 20

<400> SEQUENCE: 20

000

<210> SEQ ID NO 21
<211> LENGTH: 1770
<212> TYPE: DNA
<213> ORGANISM: Macaca mulatta

<400> SEQUENCE: 21

| | |
|---|---|
| caccgagcct ggctctactg caggcgctgg gggttggggt gggggagagg cccagggcgc | 60 |
| atgatgccgc cccagcccg cccagcacat gacccaggca ggccggcggg gtcctggcac | 120 |
| acccgagccg cgtccgtgag cacagcccat ggcctccccg cgcttaggga ccttctgctg | 180 |
| ccccacacgg gatgcggcca cgcaactcgt gctgagcttc cagccgcggg ccttccacgc | 240 |
| gctctgcctg gcagcggcg cgctccgctt ggcgctgggc cttctgcagc tgctgcccgg | 300 |
| ccgccggccc gcgggccccg ggtccccgc gacgtcccca ccggcctcgg tccgcatcct | 360 |
| gcgcgctgcc actgcctgcg accttctagg ctgcctgggt gttgtgatcc ggtccaccgt | 420 |
| gtggttagga ttcccaaatt ttgttgacag catctcagat gtgaaccgca cggaaatttg | 480 |
| gcctgctgtt ttctgcgtgg ggagtgcgat gtggatccag ctgttgtaca gtgcctgctt | 540 |
| ctggtggctg ttttgctatg cggtggatgc ttatctggtg atccggagat cggcgggact | 600 |
| gagcaccatc ctgctgtatc acatcatggc gtggggcctg gctaccctgc tctgtgtgga | 660 |
| gggagccgcc atgctctact acccttccgt atccaggtgt gagcgggtc tggaccatgc | 720 |
| catccccac tatgtcacca gtacctgcc cctgctgctg gttctcatgg ccaacccat | 780 |
| cctgttccaa aagacagtga ctgcagtggc ctctttactt aaaggaagac aaggcattta | 840 |
| cacggagaac gagagaagga tgggagctgt gatcaagatc cgattttca agataatgct | 900 |
| ggttttaatt atttgttggt tgtcgaatat catcaatgaa agccttttat tctatcttga | 960 |
| gatgcaaaca gatatcaatg gaggttcttt gaaacctgtc agaactgcag ccaagaccac | 1020 |
| atggtttatt atgggaatcc tgaatccagc ccagggattt ctcttgtctt tggccttcta | 1080 |
| tggctggaca ggatgtagcc tgggttttca gtctcccagg aaggagatcc agtgggaatc | 1140 |
| actgaccacc tcggctgctg atggggctca cccatccccg ctggactccc gggtgcccca | 1200 |
| ggaaaaccct gcttccaaga aggtgtctcg agtgggtggg cagacttctg atgaagccct | 1260 |
| gagcatgctg tctgaaggtt ctgatgccag tacaattgaa attcacactg caagtgaatc | 1320 |
| ctgcaacaaa aatgaggctg accctgctct cccaacccat ggagacctat gaagggatg | 1380 |
| tgctggggt ccagatccca tattcctcag actctgtaat tcttgttctt tagaactgtg | 1440 |
| ttctcacctt cccatcactg cactgccaaa gtgtagcagc ccccaaacct tgctctcatc | 1500 |
| accagttaga gcttcttccc gaagagcctt taggatagga gaaatgattc atgcatatgc | 1560 |
| gtgtgggaat ggaagagccc cctccagacc actctacagc ttctctaccc tcttagtttc | 1620 |
| cactaggaag ttttctgagg ctggctgtaa agtaagtgta aggtccaagt ccttgggaaa | 1680 |
| gtagttaaat aaaatagtta tgactaggct cccagcctga cttggattct gtcttaacac | 1740 |

-continued ttctagcaaa agaaaatgta tgtacagtta                                      1770

<210> SEQ ID NO 22
<211> LENGTH: 407
<212> TYPE: PRT
<213> ORGANISM: Macaca mulatta

<400> SEQUENCE: 22

Met Ala Ser Pro Arg Leu Gly Thr Phe Cys Cys Pro Thr Arg Asp Ala
1               5                   10                  15

Ala Thr Gln Leu Val Leu Ser Phe Gln Pro Arg Ala Phe His Ala Leu
            20                  25                  30

Cys Leu Gly Ser Gly Ala Leu Arg Leu Ala Leu Gly Leu Leu Gln Leu
        35                  40                  45

Leu Pro Gly Arg Arg Pro Ala Gly Pro Gly Ser Pro Ala Thr Ser Pro
    50                  55                  60

Pro Ala Ser Val Arg Ile Leu Arg Ala Ala Thr Ala Cys Asp Leu Leu
65                  70                  75                  80

Gly Cys Leu Gly Val Val Ile Arg Ser Thr Val Trp Leu Gly Phe Pro
                85                  90                  95

Asn Phe Val Asp Ser Ile Ser Asp Val Asn Arg Thr Glu Ile Trp Pro
            100                 105                 110

Ala Val Phe Cys Val Gly Ser Ala Met Trp Ile Gln Leu Leu Tyr Ser
        115                 120                 125

Ala Cys Phe Trp Trp Leu Phe Cys Tyr Ala Val Asp Ala Tyr Leu Val
    130                 135                 140

Ile Arg Arg Ser Ala Gly Leu Ser Thr Ile Leu Leu Tyr His Ile Met
145                 150                 155                 160

Ala Trp Gly Leu Ala Thr Leu Leu Cys Val Glu Gly Ala Ala Met Leu
                165                 170                 175

Tyr Tyr Pro Ser Val Ser Arg Cys Glu Arg Gly Leu Asp His Ala Ile
            180                 185                 190

Pro His Tyr Val Thr Met Tyr Leu Pro Leu Leu Val Leu Met Ala
        195                 200                 205

Asn Pro Ile Leu Phe Gln Lys Thr Val Thr Ala Val Ala Ser Leu Leu
    210                 215                 220

Lys Gly Arg Gln Gly Ile Tyr Thr Glu Asn Glu Arg Arg Met Gly Ala
225                 230                 235                 240

Val Ile Lys Ile Arg Phe Phe Lys Ile Met Leu Val Leu Ile Ile Cys
                245                 250                 255

Trp Leu Ser Asn Ile Ile Asn Glu Ser Leu Leu Phe Tyr Leu Glu Met
            260                 265                 270

Gln Thr Asp Ile Asn Gly Gly Ser Leu Lys Pro Val Arg Thr Ala Ala
        275                 280                 285

Lys Thr Thr Trp Phe Ile Met Gly Ile Leu Asn Pro Ala Gln Gly Phe
    290                 295                 300

Leu Leu Ser Leu Ala Phe Tyr Gly Trp Thr Gly Cys Ser Leu Gly Phe
305                 310                 315                 320

Gln Ser Pro Arg Lys Glu Ile Gln Trp Glu Ser Leu Thr Thr Ser Ala
                325                 330                 335

Ala Asp Gly Ala His Pro Ser Pro Leu Asp Ser Arg Val Pro Gln Glu
            340                 345                 350

Asn Pro Ala Ser Lys Lys Val Ser Arg Val Gly Gly Gln Thr Ser Asp
        355                 360                 365

```
Glu Ala Leu Ser Met Leu Ser Glu Gly Ser Asp Ala Ser Thr Ile Glu
370                 375                 380
Ile His Thr Ala Ser Glu Ser Cys Asn Lys Asn Glu Ala Asp Pro Ala
385                 390                 395                 400
Leu Pro Thr His Gly Asp Leu
                405

<210> SEQ ID NO 23
<211> LENGTH: 517
<212> TYPE: DNA
<213> ORGANISM: Rhesus macaque

<400> SEQUENCE: 23
gaagctgatg acaaacctgt taggatgcag acactgtcac agtcaaattt tgtcttttcc      60
tctccaggtt ctgatgccag tacaattgaa attcacactg caagtgaatc ctgcaacaaa     120
aatgaggctg accctgctct cccaacccat ggagacctat gaaggggatg tgctgggggt     180
ccagatccca tattcctcag actctgtaat tcttgttctt tataactgtg ttctcacctt     240
cccatcactg cactgccaaa gtgtagcagc ccccaaacct tgctctcatc accagttaga     300
gcttcttccc gaagagcctt taggataggt gaaatgattc atgcatatgc gtgtgggaat     360
ggaagagccc cctccagacc actctacagc ttctctaccc tcttagtttc cactaggaag     420
ttttctgagg ctggctgtaa agtaagtgta aggtccaagt ccttgggaaa gtagttaaat     480
aaaatagtta tgactaggct cccagcctga cttggat                              517

<210> SEQ ID NO 24

<400> SEQUENCE: 24

000

<210> SEQ ID NO 25
<211> LENGTH: 1542
<212> TYPE: DNA
<213> ORGANISM: Homo sapiens

<400> SEQUENCE: 25
ggtcgcttta agaaaggagt agctgtaatc tgaagcctgc tggacgctgg attagaaggc      60
agcaaaaaaa gctctgtgct ggctggagcc ccctcagtgt gcaggcttag agggactagg     120
ctgggtgtgg agctgcagcg tatccacagg ccccaggatg caggccctgg tgctactcct     180
ctgcattgga gccctcctcg gcacagcag ctgccagaac cctgccagcc cccggagga     240
gggctcccca gaccccgaca gcacaggggc gctggtggag gaggaggatc ctttcttcaa     300
agtccccgtg aacaagctgg cagcggctgt ctccaacttc ggctatgacc tgtaccgggt     360
gcgatccagc acgagcccca cgaccaacgt gctcctgtct cctctcagtg tggccacggc     420
cctctcggcc ctctcgctgg gagcggagca gcgaacagaa tccatcattc accgggctct     480
ctactatgac ttgatcagca gcccagacat ccatggtacc tataaggagc tccttgacac     540
ggtcactgcc ccccagaaga acctcaagag tgcctcccgg atcgtctttg agaagaagct     600
gcgcataaaa tccagctttg tggcacctct ggaaaagtca tatgggacca ggcccagagt     660
cctgacgggc aaccctcgct tggacctgca agatcaac aactgggtgc aggcgcagat     720
gaaagggaag ctcgccaggt ccacaaagga aattcccgat gagatcagca ttctccttct     780
cggtgtggcg cacttcaagg ggcagtgggt aacaaagttt gactccagaa agacttccct     840
cgaggatttc tacttggatg aagagaggac cgtgagggtc cccatgatgt cggaccctaa     900
```

-continued

```
ggctgtttta cgctatggct tggattcaga tctcagctgc aagattgccc agctgccctt      960
gaccggaagc atgagtatca tcttcttcct gcccctgaaa gtgacccaga atttgacctt     1020
gatagaggag agcctcacct ccgagttcat tcatgacata gaccgagaac tgaagaccgt     1080
gcaggcggtc ctcactgtcc ccaagctgaa gctgagttat gaaggcgaag tcaccaagtc     1140
cctgcaggag atgaagctgc aatccttgtt tgattcacca gactttagca agatcacagg     1200
caaacccatc aagctgactc aggtggaaca ccgggctggc tttgagtgga cgaggatgg     1260 ggcgggaacc accccagcc cagggctgca gcctgcccac ctcaccttcc cgctggacta     1320
tcaccttaac cagcctttca tcttcgtact gagggacaca gacacagggg cccttctctt     1380
cattggcaag attctggacc ccaggggccc ctaatatccc agtttaatat tccaataccc     1440
tagaagaaaa cccgagggac agcagattcc acaggacacg aaggctgccc ctgtaaggtt     1500
tcaatgcata caataaaaga gctttatccc taacttctgt ta                        1542
```

<210> SEQ ID NO 26
<211> LENGTH: 418
<212> TYPE: PRT
<213> ORGANISM: Homo sapiens

<400> SEQUENCE: 26

```
Met Gln Ala Leu Val Leu Leu Cys Ile Gly Ala Leu Leu Gly His
1               5                   10                  15

Ser Ser Cys Gln Asn Pro Ala Ser Pro Glu Glu Gly Ser Pro Asp
            20                  25                  30

Pro Asp Ser Thr Gly Ala Leu Val Glu Glu Glu Asp Pro Phe Phe Lys
            35                  40                  45

Val Pro Val Asn Lys Leu Ala Ala Ala Val Ser Asn Phe Gly Tyr Asp
50                  55                  60

Leu Tyr Arg Val Arg Ser Ser Thr Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
            100                 105                 110

Ile Ser Ser Pro Asp Ile His Gly Thr Tyr Lys Glu Leu Leu Asp Thr
            115                 120                 125

Val Thr Ala Pro Gln Lys Asn Leu Lys Ser Ala Ser Arg Ile Val Phe
            130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Ile Pro Asp Glu Ile Ser Ile Leu Leu Leu
            195                 200                 205

Gly Val Ala His Phe Lys Gly Gln Trp Val Thr Lys Phe Asp Ser Arg
            210                 215                 220

Lys Thr Ser Leu Glu Asp Phe Tyr Leu Asp Glu Arg Thr Val Arg
225                 230                 235                 240

Val Pro Met Met Ser Asp Pro Lys Ala Val Leu Arg Tyr Gly Leu Asp
                245                 250                 255
```

```
Ser Asp Leu Ser Cys Lys Ile Ala Gln Leu Pro Leu Thr Gly Ser Met
            260                 265                 270
Ser Ile Ile Phe Phe Leu Pro Leu Lys Val Thr Gln Asn Leu Thr Leu
        275                 280                 285
Ile Glu Glu Ser Leu Thr Ser Glu Phe Ile His Asp Ile Asp Arg Glu
    290                 295                 300
Leu Lys Thr Val Gln Ala Val Leu Thr Val Pro Lys Leu Lys Leu Ser
305                 310                 315                 320
Tyr Glu Gly Glu Val Thr Lys Ser Leu Gln Glu Met Lys Leu Gln Ser
                325                 330                 335
Leu Phe Asp Ser Pro Asp Phe Ser Lys Ile Thr Gly Lys Pro Ile Lys
            340                 345                 350
Leu Thr Gln Val Glu His Arg Ala Gly Phe Glu Trp Asn Glu Asp Gly
        355                 360                 365
Ala Gly Thr Thr Pro Ser Pro Gly Leu Gln Pro Ala His Leu Thr Phe
    370                 375                 380
Pro Leu Asp Tyr His Leu Asn Gln Pro Phe Ile Phe Val Leu Arg Asp
385                 390                 395                 400
Thr Asp Thr Gly Ala Leu Leu Phe Ile Gly Lys Ile Leu Asp Pro Arg
                405                 410                 415
Gly Pro

<210> SEQ ID NO 27
<211> LENGTH: 2105
<212> TYPE: DNA
<213> ORGANISM: Rattus norvegicus

<400> SEQUENCE: 27
gtggtgtttg accccttcgg cggtgtgtga aagaaaagg aaggagccgg agcttcctag    60
gagcggtcgc cgaaatgttc cggtgtggag cctggcggg tgctttcaag cagaaactgg   120
tgcccttggt gcgtcggtg tgcgtccaga ggccgaaaca gaggaaccgg cttccaggca   180
acttgttcca gcaatggcgt gttcctctag aactccagat ggcaagacaa atggctagct   240
ctggtccatc agggggcaaa atggataatt ctgtgttagt ccttattgtg ggcttatcaa   300
caataggagc tggtgcatat gcctacaaga ctattaaaga agaccaaaaa agatataatg   360
aaagaatat gggattagga ctgtcaccag aagagaaaca gagaagagcc attgcctctg   420
ctgcagaagg aggctcagtt cctccaatca gggtaccaag tcacgtccct ttcctgctga   480
ttggtggagg tactgctgcc tttgcagcag ctagatccat ccgggctcgg gatcctgggg   540
ccagggtcct catcgtatct gaagaccctg aactaccata catgcgacct cctctctcaa   600
aagaattgtg gttttcagat gacccaaatg tcacaaagac actgcagttc agacagtgga   660
atggaaaaga gagaagcatc tatttccagc accttctttt ctatgtctct gctcaggacc   720
tgcctcatat tgagaatggt ggtgtggctg tcctcaccgg gaagaaggta gtccacctgg   780
atgtaagagg caacatggtg aaacttaatg atggctctca gattaccttt gaaaagtgct   840
tgattgcaac gggaggcact ccaagaagtc tgtctgctat cgatagggct ggagcagagg   900
tgaagagtag aacaacactt ttcagaaaga ttggagattt tagagccttg gagaagatct   960
cccgggaagt caagtcaatt acagttattg gtggaggctt ccttgggagc gaactggcct  1020
gtgctcttgg cagaaagtct caagcctcag gcatagaagt gattcagctc ttccctgaga  1080
aaggaaatat ggggaagatc cttcctgaat acctcagcaa ctggaccatg gaaaagtca   1140
aacgagaggg agtgaaagtg atgcccaatg caattgtaca atcagttgga gtcagcggtg  1200
```

```
gcaagttact cattaagcta aaggacggaa ggaaggtaga aactgaccac atagtaacag    1260
ctgtgggcct agaacccaat gtcgagttgg ccaagactgg tgggctggaa atagattccg    1320
attttggtgg cttccgggta aatgcagagc ttcaagcacg ttctaacatc tgggtggcag    1380
gagatgctgc atgcttctat gatataaagt tgggtcgaag gagagtagaa catcatgatc    1440
acgctgttgt gagtggaaga ctggctggag aaaatatgac tggagctgct aagccatact    1500
ggcatcagtc aatgttctgg agtgatttgg gtcctgatgt tggctatgaa gctattggtc    1560
tggtggatag tagtttgccc acagttggtg ttttttgcaaa agcaactgca caagacaacc    1620
caaaatctgc cacagagcag tcaggaactg gtatccgttc ggagagtgag acagagtctg    1680
aagcttctga aatcacaatc cctcccagtg accctgcagt cccacaggtc cctgttgaag    1740
gggaggacta cggcaaaggt gtcatcttct acctcaggga caagttgtg gtggggattg    1800 tgctatggaa cgtctttaac cgaatgccga ttgcaaggaa gatcattaaa gacggtgagc    1860
aacatgaaga cctcaatgaa gtagccaaac tcttcaacat tcatgaagat tgaatcccta    1920
tcatggaata cacaagcact tttccatccc tgacagggaa tgggtggata aaagaacatt    1980
ttttattcag catactttt ctttatgtag gagcaggaat cgaacaagcc tctgtgaata    2040
ttttcatctg tataaatgca catcacaaat taaaatctga ttcttttcaa aaaaaaagcg    2100
gccgc                                                              2105

<210> SEQ ID NO 28
<211> LENGTH: 612
<212> TYPE: PRT
<213> ORGANISM: Rattus norvegicus

<400> SEQUENCE: 28

Met Phe Arg Cys Gly Gly Leu Ala Gly Ala Phe Lys Gln Lys Leu Val
1               5                   10                  15

Pro Leu Val Arg Ser Val Cys Val Gln Arg Pro Lys Gln Arg Asn Arg
            20                  25                  30

Leu Pro Gly Asn Leu Phe Gln Gln Trp Arg Val Pro Leu Glu Leu Gln
        35                  40                  45

Met Ala Arg Gln Met Ala Ser Ser Gly Pro Ser Gly Gly Lys Met Asp
    50                  55                  60

Asn Ser Val Leu Val Leu Ile Val Gly Leu Ser Thr Ile Gly Ala Gly
65                  70                  75                  80

Ala Tyr Ala Tyr Lys Thr Ile Lys Glu Asp Gln Lys Arg Tyr Asn Glu
                85                  90                  95

Arg Ile Met Gly Leu Gly Leu Ser Pro Glu Glu Lys Gln Arg Arg Ala
            100                 105                 110

Ile Ala Ser Ala Ala Glu Gly Gly Ser Val Pro Pro Ile Arg Val Pro
        115                 120                 125

Ser His Val Pro Phe Leu Leu Ile Gly Gly Thr Ala Ala Phe Ala
    130                 135                 140

Ala Ala Arg Ser Ile Arg Ala Arg Asp Pro Gly Ala Arg Val Leu Ile
145                 150                 155                 160

Val Ser Glu Asp Pro Glu Leu Pro Tyr Met Arg Pro Pro Leu Ser Lys
                165                 170                 175

Glu Leu Trp Phe Ser Asp Asp Pro Asn Val Thr Lys Thr Leu Gln Phe
            180                 185                 190

Arg Gln Trp Asn Gly Lys Glu Arg Ser Ile Tyr Phe Gln Pro Pro Ser
        195                 200                 205
```

```
Phe Tyr Val Ser Ala Gln Asp Leu Pro His Ile Glu Asn Gly Gly Val
    210                 215                 220

Ala Val Leu Thr Gly Lys Lys Val Val His Leu Asp Val Arg Gly Asn
225                 230                 235                 240

Met Val Lys Leu Asn Asp Gly Ser Gln Ile Thr Phe Glu Lys Cys Leu
                245                 250                 255

Ile Ala Thr Gly Gly Thr Pro Arg Ser Leu Ser Ala Ile Asp Arg Ala
                260                 265                 270

Gly Ala Glu Val Lys Ser Arg Thr Thr Leu Phe Arg Lys Ile Gly Asp
            275                 280                 285

Phe Arg Ala Leu Glu Lys Ile Ser Arg Glu Val Lys Ser Ile Thr Val
    290                 295                 300

Ile Gly Gly Gly Phe Leu Gly Ser Glu Leu Ala Cys Ala Leu Gly Arg
305                 310                 315                 320

Lys Ser Gln Ala Ser Gly Ile Glu Val Ile Gln Leu Phe Pro Glu Lys
                325                 330                 335

Gly Asn Met Gly Lys Ile Leu Pro Glu Tyr Leu Ser Asn Trp Thr Met
                340                 345                 350

Glu Lys Val Lys Arg Glu Gly Val Lys Val Met Pro Asn Ala Ile Val
            355                 360                 365

Gln Ser Val Gly Val Ser Gly Gly Lys Leu Leu Ile Lys Leu Lys Asp
    370                 375                 380

Gly Arg Lys Val Glu Thr Asp His Ile Val Thr Ala Val Gly Leu Glu
385                 390                 395                 400

Pro Asn Val Glu Leu Ala Lys Thr Gly Gly Leu Glu Ile Asp Ser Asp
                405                 410                 415

Phe Gly Gly Phe Arg Val Asn Ala Glu Leu Gln Ala Arg Ser Asn Ile
                420                 425                 430

Trp Val Ala Gly Asp Ala Ala Cys Phe Tyr Asp Ile Lys Leu Gly Arg
            435                 440                 445

Arg Arg Val Glu His His Asp His Ala Val Val Ser Gly Arg Leu Ala
    450                 455                 460

Gly Glu Asn Met Thr Gly Ala Ala Lys Pro Tyr Trp His Gln Ser Met
465                 470                 475                 480

Phe Trp Ser Asp Leu Gly Pro Asp Val Gly Tyr Glu Ala Ile Gly Leu
                485                 490                 495

Val Asp Ser Ser Leu Pro Thr Val Gly Val Phe Ala Lys Ala Thr Ala
                500                 505                 510

Gln Asp Asn Pro Lys Ser Ala Thr Glu Gln Ser Gly Thr Gly Ile Arg
            515                 520                 525

Ser Glu Ser Glu Thr Glu Ser Glu Ala Ser Glu Ile Thr Ile Pro Pro
    530                 535                 540

Ser Asp Pro Ala Val Pro Gln Val Pro Val Glu Gly Glu Asp Tyr Gly
545                 550                 555                 560

Lys Gly Val Ile Phe Tyr Leu Arg Asp Lys Val Val Val Gly Ile Val
                565                 570                 575

Leu Trp Asn Val Phe Asn Arg Met Pro Ile Ala Arg Lys Ile Ile Lys
                580                 585                 590

Asp Gly Glu Gln His Glu Asp Leu Asn Glu Val Ala Lys Leu Phe Asn
            595                 600                 605

Ile His Glu Asp
            610
```

<210> SEQ ID NO 29
<211> LENGTH: 1486
<212> TYPE: DNA
<213> ORGANISM: Taeniopygia guttata

<400> SEQUENCE: 29

```
gtggctgcac caaacccgca ctgtcctcga ctcgcaccgc tgggagccct gacagcagcg      60
gccgagagga gccccaggtc caggcatgca ggttccagtg gttctccttt tcctgggtct     120
cttaactgtc ccaagcagaa cccagaactc agctaccgag cagaactctg ccacagctga     180
tggagccaat gctgggtgag gaagaggaag atccattcta caagagcccc gtgaacaagc     240
tggcagctgc agtctccaac tttggctacg acctgtaccg ccagcagtcc atccggacag     300
ccacggccaa cgtgctgctg tctcccttca gcctggccac tgcactttct ggtctctcac     360
ttggggctgg agaacgaact gaggatgtga tttctcgcgc cctcttctac gatctgctga     420
acaaggccga ggtccacgac acctacaaag agctcctgag cagtgtgact gggccagaga     480
agagcatgaa aagtgcctcc cggatcatct ggagaaaag actcagggca aggcctggat     540
ttcacagcca gctcgagaag tcctacaaga tgcgaccaag agcactgagt ggcaacaccc     600
agctggacct ccaagaaatc aacacctggg tccgacagca gacaagggaa aggatcatga     660
ggttcatgaa ggacatgccc acagatgtca gcattctcct tgctggggct gctttcttca     720
aggggacatg gaaaaccaag tttgacacca agaggactgc cctgcaggac ttccacctgg     780
atgaggacag gactgtgaag gtgtccatga tgtcagaccc caaagccatc ctgagatatg     840
gttttgactc agaactcaac tgcaagattg cccagctgcc cctgacagag gaatcagtg      900
ccatgttctt cctgcccacg aaggtgaccc agaacatgac tctgattgag aaagcctca     960
cttctgagtt tgtccacgat gtggacaagg agctgaagac agtccacgct gtgctgagct    1020
tgcccaaact gaagctgaac cacgaagagg cacttggcag cacactaaag gagacaaggc    1080
tccaatcact tttcacatca cctgatttct ccaagatttc tgccaaacct ctgagattat    1140
ctcatgtgca acacaaggca atgctggagc ttggtgagga tggggaaaga tccacaccaa    1200
acgctggggc caatgctgct cgtctgacct tccccataga ataccacgtg acagacctt     1260
tccttcttgt actgagggat gataccactg gaccctcct cttcattggc aagatcctgg    1320
atcccagggg tgtttagatc ccttcacaat aatctgtaat ggtagggccc aaatggaaag    1380
ggtgatattg ggagggatac tggctccctg ctctgctgca caaagacaca acttgcaaat    1440
cttacgcctt catgctgcaa taaaagagct tttgctatta atctca                   1486
```

<210> SEQ ID NO 30
<211> LENGTH: 385
<212> TYPE: PRT
<213> ORGANISM: Taeniopygia guttata

<400> SEQUENCE: 30

Met Glu Pro Met Leu Gly Glu Glu Glu Asp Pro Phe Tyr Lys Ser
1               5                   10                  15

Pro Val Asn Lys Leu Ala Ala Ala Val Ser Asn Phe Gly Tyr Asp Leu
            20                  25                  30

Tyr Arg Gln Gln Ser Ile Arg Thr Ala Thr Ala Asn Val Leu Leu Ser
        35                  40                  45

Pro Phe Ser Leu Ala Thr Ala Leu Ser Gly Leu Ser Leu Gly Ala Gly
    50                  55                  60

Glu Arg Thr Glu Asp Val Ile Ser Arg Ala Leu Phe Tyr Asp Leu Leu

```
                65                  70                  75                  80
            Asn Lys Ala Glu Val His Asp Thr Tyr Lys Glu Leu Leu Ser Ser Val
                            85                  90                  95

Thr Gly Pro Glu Lys Ser Met Lys Ser Ala Ser Arg Ile Ile Leu Glu
                       100                 105                 110

Lys Arg Leu Arg Ala Arg Pro Gly Phe His Ser Gln Leu Glu Lys Ser
                       115                 120                 125

Tyr Lys Met Arg Pro Arg Ala Leu Ser Gly Asn Thr Gln Leu Asp Leu
                       130                 135                 140

Gln Glu Ile Asn Thr Trp Val Arg Gln Thr Lys Gly Arg Ile Met
            145                 150                 155                 160

Arg Phe Met Lys Asp Met Pro Thr Asp Val Ser Ile Leu Leu Ala Gly
                            165                 170                 175

Ala Ala Phe Phe Lys Gly Thr Trp Lys Thr Lys Phe Asp Thr Lys Arg
                       180                 185                 190

Thr Ala Leu Gln Asp Phe His Leu Asp Glu Asp Arg Thr Val Lys Val
                       195                 200                 205

Ser Met Met Ser Asp Pro Lys Ala Ile Leu Arg Tyr Gly Phe Asp Ser
                       210                 215                 220

Glu Leu Asn Cys Lys Ile Ala Gln Leu Pro Leu Thr Glu Gly Ile Ser
            225                 230                 235                 240

Ala Met Phe Phe Leu Pro Thr Lys Val Thr Gln Asn Met Thr Leu Ile
                            245                 250                 255

Glu Glu Ser Leu Thr Ser Glu Phe Val His Asp Val Asp Lys Glu Leu
                       260                 265                 270

Lys Thr Val His Ala Val Leu Ser Leu Pro Lys Leu Lys Leu Asn His
                       275                 280                 285

Glu Glu Ala Leu Gly Ser Thr Leu Lys Glu Thr Arg Leu Gln Ser Leu
                       290                 295                 300

Phe Thr Ser Pro Asp Phe Ser Lys Ile Ser Ala Lys Pro Leu Arg Leu
            305                 310                 315                 320

Ser His Val Gln His Lys Ala Met Leu Glu Leu Gly Glu Asp Gly Glu
                            325                 330                 335

Arg Ser Thr Pro Asn Ala Gly Ala Asn Ala Ala Arg Leu Thr Phe Pro
                       340                 345                 350

Ile Glu Tyr His Val Asp Arg Pro Phe Leu Leu Val Leu Arg Asp Asp
                       355                 360                 365

Thr Thr Gly Thr Leu Leu Phe Ile Gly Lys Ile Leu Asp Pro Arg Gly
                       370                 375                 380

Val
            385

<210> SEQ ID NO 31
<211> LENGTH: 1464
<212> TYPE: DNA
<213> ORGANISM: Equus caballus

<400> SEQUENCE: 31
ttaaaagttt tgtgcttgct ggagccccct cagtgtgcag acctaggctg ggcgcggagc     60
tgcagcacac ccacaggccc cgggatgcag gccctaatgc tactcctctg gactggagcc    120
ctccttgggc atggcagctg ccagaacaac gccggcggcc cagaggaggg ctccccagac    180
cctgacatca caggggcacc agtggaggag gaggatcctt tcctcaaggt ccctgtgaac    240
aagctggcag cggccgtctc caactttggc tatgaccctg taccgcgcga aatccagcatg    300
```

```
agccccaccg ccaatgtgct cctgtcccca ctcagcgtgg ccacagcact ctctgccctt    360
tcgctggggg cggaacagcg gacagagtcc agcattcacc tggctctcta ctatgacctg    420
atcaagaacc cagacatcca cggcacctac aaggaactcc ttgcgtccgt cactgccccc    480
aataagaact tcaagagcgc ttcccgaatc atcttcgaga agaagctgcg catcaaatcc    540
agctttgtta caccactgga gaagtcatat gggaccaggc caagatcctg actggcaac    600 tctcgcacgg atcttcagga gattaacaac tgggtgcagg cccagatgaa agggaaaatt    660
gctaggtcca aagggaagt gcccagtgaa atcagcattc ccttctcgg tgtggcttac     720 ttcaagggc agtgggtaac aaagtttgac tccagaaaga cttccctcca ggatttccac    780
ttggatgagg agaggaccgt gacagtcccc acgatgtcag atccgaaggc cattctacgc    840
tacggcttgg attctgatct caactgtaag atcgcccagc taccctgac cggaagcatg    900 agcatcgtct tcttcctgcc tcagaaagtg acccagaacc tgaccatgat agaagagagc    960
ctcacctccg agttccttca tgacatagac cgagagctga agactgtgca ggcagtcctg   1020
accatcccca gctgaagct gagttatgag ggtgaagtca ctaagtccct gcaggagata    1080
aagctgcaat ccttgtttga ttcaccagac tttagcaaga tcacaggcaa acctctcaag   1140
cttactcaag tggaacatcg tgctggcttt gagtggaatg aggatggggc aaccaacccc   1200
agccaagggc cccagcctgc ccacctcacc ttcccttgg actaccacct taaccaacct    1260
ttcatctttg tactgaggga cacggacaca ggggcccttc tcttcatagg caaaattctg   1320
gaccccaggg gcacttaatg ctctagctta atgttcaaat accctagatg aagaaaaccc   1380
tagagggatg gcagattata tattacgtga aggctgccct ataatgtttc aatgtatcct   1440
tttcaataaa agtgctttat cctt                                           1464
```

<210> SEQ ID NO 32
<211> LENGTH: 417
<212> TYPE: PRT
<213> ORGANISM: Equus caballus

<400> SEQUENCE: 32

```
Met Gln Ala Leu Met Leu Leu Leu Trp Thr Gly Ala Leu Leu Gly His
1               5                   10                  15

Gly Ser Cys Gln Asn Asn Ala Gly Gly Pro Glu Glu Gly Ser Pro Asp
            20                  25                  30

Pro Asp Ile Thr Gly Ala Pro Val Glu Glu Asp Pro Phe Leu Lys
        35                  40                  45

Val Pro Val Asn Lys Leu Ala Ala Val Ser Asn Phe Gly Tyr Asp
    50                  55                  60

Leu Tyr Arg Ala Lys Ser Ser Met Ser Pro Thr Ala Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ser Ile His Leu Ala Leu Tyr Tyr Asp Leu
            100                 105                 110

Ile Lys Asn Pro Asp Ile His Gly Thr Tyr Lys Glu Leu Leu Ala Ser
        115                 120                 125

Val Thr Ala Pro Asn Lys Asn Phe Lys Ser Ala Ser Arg Ile Ile Phe
    130                 135                 140

Glu Lys Lys Leu Arg Ile Lys Ser Ser Phe Val Thr Pro Leu Glu Lys
145                 150                 155                 160
```

```
Ser Tyr Gly Thr Arg Pro Lys Ile Leu Thr Gly Asn Ser Arg Thr Asp
            165                 170                 175

Leu Gln Glu Ile Asn Asn Trp Val Gln Ala Gln Met Lys Gly Lys Ile
        180                 185                 190

Ala Arg Ser Thr Arg Glu Val Pro Ser Glu Ile Ser Ile Leu Leu Leu
        195                 200                 205

Gly Val Ala Tyr Phe Lys Gly Gln Trp Val Thr Lys Phe Asp Ser Arg
    210                 215                 220

Lys Thr Ser Leu Gln Asp Phe His Leu Asp Glu Arg Thr Val Thr
225                 230                 235                 240

Val Pro Thr Met Ser Asp Pro Lys Ala Ile Leu Arg Tyr Gly Leu Asp
                245                 250                 255

Ser Asp Leu Asn Cys Lys Ile Ala Gln Leu Pro Leu Thr Gly Ser Met
            260                 265                 270

Ser Ile Val Phe Phe Leu Pro Gln Lys Val Thr Gln Asn Leu Thr Met
        275                 280                 285

Ile Glu Glu Ser Leu Thr Ser Glu Phe Leu His Asp Ile Asp Arg Glu
    290                 295                 300

Leu Lys Thr Val Gln Ala Val Leu Thr Ile Pro Lys Leu Lys Leu Ser
305                 310                 315                 320

Tyr Glu Gly Glu Val Thr Lys Ser Leu Gln Glu Ile Lys Leu Gln Ser
                325                 330                 335

Leu Phe Asp Ser Pro Asp Phe Ser Lys Ile Thr Gly Lys Pro Leu Lys
            340                 345                 350

Leu Thr Gln Val Glu His Arg Ala Gly Phe Glu Trp Asn Glu Asp Gly
        355                 360                 365

Ala Thr Asn Pro Ser Gln Gly Pro Gln Pro Ala His Leu Thr Phe Pro
    370                 375                 380

Leu Asp Tyr His Leu Asn Gln Pro Phe Ile Phe Val Leu Arg Asp Thr
385                 390                 395                 400

Asp Thr Gly Ala Leu Leu Phe Ile Gly Lys Ile Leu Asp Pro Arg Gly
                405                 410                 415

Thr

<210> SEQ ID NO 33
<211> LENGTH: 1503
<212> TYPE: DNA
<213> ORGANISM: Xenopus (Silurana) tropicalis

<400> SEQUENCE: 33
gcccggggga ggtaccctgt cccaggagac agaacccgtg ggtaccagca attacccttg     60
ccaagaactg acaatgaaga tctacctggc tttgcttttt acaggaagtt tcctttccta    120
caccagcgcc cagaatgctg cagatgaggt ccctacagag gtagaagaag aagatccctt    180
ctacaagagt ccaatcaaca ggcttgcctc ttctgcatct aactttggat atgacctata    240
tcgtatgcaa gcaaacaaaa atcccaacag caatatcatt atttcaccac tgagcattgc    300
tacatctctg tcaagtcttt ccttgggggg tggacaaaga actgaatcat taatccagcg    360
ttctctatac tatgaccttc tcaatgatcc tgaagtccat gctacatata agacttgct    420 tgcaagtttt acttctcaag cgagtggatt gaaaagcaca tggcgaatca tgctggagag    480
aaggctcagg ctacggatgg attttgtgac tcaggtagag aagttctatg aaacaagcc    540 aaaggttttg acaggaagca ctcgcctgga cctgcaggaa gccaacgact ttatacagaa    600
gcagacacaa gggaaagtgg tgaagttctt caaagagatt ccaactagtg tgagcattct    660
```

```
gctgctcgga actacttact taaaaggcca gtgggcgtac aaatttaatc ctcgggaaac    720
tgtccagcgt gaattccacc tcgatgaaca gacatctgtc actgttccaa tgatgtcatc    780
taaaaacatc cccgtgagat acggcttaga ctctgatttt aactgcaaga ttgttcagct    840
tcctctcact ggtggggtta gcatcatgtt tttcctgcca aacacagtca cccagaactt    900
gactatgatt gaagagggcc tgacatctga gtttgtccat gacatagacc aggcactgca    960
gcctatcaac ttggtcctaa gcgtccctaa actaaagctg aactatgaag ctgagcttaa   1020
ggaagcactg caggaatcaa agctccaatc ccttttcgcc actcctgact tcagcaaaat   1080
ctcctcaaag ccattaaagc tctcctatgt cgtacataaa gccaccttgg aattgaacga   1140
ggaaggagca gagacagcgc caaaaccaga ggacagccac cgcaattact tcctttgga    1200
gtatcactta gatcatcctt tcttgtttgt tctccgtgcc aatgacaacg gcgctctcct   1260
cttcattggg aaagttatgg accctaaggg attctccttc taataaatca gtgctgtgct   1320
atctcccttt aatgttctga atgacggaga agtgcaataa attgctttgc aaaatatctc   1380
aagtcccttt ggcagagagc aactgtagct actgtactgt agccgactcc aatgccacag   1440
ttgcctgtgt tcaatcccac tgtgttatta aatcattttc cagaaaaaaa aaaaaaaaa    1500
aaa                                                                 1503
```

<210> SEQ ID NO 34
<211> LENGTH: 409
<212> TYPE: PRT
<213> ORGANISM: Xenopus (Silurana) tropicalis

<400> SEQUENCE: 34

```
Met Lys Ile Tyr Leu Ala Leu Leu Phe Thr Gly Ser Phe Leu Ser Tyr
1               5                   10                  15

Thr Ser Ala Gln Asn Ala Ala Asp Glu Val Pro Thr Glu Val Glu Glu
            20                  25                  30

Glu Asp Pro Phe Tyr Lys Ser Pro Ile Asn Arg Leu Ala Ser Ser Ala
        35                  40                  45

Ser Asn Phe Gly Tyr Asp Leu Tyr Arg Met Gln Ala Asn Lys Asn Pro
    50                  55                  60

Asn Ser Asn Ile Ile Ile Ser Pro Leu Ser Ile Ala Thr Ser Leu Ser
65                  70                  75                  80

Ser Leu Ser Leu Gly Gly Gly Gln Arg Thr Glu Ser Leu Ile Gln Arg
                85                  90                  95

Ser Leu Tyr Tyr Asp Leu Leu Asn Asp Pro Glu Val His Ala Thr Tyr
            100                 105                 110

Lys Asp Leu Leu Ala Ser Phe Thr Ser Gln Ala Ser Gly Leu Lys Ser
        115                 120                 125

Thr Trp Arg Ile Met Leu Glu Arg Arg Leu Arg Leu Arg Met Asp Phe
    130                 135                 140

Val Thr Gln Val Glu Lys Phe Tyr Gly Asn Lys Pro Lys Val Leu Thr
145                 150                 155                 160

Gly Ser Thr Arg Leu Asp Leu Gln Glu Ala Asn Asp Phe Ile Gln Lys
                165                 170                 175

Gln Thr Gln Gly Lys Val Val Lys Phe Lys Glu Ile Pro Thr Ser
            180                 185                 190

Val Ser Ile Leu Leu Leu Gly Thr Thr Tyr Leu Lys Gly Gln Trp Ala
        195                 200                 205

Tyr Lys Phe Asn Pro Arg Glu Thr Val Gln Arg Glu Phe His Leu Asp
```

```
             210                 215                 220
Glu Gln Thr Ser Val Thr Val Pro Met Met Ser Ser Lys Asn Ile Pro
225                 230                 235                 240

Val Arg Tyr Gly Leu Asp Ser Asp Phe Asn Cys Lys Ile Val Gln Leu
                245                 250                 255

Pro Leu Thr Gly Gly Val Ser Ile Met Phe Phe Leu Pro Asn Thr Val
                260                 265                 270

Thr Gln Asn Leu Thr Met Ile Glu Glu Gly Leu Thr Ser Glu Phe Val
            275                 280                 285

His Asp Ile Asp Gln Ala Leu Gln Pro Ile Asn Leu Val Leu Ser Val
        290                 295                 300

Pro Lys Leu Lys Leu Asn Tyr Glu Ala Glu Leu Lys Glu Ala Leu Gln
305                 310                 315                 320

Glu Ser Lys Leu Gln Ser Leu Phe Ala Thr Pro Asp Phe Ser Lys Ile
                325                 330                 335

Ser Ser Lys Pro Leu Lys Leu Ser Tyr Val Val His Lys Ala Thr Leu
                340                 345                 350

Glu Leu Asn Glu Glu Gly Ala Glu Thr Ala Pro Lys Pro Glu Asp Ser
            355                 360                 365

His Arg Asn Tyr Phe Pro Leu Glu Tyr His Leu Asp His Pro Phe Leu
        370                 375                 380

Phe Val Leu Arg Ala Asn Asp Asn Gly Ala Leu Leu Phe Ile Gly Lys
385                 390                 395                 400

Val Met Asp Pro Lys Gly Phe Ser Phe
                405

<210> SEQ ID NO 35
<211> LENGTH: 1497
<212> TYPE: DNA
<213> ORGANISM: Mus musculus

<400> SEQUENCE: 35
gtcactttaa gaaaagagta gctgtaatct gaagcctgct ggacgctggt tgagaggcag      60
ctactcccct cactgcttcc tggagcccct cagagtgcag gctgtgagag aagctgccgc     120
aaccacagtt ccgggatgca ggccctggtg ctactcctct ggactggagc cctgctcggg     180
cacggcagca gccagaacgt ccccagcagc tctgagggct ccccagtccc ggacagcacg     240
ggcgagcccg tggaggagga ggaccccttc ttcaaggtcc ctgtgaacaa gctggcagca     300
gctgtctcca acttcggcta cgatctgtac cgcctgagat ccagtgccag cccaacgggc     360
aacgtcctgc tgtctccact cagcgtggcc acggccctct ctgccctttc tctgggagct     420
gaacatcgaa cagagtctgt cattcaccgg gctctctact acgacctgat caccaaccct     480
gacatccaca gcacctacaa ggagctcctt gcctctgtta ctgcccctga agagaacctc     540
aagagtgctt ccagaattgt gtttgagagg aaacttcgag tcaaatccag ctttgttgcc     600
cctctggaga agtcctatgg gaccaggccc cggatcctca gggcaaccct cgagtagac      660 cttcaggaga ttaacaactg ggtgcaggcc agatgaaag ggaagattgc ccggtccacg      720
agggaaatgc ccagtgccct cagcatcctt tccttggcg tggcttactt caaggggcag      780
tgggtaacca gtttgactc gagaaagacg accctccagg attttcattt ggacgaggac      840
aggaccgtga gagtccccat gatgtcagat cctaaggcca tcttacgata cggcttggac      900
tctgatctca actgcaagat tgcccagctg cccttgacag aagtatgag catcatcttc      960 ttcctgcccc tgaccgtgac ccagaacttg accatgatag aagagagcct cacctctgag    1020
```

```
ttcattcatg acatcgaccg agaactgaag actatccaag ctgtgctgac tgtccccaag    1080
ctgaagctga gcttcgaagg cgaacttacc aagtctctgc aggacatgaa gctacagtcg    1140
ttgtttgaat cacccgactt cagcaagatt actggcaaac ccgtgaagct cacccaagtg    1200
gaacacaggg ctgctttcga gtggaatgaa gaggggggcag gaagcagccc cagcccaggc    1260
ctccagcccg tccgcctcac cttcccgcta gactatcacc ttaaccaacc tttcctcttt    1320
gttctgaggg acacggacac gggggccctc ctcttcatag gcagaatcct ggaccccagt    1380
agtacttaat gtctcagtgc tctacagaac ccccagaggg aagctgatta tacattccag    1440
gaaggcggcc ggtagcttca gtgtagcctc tgcaataaaa gagcttttcc ttaaaaa       1497
```

<210> SEQ ID NO 36
<211> LENGTH: 416
<212> TYPE: PRT
<213> ORGANISM: Mus musculus

<400> SEQUENCE: 36

```
Met Gln Ala Leu Val Leu Leu Leu Trp Thr Gly Ala Leu Leu Gly His
1               5                   10                  15

Gly Ser Ser Gln Asn Val Pro Ser Ser Glu Gly Ser Pro Val Pro
            20                  25                  30

Asp Ser Thr Gly Glu Pro Val Glu Glu Asp Pro Phe Phe Lys Val
        35                  40                  45

Pro Val Asn Lys Leu Ala Ala Val Ser Asn Phe Gly Tyr Asp Leu
    50                  55                  60

Tyr Arg Leu Arg Ser Ser Ala Ser Pro Thr Gly Asn Val Leu Leu Ser
65                  70                  75                  80

Pro Leu Ser Val Ala Thr Ala Leu Ser Ala Leu Ser Leu Gly Ala Glu
                85                  90                  95

His Arg Thr Glu Ser Val Ile His Arg Ala Leu Tyr Tyr Asp Leu Ile
            100                 105                 110

Thr Asn Pro Asp Ile His Ser Thr Tyr Lys Glu Leu Leu Ala Ser Val
        115                 120                 125

Thr Ala Pro Glu Lys Asn Leu Lys Ser Ala Ser Arg Ile Val Phe Glu
    130                 135                 140

Arg Lys Leu Arg Val Lys Ser Ser Phe Val Ala Pro Leu Glu Lys Ser
145                 150                 155                 160

Tyr Gly Thr Arg Pro Arg Ile Leu Thr Gly Asn Pro Arg Val Asp Leu
                165                 170                 175

Gln Glu Ile Asn Asn Trp Val Gln Ala Met Lys Gly Lys Ile Ala
            180                 185                 190

Arg Ser Thr Arg Glu Met Pro Ser Ala Leu Ser Ile Leu Leu Leu Gly
        195                 200                 205

Val Ala Tyr Phe Lys Gly Gln Trp Val Thr Lys Phe Asp Ser Arg Lys
    210                 215                 220

Thr Thr Leu Gln Asp Phe His Leu Asp Glu Asp Arg Thr Val Arg Val
225                 230                 235                 240

Pro Met Met Ser Asp Pro Lys Ala Ile Leu Arg Tyr Gly Leu Asp Ser
                245                 250                 255

Asp Leu Asn Cys Lys Ile Ala Gln Leu Pro Leu Thr Gly Ser Met Ser
            260                 265                 270

Ile Ile Phe Phe Leu Pro Leu Thr Val Thr Gln Asn Leu Thr Met Ile
        275                 280                 285
```

```
Glu Glu Ser Leu Thr Ser Glu Phe Ile His Asp Ile Asp Arg Glu Leu
    290                 295                 300
Lys Thr Ile Gln Ala Val Leu Thr Val Pro Lys Leu Lys Leu Ser Phe
305                 310                 315                 320
Glu Gly Glu Leu Thr Lys Ser Leu Gln Asp Met Lys Leu Gln Ser Leu
                325                 330                 335
Phe Glu Ser Pro Asp Phe Ser Lys Ile Thr Gly Lys Pro Val Lys Leu
            340                 345                 350
Thr Gln Val Glu His Arg Ala Ala Phe Glu Trp Asn Glu Glu Gly Ala
        355                 360                 365
Gly Ser Ser Pro Ser Pro Gly Leu Gln Pro Val Arg Leu Thr Phe Pro
    370                 375                 380
Leu Asp Tyr His Leu Asn Gln Pro Phe Leu Phe Val Leu Arg Asp Thr
385                 390                 395                 400
Asp Thr Gly Ala Leu Leu Phe Ile Gly Arg Ile Leu Asp Pro Ser Ser
                405                 410                 415

<210> SEQ ID NO 37
<211> LENGTH: 1810
<212> TYPE: DNA
<213> ORGANISM: Salmo salar

<400> SEQUENCE: 37
cacgggcggg cgacgtggcc cataatcgtg ctaaaaggat gctgcggacg accctgttgc     60
tgtgtctggg ggccctcctc tcgctctctt atgctcagtt gttggagaca gaggcggcgg    120
gaggggaaga ggaagctgtg gagctcttta ccacgcccag agcaaagatg ccgctgccca    180
cctctgactt cggctacaac ctgttccggg ccttggcggg tcgcaacccc aatactaacg    240
tgttcctggc cccatcagc atctctgcgg tgctcactca gctatccatg ggagcgtctc    300
cggatcgttc agagaggtgg ttatacagag ctctgaggta tcacaccctg caggaccctc    360
agctccacga cacactcaga gacctacttg cctcactcag agcacctgga aaaggcctca    420
gcatcgctgc acgtgtctac ctggcccgca ggctgcgtct gaagcaggaa tactttggcg    480
tggtggagaa gcagtatggg gtgcggccca aggctctgat gggcgggggct aaagatgtga    540 atgagatcaa tgattgggtc aaacagcaga cgggcggcaa ggtcgaccgc ttcatgtcca    600
agcccctggg acggaactct ggtgtggttc tctgggcgc ggcctacttc aaagtgaagt    660
ggatgactcg gttcagtcag agtggagtga tggaggactt ccagcttgtt ggagaggctc    720
ccgcccgcat ttccatgatg cagcaggaca attacccggt gaagatgggg gtagacccag    780
acctgggctg tacaattgct cagatccaga tgcaggatga cgtcagcatg tttgtgttcc    840
ttcctgatga tgtcactcag aacatgacct tggtggagga gagcctgaca gctgagtttg    900
ttcaggacct ctccatgacc cttcaccccg tgcagacggc cctcacactg cctgtcctaa    960
aattcagcta ctccactgac ctgctgccac tgctcactga cctgggtctc gacgaatttc   1020
tggcagacac ggacctgacc aagatcacgt ctcaggcggc gaagctcggc agcctcaatc   1080
ataaggttgt catggagatg gccccagagg gcacccagta tgccagctcc ctccccgcct   1140
ccacacccct tccgtactgc gtggaccatc ccttcctgtt cctggtgagg gatgaggcct   1200
cgggagcact gctctttatt ggcaaggtgg tcaacccacg caatctgagg atataaacac   1260
agacacacac tgccttctaa gcaggtccta ggagggatc agccatcgtt aagcttaagc   1320
ttctgtgtgt cataaatgca caatatgaga gggtggataa gcagctagat ttacccattg   1380
atcatataat acagtttctt aatcatgtat ggaaaccatg cataacattc agactaaaag   1440
```

-continued

```
ttcagaccaa aagtctgaac actcacaact gatagtctca agttgttttc agggaaaata    1500
atttgtgatt gaaaagtaca gctctcataa tttttaaata gaggcacatt ctttaacccc    1560
aaaaatactc atcataatat tgtcaattgc gatgcaagaa ataaacattg aagttaagtc    1620
tttctgtttg tctgtctgac tccatagatg gaattgtata actttatcca gttgacatac    1680
aatagctgct tccagtaaag ggttgggtta ttttggaaag aaattggact cttggatgct    1740
ctttccttag ctattgtgct gttaaacaaa attaaaggac taacacaaaa aaaaaaaaa    1800 aaaaaaaga                                                            1810
```

<210> SEQ ID NO 38
<211> LENGTH: 405
<212> TYPE: PRT
<213> ORGANISM: Salmo salar

<400> SEQUENCE: 38

```
Met Leu Arg Thr Thr Leu Leu Leu Cys Leu Gly Ala Leu Leu Ser Leu
 1               5                  10                  15

Ser Tyr Ala Gln Leu Leu Glu Thr Glu Ala Ala Gly Gly Glu Glu Glu
                20                  25                  30

Ala Val Glu Leu Phe Thr Thr Pro Arg Ala Lys Met Ala Ala Ala Thr
            35                  40                  45

Ser Asp Phe Gly Tyr Asn Leu Phe Arg Ala Leu Ala Gly Arg Asn Pro
        50                  55                  60

Asn Thr Asn Val Phe Leu Ala Pro Ile Ser Ile Ser Ala Val Leu Thr
65                  70                  75                  80

Gln Leu Ser Met Gly Ala Ser Pro Asp Arg Ser Glu Arg Trp Leu Tyr
                85                  90                  95

Arg Ala Leu Arg Tyr His Thr Leu Gln Asp Pro Gln Leu His Asp Thr
            100                 105                 110

Leu Arg Asp Leu Leu Ala Ser Leu Arg Ala Pro Gly Lys Gly Leu Ser
        115                 120                 125

Ile Ala Ala Arg Val Tyr Leu Ala Arg Arg Leu Arg Leu Lys Gln Glu
    130                 135                 140

Tyr Phe Gly Val Val Glu Lys Gln Tyr Gly Val Arg Pro Lys Ala Leu
145                 150                 155                 160

Met Gly Gly Ala Lys Asp Val Asn Glu Ile Asn Asp Trp Val Lys Gln
                165                 170                 175

Gln Thr Gly Gly Lys Val Asp Arg Phe Met Ser Lys Pro Leu Gly Arg
            180                 185                 190

Asn Ser Gly Val Val Pro Leu Gly Ala Ala Tyr Phe Lys Val Lys Trp
        195                 200                 205

Met Thr Arg Phe Ser Gln Ser Gly Val Met Glu Asp Phe Gln Leu Val
    210                 215                 220

Gly Glu Ala Pro Ala Arg Ile Ser Met Met Gln Gln Asp Asn Tyr Pro
225                 230                 235                 240

Val Lys Met Gly Val Asp Pro Asp Leu Gly Cys Thr Ile Ala Gln Ile
                245                 250                 255

Gln Met Gln Asp Asp Val Ser Met Phe Val Phe Leu Pro Asp Asp Val
            260                 265                 270

Thr Gln Asn Met Thr Leu Val Glu Glu Ser Leu Thr Ala Glu Phe Val
        275                 280                 285

Gln Asp Leu Ser Met Thr Leu His Pro Val Gln Thr Ala Leu Thr Leu
    290                 295                 300
```

```
Pro Val Leu Lys Phe Ser Tyr Ser Thr Asp Leu Pro Leu Leu Thr
305                 310                 315                 320

Asp Leu Gly Leu Asp Glu Phe Leu Ala Asp Thr Asp Leu Thr Lys Ile
            325                 330                 335

Thr Ser Gln Ala Ala Lys Leu Gly Ser Leu Asn His Lys Val Val Met
        340                 345                 350

Glu Met Ala Pro Glu Gly Thr Gln Tyr Ala Ser Ser Leu Pro Ala Ser
    355                 360                 365

Thr Pro Leu Ser Tyr Cys Val Asp His Pro Phe Leu Phe Leu Val Arg
370                 375                 380

Asp Glu Ala Ser Gly Ala Leu Leu Phe Ile Gly Lys Val Val Asn Pro
385                 390                 395                 400

Arg Asn Leu Arg Ile
            405

<210> SEQ ID NO 39
<211> LENGTH: 1422
<212> TYPE: DNA
<213> ORGANISM: Ovis aries

<400> SEQUENCE: 39
ggctgggcgt ggagcggcgg tgcacccaca ggccccgaga tgcaggccct cgtgctactc      60
ctctggactg gagccctcct tgggtttggc cactgtcaga acgccggccc ggaggcgggc     120
tccctggccc ctgagagcac aggggcaccc gtggaggaag aggatcccct cttcaaggtc     180
cccgtgaaca agctggcggc agccgtctcc aacttcggct acgacctgta ccgcgtgaga     240
tctggcgaga gccccaccac caacgtgctg ctgtctccgc tcagcgtggc cacggcgctc     300
tctgccctgt cgctgggtgc ggaacagcgg acagaatcca gcattaccg ggctctgtac      360
tacgacctga tcagtaaccc agacatccac ggcacctaca aggacctcct gcctccgtc      420
actgccccc agaagaacct taaagtgct tccggatta tctttgagag gaagctgcgg        480
ataaaagcca gcttcgtccc acccctcgag aagtcatatg ggaccaggcc cagaatcctg     540
accggcaact ctcgaataga ccttcaggag attaacaact gggtgcaggc ccagatgaaa     600
gggaaaattg ctagatccac acgggaaata cccagtggaa tcagcattct ccttcttggt    660
gtggcttact tcaaggggca gtgggtaaca aagtttgact ccaggaagac ttccctggag    720
gatttccact ggatgagggg aggaccgtg aaagttccca tgatgtcaga ccctaaggcc     780
gttttacggt acggcttgga ttctgatctc aactgcaaga tcgcccagct gcccttgacc    840
gggagcacaa gtatcatctt cttcctgcct cagaaagtga cccagaactt gaccttgata    900
gaagagagcc tcacctctga gttcattcat gacatagacc gagaactgaa gactgttcag    960
gcagtcctga ccattcccaa gctgaagctg agttatgaag gcgaactcac gaagtctgtg   1020
caggagctga agctacaatc cctgtttgat gcaccagact ttagcaagat cacaggcaaa   1080
cctatcaaac ttactcaagt ggaacatcgc atcggattcg agtggaatga ggatgggcg   1140
ggtactaact ccagcccagg ggtccagcct gcccgcctca ccttccctct ggactatcac   1200
cttaaccaac ctttcatctt tgtactgagg gacacagaca caggggccct tctcttcata   1260
ggcaaaattc tggacccag aggcacttaa tactcaactt aatgttcaaa taccccagaa    1320
gaaaaaaaca ctagcgggat ggcagattat atattatatg aaggctgccc ctacgtttca    1380
atgtatactt tgcaataaaa gtgctttctc cttaaaaaaa aa                       1422
```

```
<210> SEQ ID NO 40
<211> LENGTH: 416
<212> TYPE: PRT
<213> ORGANISM: Ovis aries

<400> SEQUENCE: 40

Met Gln Ala Leu Val Leu Leu Leu Trp Thr Gly Ala Leu Leu Gly Phe
1               5                   10                  15

Gly His Cys Gln Asn Ala Gly Pro Glu Ala Gly Ser Leu Ala Pro Glu
            20                  25                  30

Ser Thr Gly Ala Pro Val Glu Glu Asp Pro Phe Phe Lys Val Pro
        35                  40                  45

Val Asn Lys Leu Ala Ala Val Ser Asn Phe Gly Tyr Asp Leu Tyr
50                  55                  60

Arg Val Arg Ser Gly Glu Ser Pro Thr Asn Val Leu Leu Ser Pro
65                  70                  75                  80

Leu Ser Val Ala Thr Ala Leu Ser Ala Leu Ser Leu Gly Ala Glu Gln
                85                  90                  95

Arg Thr Glu Ser Ser Ile His Arg Ala Leu Tyr Tyr Asp Leu Ile Ser
            100                 105                 110

Asn Pro Asp Ile His Gly Thr Tyr Lys Asp Leu Leu Ala Ser Val Thr
            115                 120                 125

Ala Pro Gln Lys Asn Leu Lys Ser Ala Ser Arg Ile Ile Phe Glu Arg
130                 135                 140

Lys Leu Arg Ile Lys Ala Ser Phe Val Pro Leu Glu Lys Ser Tyr
145                 150                 155                 160

Gly Thr Arg Pro Arg Ile Leu Thr Gly Asn Ser Arg Ile Asp Leu Gln
                165                 170                 175

Glu Ile Asn Asn Trp Val Gln Ala Gln Met Lys Gly Lys Ile Ala Arg
            180                 185                 190

Ser Thr Arg Glu Ile Pro Ser Gly Ile Ser Ile Leu Leu Leu Gly Val
            195                 200                 205

Ala Tyr Phe Lys Gly Gln Trp Val Thr Lys Phe Asp Ser Arg Lys Thr
210                 215                 220

Ser Leu Glu Asp Phe His Leu Asp Glu Gly Arg Thr Val Lys Val Pro
225                 230                 235                 240

Met Met Ser Asp Pro Lys Ala Val Leu Arg Tyr Gly Leu Asp Ser Asp
                245                 250                 255

Leu Asn Cys Lys Ile Ala Gln Leu Pro Leu Thr Gly Ser Thr Ser Ile
            260                 265                 270

Ile Phe Phe Leu Pro Gln Lys Val Thr Gln Asn Leu Thr Leu Ile Glu
            275                 280                 285

Glu Ser Leu Thr Ser Glu Phe Ile His Asp Ile Asp Arg Glu Leu Lys
290                 295                 300

Thr Val Gln Ala Val Leu Thr Ile Pro Lys Leu Lys Leu Ser Tyr Glu
305                 310                 315                 320

Gly Glu Leu Thr Lys Ser Val Gln Glu Leu Lys Leu Gln Ser Leu Phe
                325                 330                 335

Asp Ala Pro Asp Phe Ser Lys Ile Thr Gly Lys Pro Ile Lys Leu Thr
            340                 345                 350

Gln Val Glu His Arg Ile Gly Phe Glu Trp Asn Glu Asp Gly Ala Gly
            355                 360                 365

Thr Asn Ser Ser Pro Gly Val Gln Pro Ala Arg Leu Thr Phe Pro Leu
370                 375                 380
```

Asp Tyr His Leu Asn Gln Pro Phe Ile Phe Val Leu Arg Asp Thr Asp
385                 390                 395                 400

Thr Gly Ala Leu Leu Phe Ile Gly Lys Ile Leu Asp Pro Arg Gly Thr
            405                 410                 415

<210> SEQ ID NO 41
<211> LENGTH: 1465
<212> TYPE: DNA
<213> ORGANISM: Cavia porcellus

<400> SEQUENCE: 41

```
gtgcagactg agcaggacct gaactggagt acggctggga gcagagctgc agggaaccac      60
aggttcagga tgcaggtcct tgtgctactc ctctggaccg gagccctgct agggcgtggc     120
agctgccagg acatcgccag caacccggag gactccccgt ccctgaaaag cacaggggag     180
ccagtggagg aggaggaccc cttcttcaag gtccctgtga acaagctggc tgcagccatc     240
tccaactttg ctacgaccta taccggggtg agatccatcg agagcccac caccaatgtg     300
ctgctgtccc ccctcagcgt ggccaccgcc ctctctgccc tttcgctggg ggcggaacag     360
cgaacagaag ccaccattca tcgggctctc tactatgaca tgatcagcaa ccctgacatc     420
cacagcacct acaaggagct cctggccact gtcaccgccc gcagaagaa cctgaagagt     480
gcttcgagga ttgtctttga gaggaagctg cgcataaaat ccagccttgt cgcactactg     540
gaaaagtcat attcgaccag gcccagaatc ctgactggca ccctcgcat tgaccttcaa     600
gagattagca actgggtgca ggcccagatg aaagggaaaa tcaccaggtc tacgagggaa     660
gtgcccagtg gcatcagcat tctccttctc ggtgtggctt acttcaaggg gcagtgggtc     720
acaaaatttg actccagaaa gacttctctc caggatttcc acttggatga ggagaggact     780
gtaaaagttc ccatgatgtc agaccccaag gccatcatac gctatggcct ggatactgat     840
ctcaactgca agattgccca gctgcccttg actggaagca tgagtatcat cttcttcttg     900
cccatgaggg caacccagaa cttgaccatg atagaagaga gcctcaccct cgagtttgtt     960
catgacataa accgagaact gaaggctgtc caagcggttc tcagcatccc aggctgaag     1020
ctgagttttcg aaggcgaact taccaagtcc ctgcaggaga tgaagctgca ttccttgttt    1080
gagtccccccg actttagcaa gatcacaggc aaacctatca agctgactca gtggaacac     1140
cgggctggtt tcgagtggaa tgaggagggg gcgccaggaa ccagcaccaa ctcagacctc     1200
cagcctactg gcttcacatt ctctctggac tatcacctga ccagccgtt catcttcgtc     1260
ctgagagaca cggacacggg ggcccttctc ttcataggca aaattctgga ccccagaagt     1320
acttaatgct ccagtttaat gttctactac tctagaaaga accccagaa ggatggcagt      1380
ttatacatta caggggggca gcccccacag tttcagtgta ctttgcaa taaaagagct      1440
ttatccttaa aaaaaaaaa aaaaa                                            1465
```

<210> SEQ ID NO 42
<211> LENGTH: 418
<212> TYPE: PRT
<213> ORGANISM: Cavia porcellus

<400> SEQUENCE: 42

Met Gln Val Leu Val Leu Leu Leu Trp Thr Gly Ala Leu Leu Gly Arg
1               5                   10                  15

Gly Ser Cys Gln Asp Ile Ala Ser Asn Pro Glu Asp Ser Pro Ser Pro
            20                  25                  30

Glu Ser Thr Gly Glu Pro Val Glu Glu Glu Asp Pro Phe Phe Lys Val

```
                35                  40                  45
Pro Val Asn Lys Leu Ala Ala Ile Ser Asn Phe Gly Tyr Asp Leu
 50                  55                  60
Tyr Arg Val Arg Ser Ile Glu Ser Pro Thr Thr Asn Val Leu Leu Ser
 65                  70                  75                  80
Pro Leu Ser Val Ala Thr Ala Leu Ser Ala Leu Ser Leu Gly Ala Glu
                 85                  90                  95
Gln Arg Thr Glu Ala Thr Ile His Arg Ala Leu Tyr Tyr Asp Met Ile
                100                 105                 110
Ser Asn Pro Asp Ile His Ser Thr Tyr Lys Glu Leu Leu Ala Thr Val
                115                 120                 125
Thr Ala Pro Gln Lys Asn Leu Lys Ser Ala Ser Arg Ile Val Phe Glu
130                 135                 140
Arg Lys Leu Arg Ile Lys Ser Ser Leu Val Ala Leu Leu Glu Lys Ser
145                 150                 155                 160
Tyr Ser Thr Arg Pro Arg Ile Leu Thr Gly Asn Pro Arg Ile Asp Leu
                165                 170                 175
Gln Glu Ile Ser Asn Trp Val Gln Ala Gln Met Lys Gly Lys Ile Thr
                180                 185                 190
Arg Ser Thr Arg Glu Val Pro Ser Gly Ile Ser Ile Leu Leu Leu Gly
                195                 200                 205
Val Ala Tyr Phe Lys Gly Gln Trp Val Thr Lys Phe Asp Ser Arg Lys
                210                 215                 220
Thr Ser Leu Gln Asp Phe His Leu Asp Glu Glu Arg Thr Val Lys Val
225                 230                 235                 240
Pro Met Met Ser Asp Pro Lys Ala Ile Ile Arg Tyr Gly Leu Asp Thr
                245                 250                 255
Asp Leu Asn Cys Lys Ile Ala Gln Leu Pro Leu Thr Gly Ser Met Ser
                260                 265                 270
Ile Ile Phe Phe Leu Pro Met Arg Ala Thr Gln Asn Leu Thr Met Ile
                275                 280                 285
Glu Glu Ser Leu Thr Ser Glu Phe Val His Asp Ile Asn Arg Glu Leu
                290                 295                 300
Lys Ala Val Gln Ala Val Leu Ser Ile Pro Arg Leu Lys Leu Ser Phe
305                 310                 315                 320
Glu Gly Glu Leu Thr Lys Ser Leu Gln Glu Met Lys Leu His Ser Leu
                325                 330                 335
Phe Glu Ser Pro Asp Phe Ser Lys Ile Thr Gly Lys Pro Ile Lys Leu
                340                 345                 350
Thr Gln Val Glu His Arg Ala Gly Phe Glu Trp Asn Glu Glu Gly Ala
                355                 360                 365
Pro Gly Thr Ser Thr Asn Ser Asp Leu Gln Pro Thr Gly Phe Thr Phe
                370                 375                 380
Ser Leu Asp Tyr His Leu Asn Gln Pro Phe Ile Phe Val Leu Arg Asp
385                 390                 395                 400
Thr Asp Thr Gly Ala Leu Leu Phe Ile Gly Lys Ile Leu Asp Pro Arg
                405                 410                 415
Ser Thr

<210> SEQ ID NO 43
<211> LENGTH: 1408
<212> TYPE: DNA
<213> ORGANISM: Bos taurus
```

-continued

<400> SEQUENCE: 43

```
gaggtgcacc cacaggcccc gagatgcagg ccctcgtgct actcctctgg actggagccc      60
tgcttgggtt tggccgctgc cagaacgccg gccaggaggc gggctctctg accctgaga     120
gcacggggc accagtggag gaagaggatc ccttcttcaa ggtccctgtg aacaagctgg     180
cggcagcggt ctccaacttc ggctacgacc tgtaccgcgt gagatccggt gagagcccca    240
ccgccaatgt gctgctgtct ccgctcagcg tggccacggc gctctctgcc ctgtcgctgg    300
gtgcggaaca gcggacagaa tccaacattc accgggctct gtactacgac ctgatcagta    360
acccagacat ccacggcacc tacaaggacc tccttgcctc cgtcaccgcc cccagaaga    420
accttaagag tgcttcccgg attatctttg agaggaagct gcggataaaa gccagcttca    480
tcccacccct ggagaagtca tatgggacca ggcccagaat cctgaccggc aactctcgag    540
tagaccttca ggagattaac aactgggtgc aggcccagat gaaagggaaa gtcgctaggt    600
ccacgaggga gatgcccagt gagatcagca ttttcctcct gggcgtggct tacttcaagg    660
ggcagtgggt aacaaagttt gactccagaa aaacttccct ggaggatttc tacttggatg    720
aggagaggac cgtgaaagtc cccatgatgt cagaccctca ggccgtttta cggtacggct    780
tggattctga tctcaactgc aagatcgccc agctgcccct gaccgggagc acaagtatca    840
tcttcttcct gcctcagaaa gtgacccaga acttgacctt gatagaagag agcctcacct    900
ctgagttcat tcatgacata gaccgagaac tgaagactgt tcaggcggtc ctgaccattc    960
ccaagctgaa gctgagttat gaaggcgaac tcacgaagtc cgtgcaggag ctgaagctgc   1020
aatccctgtt tgatgcacca gactttagca agatcacagg caaacctatc aaacttactc   1080
aagtggaaca tcgcgtcgga tttgagtgga atgaggatgg ggcgggtact aactccagcc   1140
caggggtcca gcctgcccgc ctcaccttcc ctctggacta tcaccttaac caacctttca   1200
tctttgtact gagggacaca gacacagggg cccttctctt cataggcaaa attctggacc   1260
ccaggggcac ttagtactcc aactaaatgt tcaaataccc cagaagaaaa aaacactaga   1320
gggatggcag attatatatt atacgaaggc tgcccctaca tttcaatgta actttgcaa    1380
taaaagtgct ttatccttaa aaaaaaaa                                       1408
```

<210> SEQ ID NO 44
<211> LENGTH: 416
<212> TYPE: PRT
<213> ORGANISM: Bos taurus

<400> SEQUENCE: 44

```
Met Gln Ala Leu Val Leu Leu Leu Trp Thr Gly Ala Leu Leu Gly Phe
1               5                   10                  15

Gly Arg Cys Gln Asn Ala Gly Gln Glu Ala Gly Ser Leu Thr Pro Glu
            20                  25                  30

Ser Thr Gly Ala Pro Val Glu Glu Asp Pro Phe Phe Lys Val Pro
        35                  40                  45

Val Asn Lys Leu Ala Ala Ala Val Ser Asn Phe Gly Tyr Asp Leu Tyr
    50                  55                  60

Arg Val Arg Ser Gly Glu Ser Pro Thr Ala Asn Val Leu Leu Ser Pro
65                  70                  75                  80

Leu Ser Val Ala Thr Ala Leu Ser Ala Leu Ser Leu Gly Ala Glu Gln
                85                  90                  95

Arg Thr Glu Ser Asn Ile His Arg Ala Leu Tyr Tyr Asp Leu Ile Ser
            100                 105                 110
```

Asn Pro Asp Ile His Gly Thr Tyr Lys Asp Leu Leu Ala Ser Val Thr
            115                 120                 125

Ala Pro Gln Lys Asn Leu Lys Ser Ala Ser Arg Ile Ile Phe Glu Arg
130                 135                 140

Lys Leu Arg Ile Lys Ala Ser Phe Ile Pro Leu Glu Lys Ser Tyr
145                 150                 155                 160

Gly Thr Arg Pro Arg Ile Leu Thr Gly Asn Ser Arg Val Asp Leu Gln
                165                 170                 175

Glu Ile Asn Asn Trp Val Gln Ala Gln Met Lys Gly Lys Val Ala Arg
            180                 185                 190

Ser Thr Arg Glu Met Pro Ser Glu Ile Ser Ile Phe Leu Leu Gly Val
        195                 200                 205

Ala Tyr Phe Lys Gly Gln Trp Val Thr Lys Phe Asp Ser Arg Lys Thr
    210                 215                 220

Ser Leu Glu Asp Phe Tyr Leu Asp Glu Glu Arg Thr Val Lys Val Pro
225                 230                 235                 240

Met Met Ser Asp Pro Gln Ala Val Leu Arg Tyr Gly Leu Asp Ser Asp
                245                 250                 255

Leu Asn Cys Lys Ile Ala Gln Leu Pro Leu Thr Gly Ser Thr Ser Ile
            260                 265                 270

Ile Phe Phe Leu Pro Gln Lys Val Thr Gln Asn Leu Thr Leu Ile Glu
        275                 280                 285

Glu Ser Leu Thr Ser Glu Phe Ile His Asp Ile Asp Arg Glu Leu Lys
    290                 295                 300

Thr Val Gln Ala Val Leu Thr Ile Pro Lys Leu Lys Leu Ser Tyr Glu
305                 310                 315                 320

Gly Glu Leu Thr Lys Ser Val Gln Glu Leu Lys Leu Gln Ser Leu Phe
                325                 330                 335

Asp Ala Pro Asp Phe Ser Lys Ile Thr Gly Lys Pro Ile Lys Leu Thr
            340                 345                 350

Gln Val Glu His Arg Val Gly Phe Glu Trp Asn Glu Asp Gly Ala Gly
        355                 360                 365

Thr Asn Ser Ser Pro Gly Val Gln Pro Ala Arg Leu Thr Phe Pro Leu
    370                 375                 380

Asp Tyr His Leu Asn Gln Pro Phe Ile Phe Val Leu Arg Asp Thr Asp
385                 390                 395                 400

Thr Gly Ala Leu Leu Phe Ile Gly Lys Ile Leu Asp Pro Arg Gly Thr
                405                 410                 415

<210> SEQ ID NO 45
<211> LENGTH: 1418
<212> TYPE: DNA
<213> ORGANISM: Sus scrofa

<400> SEQUENCE: 45
agtgcacgga cctaggctgg gcgtggagct gcagcgcacc cacaggcccc gggatgcagg    60
ccctcgtgct actcctctgg actggagccc tcctcgggtc tggcagctgc cagaacgctg   120
gcccggagga gggctccccg gcccctgaca cggtgggggc gccagtggag gaggaggatc   180
ccttcttcaa ggtccctgtg aacaagctgg cggcggccgt ctccaacttt ggttacgacc   240
tgtaccgagt gagatccagc gagagcccca ccgccaacgt gctcctgtct ccctcagcg    300 tggccacggc gctctctgcc ctgtctctgg gagccgaaca gcggacagaa tccagcctcc   360
accgggctct ctactatgac ctgatcagca acccggacct ccacggcacc tacaaggagc   420

```
tccttgctgc cgtcactgcc ccccagaaga acctcaagag tgcttcccgg atcatctttg    480
agaagaagct gcggataaaa gccagctttg ttgcacccct ggaaaagtca tacgggacca    540
ggcccagaat tctgaccggc aactcccgct tggaccttca ggaggttaac aactgggtgc    600
aggctcagac gaaagggaaa gtcgccaggt ccacgcggga actgcccggc gaaatcagca    660
tcctccttct tggtgtggct tacttcaagg ggcagtgggt aaccaagttt gactccagga    720
agacgtcgct ggaggatttc cacttggatg aggagagaac cgtgaaggtg cccatgatgt    780
cagaccctaa ggccgtttta cgctacggct tggattctga tctcaactgc aagattgccc    840
agctgccctt gaccggaagc atgagtatca tcttcttcct gcctctgaaa gtgacccaga    900
acctgaccat gatagaagag agcctcacct ctgagttcat tcacgacata gaccgagaac    960
tgaagacggt tcaagcggtc ctgaccgtcc ccaagctgaa gctgagttac gaaggcgaac   1020
tcacgaagtc tgtgcaggaa ctgaagctgc aatccttgtt tgattcacca gactttagca   1080
agatcacggg caaacctatc aaacttactc aagtggaaca tcgcattggc tttgagtgga   1140
acgaggatgg gggaagcgcc acctccagcc cagggccccg cctcaccttc ccctggact    1200
atcaccttaa ccagcctttc atctttgtac tgagggacac agacacagga gcccttctct   1260
tcataggcaa gattctggac cccaggaca cttaatgctc tagtttaatg ttcaaatatc    1320
ccagaagaag aaaactctag acagatggca gattatatat tacacgaaag ctgcacatat   1380
gtttcaatgt atactttgca ataaaagtgc tttatccc                            1418
```

<210> SEQ ID NO 46
<211> LENGTH: 413
<212> TYPE: PRT
<213> ORGANISM: Sus scrofa

<400> SEQUENCE: 46

```
Met Gln Ala Leu Val Leu Leu Leu Trp Thr Gly Ala Leu Leu Gly Ser
1               5                   10                  15

Gly Ser Cys Gln Asn Ala Gly Pro Glu Gly Ser Pro Ala Pro Asp
            20                  25                  30

Thr Val Gly Ala Pro Val Glu Glu Asp Pro Phe Phe Lys Val Pro
        35                  40                  45

Val Asn Lys Leu Ala Ala Ala Val Ser Asn Phe Gly Tyr Asp Leu Tyr
    50                  55                  60

Arg Val Arg Ser Ser Glu Ser Pro Thr Ala Asn Val Leu Leu Ser Pro
65                  70                  75                  80

Leu Ser Val Ala Thr Ala Leu Ser Ala Leu Ser Leu Gly Ala Glu Gln
                85                  90                  95

Arg Thr Glu Ser Ser Leu His Arg Ala Leu Tyr Tyr Asp Leu Ile Ser
            100                 105                 110

Asn Pro Asp Leu His Gly Thr Tyr Lys Glu Leu Leu Ala Ala Val Thr
        115                 120                 125

Ala Pro Gln Lys Asn Leu Lys Ser Ala Ser Arg Ile Ile Phe Glu Lys
    130                 135                 140

Lys Leu Arg Ile Lys Ala Ser Phe Val Ala Pro Leu Glu Lys Ser Tyr
145                 150                 155                 160

Gly Thr Arg Pro Arg Ile Leu Thr Gly Asn Ser Arg Leu Asp Leu Gln
                165                 170                 175

Glu Val Asn Asn Trp Val Gln Ala Gln Thr Lys Gly Lys Val Ala Arg
            180                 185                 190

Ser Thr Arg Glu Leu Pro Gly Glu Ile Ser Ile Leu Leu Leu Gly Val
```

```
            195                 200                 205
Ala Tyr Phe Lys Gly Gln Trp Val Thr Lys Phe Asp Ser Arg Lys Thr
    210                 215                 220
Ser Leu Glu Asp Phe His Leu Asp Glu Glu Arg Thr Val Lys Val Pro
225                 230                 235                 240
Met Met Ser Asp Pro Lys Ala Val Leu Arg Tyr Gly Leu Asp Ser Asp
                245                 250                 255
Leu Asn Cys Lys Ile Ala Gln Leu Pro Leu Thr Gly Ser Met Ser Ile
                260                 265                 270
Ile Phe Phe Leu Pro Leu Lys Val Thr Gln Asn Leu Thr Met Ile Glu
            275                 280                 285
Glu Ser Leu Thr Ser Glu Phe Ile His Asp Ile Asp Arg Glu Leu Lys
    290                 295                 300
Thr Val Gln Ala Val Leu Thr Val Pro Lys Leu Lys Leu Ser Tyr Glu
305                 310                 315                 320
Gly Glu Leu Thr Lys Ser Val Gln Glu Leu Lys Leu Gln Ser Leu Phe
                325                 330                 335
Asp Ser Pro Asp Phe Ser Lys Ile Thr Gly Lys Pro Ile Lys Leu Thr
                340                 345                 350
Gln Val Glu His Arg Ile Gly Phe Glu Trp Asn Glu Asp Gly Gly Ser
            355                 360                 365
Ala Thr Ser Ser Pro Gly Pro Arg Leu Thr Phe Pro Leu Asp Tyr His
    370                 375                 380
Leu Asn Gln Pro Phe Ile Phe Val Leu Arg Asp Thr Asp Thr Gly Ala
385                 390                 395                 400
Leu Leu Phe Ile Gly Lys Ile Leu Asp Pro Arg Ser Thr
                405                 410
```

<210> SEQ ID NO 47
<211> LENGTH: 1317
<212> TYPE: DNA
<213> ORGANISM: Ornithorhynchus anatinus

<400> SEQUENCE: 47

```
agtgtgcaga cttrgtttaa ccacagttgg tagccgagct gaagagaatc cccaggcccc    60
acaatgcagc cctttgcggt actcctgtgg gtgggagtcc tcatcggctc agtaagtcc    120
caggatgccg ctgggcctga ggaatctcca gctcccgacg ccacggggac tgcggtggtg    180
gaggaggagg acccttctt caaggtccct gtgaacaagc tggcagccgc cgtctccaac    240
tttggctacg acctgtatcg ccagaaatcc agctcgagcc ccaccaccaa tgtgctgctg    300
tccctctca gtgtggccac cgctctctct agcctctcct tgggtgctgg gccccggacg    360
gaaagcctca tacaccgggc tcttattat gacttgattc acaacccgga catccacggc    420
acttacaagg aacttctcgc tacagtcacc gctccgcaaa agaacctgaa gactgcttcc    480
cggcttgtct tggagagaaa gctgcggata aagctggat cgttgggct gctgaaaag    540
tcgtatggat ccaggccgaa gattctgacg ggcaacactc ggactgacct tcacgaaatg    600
aacaactgga tgcagaccca gactaagggg aagatgggcc ggacgctgaa ggagctgccc    660
agtggaatta gcgttcttct tcttgggata gcttacttca aagggcagtg ggtgactaag    720
tttgatccca gaagacttcc cctgcaggac ttccacttgg atgaagaccg aactgtaaaa    780
gtccccatga tgtcagatcc caaggctatc atacgctacg gcctggactc cgacctcaac    840
tgcaagattg cccagctgcc cctggaggga agcatgagcg tcatttctt cctgccgctg    900
```

-continued

```
aaagcaaccc agaacctgac gctcatagag gagagtctca cctcagagtt cattcacgac    960
attgacagag agctgaagac catccaggcg gtgctaactg tacccaagct tcagctcagc   1020
ttcgagggag aagtgtccaa acatttcag gagataaagc ttcagtctct cttcaactcc   1080
ccggatctca gcaagatcac gcccagaccc atcaagctca ctcacgtggt gcaccggtca   1140
tctctggaat ggagtgagga tggggtgggg gacgccccca gccccgcgct actgcccgct   1200
cgactgacct tccccctgga ctaccacctc aaccagcctt tcatctttgt cttgcgggac   1260
actgacacgg gcaccctttct cttcattggc aaaatcctgg accccagggg caactga     1317
```

<210> SEQ ID NO 48
<211> LENGTH: 417
<212> TYPE: PRT
<213> ORGANISM: Ornithorhynchus anatinus

<400> SEQUENCE: 48

```
Met Gln Pro Phe Ala Val Leu Leu Trp Val Gly Val Leu Ile Gly Ser
 1               5                  10                  15

Ser Lys Ser Gln Asp Ala Ala Gly Pro Glu Glu Ser Pro Ala Pro Asp
            20                  25                  30

Ala Thr Gly Thr Ala Val Val Glu Glu Glu Asp Pro Phe Phe Lys Val
        35                  40                  45

Pro Val Asn Lys Leu Ala Ala Ala Val Ser Asn Phe Gly Tyr Asp Leu
    50                  55                  60

Tyr Arg Gln Lys Ser Ser Ser Pro Thr Thr Asn Val Leu Leu Ser
 65                  70                  75                  80

Pro Leu Ser Val Ala Thr Ala Leu Ser Ser Leu Ser Leu Gly Ala Gly
                85                  90                  95

Pro Arg Thr Glu Ser Leu Ile His Arg Ala Leu Tyr Tyr Asp Leu Ile
           100                 105                 110

His Asn Pro Asp Ile His Gly Thr Tyr Lys Glu Leu Leu Ala Thr Val
       115                 120                 125

Thr Ala Pro Gln Lys Asn Leu Lys Thr Ala Ser Arg Leu Val Leu Glu
   130                 135                 140

Arg Lys Leu Arg Ile Lys Ala Gly Phe Val Gly Leu Leu Glu Lys Ser
145                 150                 155                 160

Tyr Gly Ser Arg Pro Lys Ile Leu Thr Gly Asn Thr Arg Thr Asp Leu
               165                 170                 175

His Glu Met Asn Asn Trp Met Gln Thr Gln Thr Lys Gly Lys Met Gly
           180                 185                 190

Arg Thr Leu Lys Glu Leu Pro Ser Gly Ile Ser Val Leu Leu Leu Gly
       195                 200                 205

Ile Ala Tyr Phe Lys Gly Gln Trp Val Thr Lys Phe Asp Pro Lys Lys
   210                 215                 220

Thr Ser Leu Gln Asp Phe His Leu Asp Glu Asp Arg Thr Val Lys Val
225                 230                 235                 240

Pro Met Met Ser Asp Pro Lys Ala Ile Ile Arg Tyr Gly Leu Asp Ser
               245                 250                 255

Asp Leu Asn Cys Lys Ile Ala Gln Leu Pro Leu Glu Gly Ser Met Ser
           260                 265                 270

Val Ile Phe Phe Leu Pro Leu Lys Ala Thr Gln Asn Leu Thr Leu Ile
       275                 280                 285

Glu Glu Ser Leu Thr Ser Glu Phe Ile His Asp Ile Asp Arg Glu Leu
   290                 295                 300
```

| Lys | Thr | Ile | Gln | Ala | Val | Leu | Thr | Val | Pro | Lys | Leu | Gln | Leu | Ser | Phe |
| 305 | | | | 310 | | | | | 315 | | | | | 320 | |

| Glu | Gly | Glu | Val | Ser | Lys | Thr | Phe | Gln | Glu | Ile | Lys | Leu | Gln | Ser | Leu |
| | | | | 325 | | | | | 330 | | | | | 335 | |

| Phe | Asn | Ser | Pro | Asp | Leu | Ser | Lys | Ile | Thr | Pro | Arg | Pro | Ile | Lys | Leu |
| | | | 340 | | | | | 345 | | | | | 350 | | |

| Thr | His | Val | His | Arg | Ser | Ser | Leu | Glu | Trp | Ser | Glu | Asp | Gly | Val |
| | | | 355 | | | | | 360 | | | | | 365 | |

| Gly | Asp | Ala | Pro | Ser | Pro | Ala | Leu | Leu | Pro | Ala | Arg | Leu | Thr | Phe | Pro |
| | 370 | | | | | 375 | | | | | 380 | | | | |

| Leu | Asp | Tyr | His | Leu | Asn | Gln | Pro | Phe | Ile | Phe | Val | Leu | Arg | Asp | Thr |
| 385 | | | | 390 | | | | | 395 | | | | | 400 | |

| Asp | Thr | Gly | Thr | Leu | Leu | Phe | Ile | Gly | Lys | Ile | Leu | Asp | Pro | Arg | Gly |
| | | | | 405 | | | | | 410 | | | | | 415 | |

Asn

<210> SEQ ID NO 49
<211> LENGTH: 1484
<212> TYPE: DNA
<213> ORGANISM: Canis lupus familiaris

<400> SEQUENCE: 49

```
ctggattggg aggcgcagca aaagctctgg tgcttgctgg agccctcag cctgcagacc      60
taggctggcg cagagctgca gcacacccac aggtcccagg atgcaggccc tcgtgctact    120
cctctggacc ggagccctcc tggggcacag cagctgccag aacgatgcgg gcggcccca    180
aggactctcc agctcccgac gcgacagggg tgcccgtgga ggaggaggac cccttcttca    240
gggtccccgt gaataagctg gcagcagcca tctccaactt cggctatgac ctgtaccgtg    300
taaggtccag cttcagccct gctgccaatg tgctgctgtc accactcagc gtggccaccg    360
cactctctgc gctctcgctg ggagcggaac agcggacaga atccaccatt accgggctc    420
tctactacga cctgatcagc aacccggaca tccacagcac ctataaggag ctccttgcct    480
ctgtcactgc cccggagaag aacttcaaga gtgcttcccg gattgtcttt gagaggaagc    540
tgcggataaa atccagcttt gttgcaccac tggagaagtc ctatagcacc aggcccagaa    600
tcctgaccgg caaccctcgc ctggaccttc aggaggttaa caactgggtg caggcccaga    660
tgaaagggaa aattgctaga tccacacggg aaatacccag tggaatcagc attctccttc    720
ttggtgtggc ttacttcaag gggcagtggg taacaaagtt tgactccaga aagacttccc    780
tcgaggattt ccacttggat gaggagagga ctgtgaaagt ccccatgatg tcagacccta    840
aggccatctt acgctatggc ttggactctg atctcagctg taagattgcc cagctgccct    900
tgaccggcag catgagtatc atcttttttcc tgcctctgaa agtaacccag aacttgacca    960
tgatagaaga gagcctcacc tctgagttca ttcatgacat agaccgagag ctgaagacaa   1020
ttcaagcagt cctgaccatc cccaagctga agctgagtta tgaaggcgaa gtcacgaagt   1080
ccctgcagga aatgaaactg caatccttgt ttgattcacc agacttcagc aagatcacag   1140
gcaaacctat taaacttacc caagtggaac atcgagctgg cttcgagtgg aacgaggatg   1200
gggcaggcac caccccagc ccggggctcc agcctacccg cctcacctt cctctggatt   1260
atcacctgaa ccgacctttc atctttgtgc tgagagacac agacacaggg gcccttctct   1320
tcataggcaa atcctggac cccaggggca tttaatgctc cggttttaa tgttccaata   1380
ccctagaaga acaaaaccct caacggatgg cagatgacat attacatgaa ggctgcccct   1440
```
acaatggttt cagtgtatac tttgcaataa aagtgcttta tcct          1484

<210> SEQ ID NO 50
<211> LENGTH: 396
<212> TYPE: PRT
<213> ORGANISM: Canis lupus familiaris

<400> SEQUENCE: 50

Met Arg Ala Ala Pro Lys Asp Ser Pro Ala Pro Asp Ala Thr Gly Val
1               5                   10                  15

Pro Val Glu Glu Glu Asp Pro Phe Phe Arg Val Pro Val Asn Lys Leu
            20                  25                  30

Ala Ala Ala Ile Ser Asn Phe Gly Tyr Asp Leu Tyr Arg Val Arg Ser
        35                  40                  45

Ser Phe Ser Pro Ala Ala Asn Val Leu Leu Ser Pro Leu Ser Val Ala
    50                  55                  60

Thr Ala Leu Ser Ala Leu Ser Leu Gly Ala Glu Gln Arg Thr Glu Ser
65                  70                  75                  80

Thr Ile His Arg Ala Leu Tyr Tyr Asp Leu Ile Ser Asn Pro Asp Ile
                85                  90                  95

His Ser Thr Tyr Lys Glu Leu Leu Ala Ser Val Thr Ala Pro Glu Lys
            100                 105                 110

Asn Phe Lys Ser Ala Ser Arg Ile Val Phe Glu Arg Lys Leu Arg Ile
        115                 120                 125

Lys Ser Ser Phe Val Ala Pro Leu Glu Lys Ser Tyr Ser Thr Arg Pro
    130                 135                 140

Arg Ile Leu Thr Gly Asn Pro Arg Leu Asp Leu Gln Glu Val Asn Asn
145                 150                 155                 160

Trp Val Gln Ala Gln Met Lys Gly Lys Ile Ala Arg Ser Thr Arg Glu
                165                 170                 175

Ile Pro Ser Gly Ile Ser Ile Leu Leu Leu Gly Val Ala Tyr Phe Lys
            180                 185                 190

Gly Gln Trp Val Thr Lys Phe Asp Ser Arg Lys Thr Ser Leu Glu Asp
        195                 200                 205

Phe His Leu Asp Glu Glu Arg Thr Val Lys Val Pro Met Met Ser Asp
    210                 215                 220

Pro Lys Ala Ile Leu Arg Tyr Gly Leu Asp Ser Asp Leu Ser Cys Lys
225                 230                 235                 240

Ile Ala Gln Leu Pro Leu Thr Gly Ser Met Ser Ile Ile Phe Phe Leu
                245                 250                 255

Pro Leu Lys Val Thr Gln Asn Leu Thr Met Ile Glu Glu Ser Leu Thr
            260                 265                 270

Ser Glu Phe Ile His Asp Ile Asp Arg Glu Leu Lys Thr Ile Gln Ala
        275                 280                 285

Val Leu Thr Ile Pro Lys Leu Lys Leu Ser Tyr Glu Gly Glu Val Thr
    290                 295                 300

Lys Ser Leu Gln Glu Met Lys Leu Gln Ser Leu Phe Asp Ser Pro Asp
305                 310                 315                 320

Phe Ser Lys Ile Thr Gly Lys Pro Ile Lys Leu Thr Gln Val Glu His
                325                 330                 335

Arg Ala Gly Phe Glu Trp Asn Glu Asp Gly Ala Gly Thr Thr Pro Ser
            340                 345                 350

Pro Gly Leu Gln Pro Thr Arg Leu Thr Phe Pro Leu Asp Tyr His Leu
        355                 360                 365

Asn Arg Pro Phe Ile Phe Val Leu Arg Asp Thr Asp Thr Gly Ala Leu
    370                 375                 380

Leu Phe Ile Gly Lys Ile Leu Asp Pro Arg Gly Ile
385                 390                 395

<210> SEQ ID NO 51
<211> LENGTH: 1579
<212> TYPE: DNA
<213> ORGANISM: Macaca fascicularis

<400> SEQUENCE: 51

| | | | | | | |
|---|---|---|---|---|---|---|
| agtgatgcaa | tctcagaatc | caaattgagt | gcaggtcgct | ttaagaaagg | agtagctgta | 60 |
| atctgaagcc | tgctggacgc | tggattagaa | ggcagcaaaa | aaagctcttg | tgctggctgg | 120 |
| agcccctca | gtgtgcaggc | ttggtgggac | taggctgggt | gtggagctgc | agcgtatcca | 180 |
| caggccccag | gatgcaggcc | ctggtgctat | tcctctgctt | tgcagctctc | ctcgggcaca | 240 |
| gcagctgcca | gagcctcgcc | agcggcccgg | aggagggctc | cccagacccc | gacagcacag | 300 |
| gagcgctggt | ggaggaggaa | gatcctttct | tcaaagtccc | ggtgaacaag | ctggcagcgg | 360 |
| ctgtctccaa | ctttggctat | gacctgtacc | gggtgcggtc | cagcatgagc | cccacgacca | 420 |
| acgtgctcct | gtctcctctc | agtgtggcca | cggccctctc | ggcgctctcg | ctgggagcgg | 480 |
| agcagcgaac | ggaatccgtc | attcaccggg | ctctctacta | tgacctgatc | agcagcccag | 540 |
| acatccacgg | cacctacaag | gagctccttg | gcacggtcac | cgcccccag | aaaaacctca | 600 |
| agagtgcctc | ccggatcgtc | tttgagaaga | agctgcgcat | aaaatccagc | tttgtggcac | 660 |
| ccctggaaaa | gtcatatggg | accaggccca | gagtcctgac | gggcaaccct | cgcttggacc | 720 |
| tgcaggagat | caacaactgg | gtgcaggccc | agatgaaagg | gaagctcgcc | aggtccacga | 780 |
| aggaactgcc | cgatgagatc | agtattctcc | ttcttggtgt | ggcgtacttc | aaggggcagt | 840 |
| gggtaacaaa | gtttgacccc | agaaagactt | ccctcgagga | cttccacttg | gatgaagaga | 900 |
| ggaccgtgag | ggtccccatg | atgtcagacc | ctaaggctat | tttacgctat | ggcttggatt | 960 |
| cggatctcag | ctgcaagatt | gcccagctgc | ctttgaccgg | aagcatgagt | atcatcttct | 1020 |
| tcctgcccct | caaagtgacc | cagaatttga | ccctgataga | ggagagcctc | acctccgagt | 1080 |
| tcattcacga | catagaccgg | gaactgaaga | cggtgcaggc | ggtcctgacc | ctccccaagc | 1140 |
| tgaagctgag | ttacgaaggc | gaagtcacca | agtcgctaca | ggagacgaag | ctgcagtctt | 1200 |
| tgtttgattc | accagacttt | agcaagatca | caggcaaacc | catcaagctg | actcaagtgg | 1260 |
| aacaccgggc | cggcttcgag | tggaacgagg | atgggcggg | agccaccccc | agcccggggc | 1320 |
| tgcagcctgc | gcacctcacc | ttcctgctgg | actatcacct | taaccagcct | ttcatcttcg | 1380 |
| tcctgaggga | cacggacaca | ggggcccttc | tcttcattgg | caagattctg | gaccccagag | 1440 |
| gcacctaata | ccctgtttaa | cattccagtg | ccctagaagg | gaaccctaga | gggacagcag | 1500 |
| attccacagg | acacaaagct | gctcccgtaa | ggtttcaatg | catacaataa | aagagcttta | 1560 |
| tccttaaaaa | aaaaaaaaa | | | | | 1579 |

<210> SEQ ID NO 52
<211> LENGTH: 418
<212> TYPE: PRT
<213> ORGANISM: Macaca fascicularis

<400> SEQUENCE: 52

Met Gln Ala Leu Val Leu Phe Leu Cys Phe Ala Ala Leu Leu Gly His
1               5                   10                  15

Ser Ser Cys Gln Ser Leu Ala Ser Gly Pro Glu Glu Gly Ser Pro Asp
              20                  25                  30

Pro Asp Ser Thr Gly Ala Leu Val Glu Glu Asp Pro Phe Phe Lys
         35                  40                  45

Val Pro Val Asn Lys Leu Ala Ala Val Ser Asn Phe Gly Tyr Asp
    50                  55                  60

Leu Tyr Arg Val Arg Ser Ser Met Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Val Ile His Arg Ala Leu Tyr Tyr Asp Leu
            100                 105                 110

Ile Ser Ser Pro Asp Ile His Gly Thr Tyr Lys Glu Leu Leu Gly Thr
            115                 120                 125

Val Thr Ala Pro Gln Lys Asn Leu Lys Ser Ala Ser Arg Ile Val Phe
130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
            180                 185                 190

Ala Arg Ser Thr Lys Glu Leu Pro Asp Glu Ile Ser Ile Leu Leu Leu
            195                 200                 205

Gly Val Ala Tyr Phe Lys Gly Gln Trp Val Thr Lys Phe Asp Pro Arg
210                 215                 220

Lys Thr Ser Leu Glu Asp Phe His Leu Asp Glu Arg Thr Val Arg
225                 230                 235                 240

Val Pro Met Met Ser Asp Pro Lys Ala Ile Leu Arg Tyr Gly Leu Asp
                245                 250                 255

Ser Asp Leu Ser Cys Lys Ile Ala Gln Leu Pro Leu Thr Gly Ser Met
            260                 265                 270

Ser Ile Ile Phe Phe Leu Pro Leu Lys Val Thr Gln Asn Leu Thr Leu
            275                 280                 285

Ile Glu Glu Ser Leu Thr Ser Glu Phe Ile His Asp Ile Asp Arg Glu
290                 295                 300

Leu Lys Thr Val Gln Ala Val Leu Thr Leu Pro Lys Leu Lys Leu Ser
305                 310                 315                 320

Tyr Glu Gly Glu Val Thr Lys Ser Leu Gln Glu Thr Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
            355                 360                 365

Ala Gly Ala Thr Pro Ser Pro Gly Leu Gln Pro Ala His Leu Thr Phe
370                 375                 380

Leu Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Thr

<210> SEQ ID NO 53

<211> LENGTH: 1935
<212> TYPE: DNA
<213> ORGANISM: Pan troglodytes

<400> SEQUENCE: 53

| | | | | | |
|---|---|---|---|---|---|
| aaaaaaagct | ctgtgctggc | tggagccccc | tcagtgtgca | ggcttagagg | gactaggctg | 60 |
| ggtgtggagc | tgcagcgtat | ccacaggccc | caggatgcag | gccctggtgc | tactcctctg | 120 |
| cattggagcc | ctcctcgggc | acagcagctg | ccagaaccct | gccagccccc | cggaggagag | 180 |
| agctcatgcg | tgatcaggga | ataaaactca | ttcccgtttt | aggccaaaca | cagaaaaatt | 240 |
| aggaaggaca | gccccaaggg | gccagaacca | ccaccctaca | caaagccatg | aggagacagt | 300 |
| cagtccctgt | gcatctctgc | gagtccctga | actcaaaccc | aagacttcct | gtctcctgcc | 360 |
| agggctcccc | agaccccgac | agcacagggg | cgctggtgga | ggaggaagat | cctttcttca | 420 |
| aagtccccgt | gaacaagctg | gcagcggctg | tctccaactt | cggctatgac | ctgtaccggg | 480 |
| tgcgatccag | catgagcccc | acgaccaacg | tgctcctgtc | tcctctcagt | gtggccacgg | 540 |
| ccctctcggc | cctctcgctg | ggagcggagc | agcgaacaga | atccatcatt | caccgggctc | 600 |
| tctactatga | cttgatcagc | agcccagaca | tccatggtac | ctacaaggag | ctccttgaca | 660 |
| cggtcactgc | cccccagaag | aacctcaaga | gtgcctcccg | gatcgtcttt | gagaagaagc | 720 |
| tgcgcataaa | atccagcttt | gtggcacctc | tggaaaagtc | atatgggacc | aggcccagag | 780 |
| tcctgacggg | caaccctcgc | ttggacctgc | aggagatcaa | caactgggtg | caggcgcaga | 840 |
| tgaaagggaa | gctcgccagg | tccacaaagg | aaattcccga | tgagatcagc | attctccttc | 900 |
| tcggtgtggc | gcacttcaag | gggcagtggg | taacaaagtt | tgactccaga | aagacttccc | 960 |
| tcgaggattt | ccacttggat | gaagagagga | cagtgagggt | ccccatgatg | tcggaccct a | 1020 |
| aggctgtttt | acgctatggc | ttggattcag | atctcagctg | caagattgcc | cagctgccct | 1080 |
| tgaccggaag | cacgagtatc | atcttcttcc | tgccctgaa | agtgacccag | aatttgacct | 1140 |
| tgatagagga | gagcctcacc | tctgagttca | ttcatgacat | agaccgagaa | ctgaagaccg | 1200 |
| tgcaggcggt | cctgaccgtc | cccaagctga | agctgagtta | cgaaggcgaa | gtcaccaagt | 1260 |
| ccctgcagga | gatgaagctg | caatccttgt | ttgattcacc | agactttagc | aagatcacag | 1320 |
| gcaaacccat | caagctgact | caggtggaac | accgggctgg | cttcgagtgg | aacgaggatg | 1380 |
| gggcgggaac | caccccagc | ccagggctgc | agcctgccca | cctcaccttc | ccgctggact | 1440 |
| atcaccttaa | ccagccttc | atcttcgtac | tgagggacac | agacacaggg | gcccttctct | 1500 |
| tcattggcaa | gattctggac | cccaggggca | cctaataccc | cagtttaata | ttccaatacc | 1560 |
| ctagaagaaa | acccgaggga | cagcagattc | cacaggacac | gaaggctgcc | cctgtaaggt | 1620 |
| ttcaatgcat | aaaataaaag | agctttatcc | ctaacttctg | ttacttcgtt | cctcctccta | 1680 |
| ttttgagcta | tgcgaaatat | catatgaaga | gaaacagctc | tttaggaatt | tggtggtcct | 1740 |
| ctacttctag | cctggttta | tctaaacact | gcaggaagtc | accgtttata | agaactctta | 1800 |
| gttagctgtg | gtggataatg | cacggacagc | tgctctgctc | tggggggtgtt | tctgtactag | 1860 |
| gatcagcgat | cctcccggga | ggccatttcc | tgcccccata | atcagggaag | catgctcgta | 1920 |
| agcaacacat | ggaca | | | | | 1935 |

<210> SEQ ID NO 54
<211> LENGTH: 415
<212> TYPE: PRT
<213> ORGANISM: Pan troglodytes

<400> SEQUENCE: 54

```
Met Arg Arg Gln Ser Val Pro Val His Leu Cys Glu Ser Leu Asn Ser
1               5                   10                  15

Asn Pro Arg Leu Pro Val Ser Cys Gln Gly Ser Pro Asp Pro Asp Ser
            20                  25                  30

Thr Gly Ala Leu Val Glu Glu Asp Pro Phe Phe Lys Val Pro Val
        35                  40                  45

Asn Lys Leu Ala Ala Ala Val Ser Asn Phe Gly Tyr Asp Leu Tyr Arg
50                      55                  60

Val Arg Ser Ser Met Ser Pro Thr Thr Asn Val Leu Leu Ser Pro Leu
65              70                  75                      80

Ser Val Ala Thr Ala Leu Ser Ala Leu Ser Leu Gly Ala Glu Gln Arg
                85                  90                  95

Thr Glu Ser Ile Ile His Arg Ala Leu Tyr Tyr Asp Leu Ile Ser Ser
                100                 105                 110

Pro Asp Ile His Gly Thr Tyr Lys Glu Leu Leu Asp Thr Val Thr Ala
            115                 120                 125

Pro Gln Lys Asn Leu Lys Ser Ala Ser Arg Ile Val Phe Glu Lys Lys
        130                 135                 140

Leu Arg Ile Lys Ser Ser Phe Val Ala Pro Leu Glu Lys Ser Tyr Gly
145                 150                 155                 160

Thr Arg Pro Arg Val Leu Thr Gly Asn Pro Arg Leu Asp Leu Gln Glu
                165                 170                 175

Ile Asn Asn Trp Val Gln Ala Gln Met Lys Gly Lys Leu Ala Arg Ser
            180                 185                 190

Thr Lys Glu Ile Pro Asp Glu Ile Ser Ile Leu Leu Leu Gly Val Ala
        195                 200                 205

His Phe Lys Gly Gln Trp Val Thr Lys Phe Asp Ser Arg Lys Thr Ser
    210                 215                 220

Leu Glu Asp Phe His Leu Asp Glu Glu Arg Thr Val Arg Val Pro Met
225                 230                 235                 240

Met Ser Asp Pro Lys Ala Val Leu Arg Tyr Gly Leu Asp Ser Asp Leu
                245                 250                 255

Ser Cys Lys Ile Ala Gln Leu Pro Leu Thr Gly Ser Thr Ser Ile Ile
            260                 265                 270

Phe Phe Leu Pro Leu Lys Val Thr Gln Asn Leu Thr Leu Ile Glu Glu
        275                 280                 285

Ser Leu Thr Ser Glu Phe Ile His Asp Ile Asp Arg Glu Leu Lys Thr
    290                 295                 300

Val Gln Ala Val Leu Thr Val Pro Lys Leu Lys Leu Ser Tyr Glu Gly
305                 310                 315                 320

Glu Val Thr Lys Ser Leu Gln Glu Met Lys Leu Gln Ser Leu Phe Asp
                325                 330                 335

Ser Pro Asp Phe Ser Lys Ile Thr Gly Lys Pro Ile Lys Leu Thr Gln
            340                 345                 350

Val Glu His Arg Ala Gly Phe Glu Trp Asn Glu Asp Gly Ala Gly Thr
        355                 360                 365

Thr Pro Ser Pro Gly Leu Gln Pro Ala His Leu Thr Phe Pro Leu Asp
370                 375                 380

Tyr His Leu Asn Gln Pro Phe Ile Phe Val Leu Arg Asp Thr Asp Thr
385                 390                 395                 400

Gly Ala Leu Leu Phe Ile Gly Lys Ile Leu Asp Pro Arg Gly Thr
                405                 410                 415
```

<210> SEQ ID NO 55
<211> LENGTH: 833
<212> TYPE: DNA
<213> ORGANISM: Macaca mulatta

<400> SEQUENCE: 55

```
atgtggggat ctgctgcccc ctggccagtg cctggggatg ccagcagaag tcctgagctg    60
cgcataaaat ccagctttgt ggcacccctg gaaaagtcat atgggaccag cccagagtc   120
ctgacgggca accctcgctt ggacctgcag gagatcaaca actgggtgca ggcccagatg   180
aaagggaagc tcgccaggtc cacgaaggag ctgcccgatg agatcagtat tctccttctc   240
ggtgtggcgt acttcaaggg gcagtgggta acaaagtttg accccagaaa gacttccctc   300
gaggacttcc acttggatga agagaggacc gtgagggtcc ccatgatgtc agaccctaag   360
gctattttac gctatggctt ggattcggat ctcagctgca agattgccca gctgcctttg   420
accggaagca tgagtatcat cttcttcctg cccctcaaag tgacccagaa tttgaccctg   480
atagaggaga gcctcacctc cgagttcatt acgacatag accgggaact gaagacggtg   540
caggcggtcc tgaccctccc caagctgaag ctgagttacg aaggcgaagt caccaagtcg   600
ctgcaggaga cgatggacta tcaccttaac cagccttttca tcttcgtcct gagggacacg   660
gacacagggg cccttctctt cattggcaag attctggacc ccagaggcac ctaatacct    720
gtttaacatt ccagtgccct agaagggaac cctagaggga cagcagattc cacaggacac   780
aaagctgctc ccgtaaggtt tcaatgcata caataaaaga gctttatcct taa           833
```

<210> SEQ ID NO 56
<211> LENGTH: 237
<212> TYPE: PRT
<213> ORGANISM: Macaca mulatta

<400> SEQUENCE: 56

```
Met Trp Gly Ser Ala Ala Pro Trp Pro Val Pro Gly Asp Ala Ser Arg
  1               5                  10                  15

Ser Pro Glu Leu Arg Ile Lys Ser Ser Phe Val Ala Pro Leu Glu Lys
             20                  25                  30

Ser Tyr Gly Thr Arg Pro Arg Val Leu Thr Gly Asn Pro Arg Leu Asp
         35                  40                  45

Leu Gln Glu Ile Asn Asn Trp Val Gln Ala Gln Met Lys Gly Lys Leu
     50                  55                  60

Ala Arg Ser Thr Lys Glu Leu Pro Asp Glu Ile Ser Ile Leu Leu Leu
 65                  70                  75                  80

Gly Val Ala Tyr Phe Lys Gly Gln Trp Val Thr Lys Phe Asp Pro Arg
                 85                  90                  95

Lys Thr Ser Leu Glu Asp Phe His Leu Asp Glu Arg Thr Val Arg
            100                 105                 110

Val Pro Met Met Ser Asp Pro Lys Ala Ile Leu Arg Tyr Gly Leu Asp
        115                 120                 125

Ser Asp Leu Ser Cys Lys Ile Ala Gln Leu Pro Leu Thr Gly Ser Met
    130                 135                 140

Ser Ile Ile Phe Phe Leu Pro Leu Lys Val Thr Gln Asn Leu Thr Leu
145                 150                 155                 160

Ile Glu Glu Ser Leu Thr Ser Glu Phe Ile His Asp Ile Asp Arg Glu
                165                 170                 175

Leu Lys Thr Val Gln Ala Val Leu Thr Leu Pro Lys Leu Lys Leu Ser
            180                 185                 190
```

Tyr Glu Gly Glu Val Thr Lys Ser Leu Gln Glu Thr Met Asp Tyr His
    195                 200                 205

Leu Asn Gln Pro Phe Ile Phe Val Leu Arg Asp Thr Asp Thr Gly Ala
    210                 215                 220

Leu Leu Phe Ile Gly Lys Ile Leu Asp Pro Arg Gly Thr
225                 230                 235

<210> SEQ ID NO 57
<211> LENGTH: 4645
<212> TYPE: DNA
<213> ORGANISM: Paralichthys olivaceus

<400> SEQUENCE: 57

| | | | | | |
|---|---|---|---|---|---|
| ggcagagaaa | cagtcggagc | gacgttgatc | cggatcagac | gtgagctgat | ctgagctgat | 60 |
| ctgatctgag | ctgagctgat | ctgatctgag | ctgatctgac | ctgagctgat | ctgagggtga | 120 |
| gtggtgactt | tacagctgac | ttcagagatg | atctgatcag | aaacaacaga | tttatttcac | 180 |
| cggagtttct | gaacaactca | tcagttcttt | taaaaaccgg | atcagaacca | ggacacacgc | 240 |
| gtctgtggtc | ggatcagttt | gtaattcagg | aacaagaata | aaaataagtg | tttaactttc | 300 |
| atcttatctc | acttcatcta | taaatggatc | aactgaggtt | tctcagtgtg | atctggtgt | 360 |
| gactctggtt | tttaactgtt | tctggaaaca | ttcagattct | caacattatt | catctcgagt | 420 |
| ttttacatct | gtgtagtttc | tatggattta | ctgcaaactg | tccgttaaac | caggagtttc | 480 |
| tcatcagtgt | gtgtgtgtat | gtgagtgtgc | acgtttgtgt | gcgtgtgtgt | gtgtatctgt | 540 |
| ttgtttctgt | gtgtgtgtgt | gtgtgtgcat | gcgtgtggta | tgtgtgtgca | tgcgtgtgta | 600 |
| tgtgtgtgtg | cgcgcgcgcg | cgcgtgtgtg | tgtgtgtaca | tgcggtctga | ggtccagatg | 660 |
| acagactttt | gtttctgtaa | ccatgacaac | cagctccaga | tgttcagag | gaacaaagga | 720 |
| actttgtgcg | tcagagcttt | tgtttgaaac | ttgtttgtgt | ccgaatgaaa | atgttgagct | 780 |
| tgaggaatga | gatcaccttt | ctctgctcag | atgttcagaa | ggttttttgga | tgatggatta | 840 |
| tttggaggtt | tgaggtttgg | gagctggatc | ctgtgggttt | tcactgtgat | tatacaaaac | 900 |
| actgagggag | acattggtcg | tctttgtctc | tgacactgtc | tcagtgtctc | cacatattct | 960 |
| cctccaggtt | ttctctttgc | ctgagattca | ttgtgtttcc | tgcagtgaga | ttgtgacacg | 1020 |
| tcttcaccct | caggtgtttg | tgttgcagat | gaagacaaca | acattcctgc | tgatgtgtgg | 1080 |
| agtcgtcctg | agcttcagtc | aggctcaggt | atcacatcag | ctgtttctga | tttctcacac | 1140 |
| aggaagttac | tgttgtgacg | tgattgttgt | gtaacacaca | aatacaccaa | catcaaacac | 1200 |
| acccagtata | tttcagtaat | tacagtgaaa | gtgtccgacg | actcttctct | gtcctgtttc | 1260 |
| cagtcggagg | gcgaggagac | gactgtggag | gaggagcatg | tcgagctctt | caccacacca | 1320 |
| actacgaggt | tggcagccgc | cacctccgac | tttggctaca | acctgttccg | atctctggcg | 1380 |
| agtcgcgaca | ccacgaccaa | cgtcttcctg | gcccccatca | gtgtgtctgc | ggcgctgacc | 1440 |
| caactgtcca | tgggtgaagg | cacaaactca | acacaaacta | aaaacattca | cagaaattga | 1500 |
| gttcaggtaa | agactccatc | gtcatcaggt | ggtcgtcact | ttgttttcct | acatttgacg | 1560 |
| gaaaattaca | catagacaca | gaggaactga | tgttttttaat | gatttctgct | cgagctgaag | 1620 |
| tttccatctg | aactcaacct | ggtctgacaa | aagttcagag | tcctgcaccg | aggctgagct | 1680 |
| cagaatcttc | tccatcagaa | gctgtttaag | aaaatgattt | ccaataaact | gtttccatgg | 1740 |
| agttttttcct | tgagggcgac | acgttgcata | aaaatgttgg | aggaggagaa | aggttttgat | 1800 |
| tcacaacaga | atgttctctgc | atgatggaaa | aacctcaaac | ccatgaacag | tttcatgaat | 1860 |

```
aagaagtcat tcattatttt ggctgtagaa tcattctctc caagtagaaa acatttaaat    1920
aatgttaata aacctcgttc tgacaaagct gagaattatt gtggctgtaa aagagaaaac    1980
tgcctcaaag cctttgaact gctccaagat ggagacaaga gacaagggat catatttctc    2040
ttaacataaa acaaatgtga atcctctggt tcagtgatac tgttgctgaa tctgtctaaa    2100
gtatgaagtt gctcatgtca gggtctttaa acttaatgtt cttccaccga taaggaaac     2160 tgttcacgtg agaatctgac atgtctcctg caggagggtc agagctggct gagcggcagc    2220
tgttcagggc tctgaggttt cacaccctgc aggaccctca gctccacaac ccctgaagg     2280 acctgttggc ctccctccgc tcacctggga aaggcctgag catcgctgct cgtctctacc    2340
tggctcgacg agtagttcac ctggaacatg tgataactgt taaatgtgtt ttcagatagg    2400
ggggtcaact ggttgaacag atcaggtctc ttcttcttct tcgtttggtt tattggtgga    2460
tggcaaccaa cgtcaaggtg tactgccccc tggaggtact gtaattccag gtatagtgca    2520
gctgcagttt ttgagcagca agcaagtgat tccaggaaaa agaaatatac tttaaagacg    2580
cagtatcaga cgggtacatt gatttgggta ctctacattt ttggcagcat caggtatcgg    2640
ttttgaaacc tttttaacaa caaggtgttg aattaatatg ccctcatgga aatctctttt    2700
ggttgtgttg ctgtgtttag cttcgtctga accaggagtt cttggcgctg gtggagcagc    2760
agtatggagt tcgtccaaag gcattgccgg ttggaggcaa agatttgaaa gaaatcaacg    2820
actgggtgtc tcaggagacc ggcgggaagg tgcagcgctt cctggccaaa ccctcctctc    2880
gaaacccttc agtgaacact gtgagcgccg cctactttaa agggtgcgtc gggaggattt    2940
caaactcaac atctttacat cgacagtttg atgccggtca catgtgacga cacagttttc    3000
tgttaacagg aggtgggtca ctcgcttcag taacagtgga gtcatggagg agtttcaggt    3060
ggacggcgcg gcacctgttc gcgttcccat gatgcagcag gacaactatc ctgtgaagat    3120
gggagccgac tcagacttga gctgcacggt gagtgttttc tacttcttcc atttcatttc    3180
tgaaatttgt cctgaacaat gtttatttg ctcgtccacc agattgctca gatccagatg      3240
cagaatgacg ttagcatgtt catcttcctg ccagacgagg ttatgtccaa catgacactg    3300
ctggaggaga gtctgaccgc tgagtttgtt caggaccttt ccatgacact gctcccagcc    3360
caggtgtccc tcactctgcc taccctgagg ctcagctact ccacagacct gctgccactg    3420
ctcagcgacc tgggtgagtc cagaaccagg tccaggtctg actttaccac aataataaat    3480
atggaaatga tttgaatgat ttgaatacca acaagttatg aggttcagtt ttgtcaggag    3540
ctacttaaat gtattttctt tgtgtttcta ctccacaaca aaatacattt cttggtttga    3600
agatctgaat gtttgtaaaa acaaaaagga gtcaaacaga gaaaccctga ttcaaaacaa    3660
tactaataaa gtgagtcatc aggtcagata gagacaaaca ggcgggagca gaagaaacca    3720
tgagtgtaaa catgaggaaa agtctggaca ggaagtacaa tgacacaaga gttaagaaca    3780
acaacataaa acaggaaaca gatactgaaa cagtaactgg atgttaacgt tacagagtct    3840
tcataattca aacattacct ccagagatac agacgctctg attcatgaca actcaggatc    3900 tttcaattg tgtccgtccc tccatcgtcc ccctccctgt aggcctcact gattggatgg       3960
agaacccgca gctggagaag atctcaaccc aggctgccaa gctcaccagc gtcaatcaca    4020
aggtcatcat ggagacagca cctgaaggtg accagtaccc cggcgccatg tcaacaccca    4080
accacctgtc ataccgggtg gaccgcccct tcctctacct gatccgggac gaagcatcgg    4140
gggcgctgct cttcattggc agagtggtca accccaaaga cctgaggata taagacagat    4200
```

```
tcccataatg cattgccatt taacctcacc tcaaccctca ccccaaccct cacctcaacc    4260
ctcacctcaa ccctcacccc aaccctcacc tcaaccctca cctcaaccct caccccaacc    4320
ctcacctcac cctcacccca accctcacct caaacttcac cctagaacca agtctgagct    4380
tcaaatagca caaacaataa gacgccataa ttttctctaa actcaagctc tcttcatggt    4440
cctcttctca ggtcgtacga cagatttcag gtgtttgctc cacgtttgtg gcggcagatc    4500
tgtgaggacg tttgatttga ttttcttac ttttcatgtt gaaacaaaca cgttggtgtg    4560
atcatgttaa gatactgatg atacgaggaa agatgttaga aatattgtca tttgttttca    4620
aaggaataaa cacgacaatg aaagc                                         4645
```

<210> SEQ ID NO 58
<211> LENGTH: 403
<212> TYPE: PRT
<213> ORGANISM: Paralichthys olivaceus

<400> SEQUENCE: 58

```
Met Lys Thr Thr Thr Phe Leu Leu Met Cys Gly Val Val Leu Ser Phe
1               5                   10                  15

Ser Gln Ala Gln Ser Glu Gly Glu Thr Val Glu Glu His
            20                  25                  30

Val Glu Leu Phe Thr Thr Pro Thr Thr Arg Leu Ala Ala Ala Thr Ser
        35                  40                  45

Asp Phe Gly Tyr Asn Leu Phe Arg Ser Leu Ala Ser Arg Asp Thr Thr
    50                  55                  60

Thr Asn Val Phe Leu Ala Pro Ile Ser Val Ser Ala Ala Leu Thr Gln
65                  70                  75                  80

Leu Ser Met Gly Gly Ser Glu Leu Ala Glu Arg Gln Leu Phe Arg Ala
                85                  90                  95

Leu Arg Phe His Thr Leu Gln Asp Pro Gln Leu His Asn Thr Leu Lys
            100                 105                 110

Asp Leu Leu Ala Ser Leu Arg Ser Pro Gly Lys Gly Leu Ser Ile Ala
        115                 120                 125

Ala Arg Leu Tyr Leu Ala Arg Arg Leu Arg Leu Asn Gln Glu Phe Leu
    130                 135                 140

Ala Leu Val Glu Gln Gln Tyr Gly Val Arg Pro Lys Ala Leu Pro Val
145                 150                 155                 160

Gly Gly Lys Asp Leu Lys Glu Ile Asn Asp Trp Val Ser Gln Glu Thr
                165                 170                 175

Gly Gly Lys Val Gln Arg Phe Leu Ala Lys Pro Ser Ser Arg Asn Pro
            180                 185                 190

Ser Val Asn Thr Val Ser Ala Ala Tyr Phe Lys Gly Arg Trp Val Thr
        195                 200                 205

Arg Phe Ser Asn Ser Gly Val Met Glu Glu Phe Gln Val Asp Gly Ala
    210                 215                 220

Ala Pro Val Arg Val Pro Met Met Gln Gln Asp Asn Tyr Pro Val Lys
225                 230                 235                 240

Met Gly Ala Asp Ser Asp Leu Ser Cys Thr Ile Ala Gln Ile Gln Met
                245                 250                 255

Gln Asn Asp Val Ser Met Phe Ile Phe Leu Pro Asp Glu Val Met Ser
            260                 265                 270

Asn Met Thr Leu Leu Glu Glu Ser Leu Thr Ala Glu Phe Val Gln Asp
        275                 280                 285

Leu Ser Met Thr Leu Leu Pro Ala Gln Val Ser Leu Thr Leu Pro Thr
```

```
                290                 295                 300
Leu Arg Leu Ser Tyr Ser Thr Asp Leu Leu Pro Leu Leu Ser Asp Leu
305                 310                 315                 320

Gly Leu Thr Asp Trp Met Glu Asn Pro Gln Leu Glu Lys Ile Ser Thr
                325                 330                 335

Gln Ala Ala Lys Leu Thr Ser Val Asn His Lys Val Ile Met Glu Thr
                340                 345                 350

Ala Pro Glu Gly Asp Gln Tyr Pro Gly Ala Met Ser Thr Pro Asn His
                355                 360                 365

Leu Ser Tyr Arg Val Asp Arg Pro Phe Leu Tyr Leu Ile Arg Asp Glu
                370                 375                 380

Ala Ser Gly Ala Leu Leu Phe Ile Gly Arg Val Val Asn Pro Lys Asp
385                 390                 395                 400

Leu Arg Ile
```